US007812218B2

(12) United States Patent
Ronen et al.

(10) Patent No.: US 7,812,218 B2
(45) Date of Patent: Oct. 12, 2010

(54) POLYNUCLEOTIDES AND POLYPEPTIDES INVOLVED IN PLANT FIBER DEVELOPMENT AND METHODS OF USING SAME

(75) Inventors: Gil Ronen, Emek Hefer (IL); Evgenia Gold, Kiryat-Gat (IL); Rodrigo Yelin, Zur-Yigal (IL); Rafael Meissner, Rechovot (IL); Hagai Karchi, Moshav Sitriya (IL); Sharon Ayal, Kiryat-Ekron (IL)

(73) Assignee: Evogene Ltd., Rechovot, IL (US)

( * ) Notice: Subject to any disclaimer, the term of this patent is extended or adjusted under 35 U.S.C. 154(b) by 618 days.

(21) Appl. No.: 11/629,411

(22) PCT Filed: Jun. 14, 2005

(86) PCT No.: PCT/IL2005/000627

§ 371 (c)(1),
(2), (4) Date: Dec. 13, 2006

(87) PCT Pub. No.: WO2005/121364

PCT Pub. Date: Dec. 22, 2005

(65) Prior Publication Data

US 2009/0126042 A1    May 14, 2009

Related U.S. Application Data

(60) Provisional application No. 60/578,833, filed on Jun. 14, 2004.

(51) Int. Cl.
*C12N 15/82* (2006.01)
*C12N 5/04* (2006.01)
*A01H 5/00* (2006.01)

(52) U.S. Cl. .................. 800/278; 800/298; 800/290; 435/419

(58) Field of Classification Search .................. None
See application file for complete search history.

(56) References Cited

U.S. PATENT DOCUMENTS

| 5,495,070 A | 2/1996 | John |
| 2002/0049999 A1 | 4/2002 | Allen et al. |
| 2004/0006794 A1* | 1/2004 | Wilkins ............... 800/284 |
| 2008/0196120 A1 | 8/2008 | Wu et al. |

FOREIGN PATENT DOCUMENTS

| AU | 2005229157 | 10/2005 |
| WO | WO 95/08914 | 4/1995 |
| WO | WO 96/26639 | 9/1996 |
| WO | WO 96/40924 | 12/1996 |
| WO | WO 01/17333 | 3/2001 |
| WO | WO 03/098186 | 11/2003 |
| WO | WO 2005/095614 | 10/2005 |

OTHER PUBLICATIONS

Kirubakaran et al (2008, Plant Physiology and Biochemistry 46(10):918-927).*
Francois et al (2008, Functional Plant Biology FPB 35(5):394-402).*
Bowie et al, Science 247:1306-1310, 1990.*
McConnell et al, Nature 411 (6838):709-713, 2001.*
Wing (2000, NCBI Accession No. BE052336).*
2010, Merriam-Webster on-line Dictionary [exogenous definition].*
Supplementary European Search Report Dated Apr. 23, 2008 From the European Patent Office Re.: Application No. 05750089.4.
Written Opinion Dated Jan. 3, 2007 From the International Searching Authority Re.: Application No. PCT/IL2005/000627.
Orford et al. "Specific Expression of An Expansin Gene During Elongation of Cotton Fibres", Biochimica et Biophysica Acta, 1398: 342-346, 1998. Abstract, p. 343, Fig.1.
Wallace et al. "Oligonucleotide Probes for the Screening of Recombinant DNA Libraries", Methods in Enzymology, 152: 432-442, 1987.
Ji et al. "Gossypium Hirsutum Expansin mRNA, Complete CDs", Retrieved From EBI Accession No. EMBL:AY189969, Database Accession No. AY189969, May 20, 2003.
Ji et al. "Isolation and Analyses of Genes Preferentially Expressed During Early Cotton Fiber Development by Subtractive PCR and cDNA Array", Nucleic Acids Research, 31(10): 2534-2543, May 15, 2003.
Communication Pursuant to Article 94(3) EPC Dated Feb. 13, 2009 From the European Patent Office Re.: Application No. 05750089.4.
International Preliminary Report on Patentability Dated Mar. 29, 2007 From the International Bureau of WIPO Re.: Application No. PCT/IL2005/000627.
International Preliminary Report on Patentability Dated Jan. 30, 2007 From the International Bureau of WIPO Re.: Application No. PCT/IL05/00627.
Invitation to Pay Additional Fees Dated Sep. 8, 2006 From the International Searching Authority Re.: Application No. PCT/IL05/00627.
Translation of Notice of Payment of the Restoration Fee for Unity of Invention Dated Mar. 20, 2009 From the State Intellectual Property Office of the People's Republic of China Re.: Application No. 200580027481.4.
Examiner's Report Dated Dec. 17, 2009 From the Australian Patent Office re.: Application No. 2005252469.
Response Dated May 17, 2010 to Office Action of Jan. 22, 2010 From the State Intellectual Property Office of the People's Republic of China Re.: Application No. 200580027481.4.

* cited by examiner

*Primary Examiner*—Stuart F. Baum

(57) ABSTRACT

Isolated polynucleotides are provided. Each of the isolated polynucleotides comprise a nucleic acid sequence encoding a polypeptide having an amino acid sequence at least 80% homologous to SEQ ID NO: 26, 106, 107, 109, 110, 112, 114, 115, 118, 119, 122, 123, 124, 126, 95 or 96, wherein the polypeptide is capable of regulating cotton fiber development. Also provided are methods of using such polynucleotides for improving fiber quality and/or yield of a fiber producing plant, as well as methods of using such polynucleotides for producing plants having increased biomass/vigor/yield.

17 Claims, 7 Drawing Sheets
(7 of 7 Drawing Sheet(s) Filed in Color)

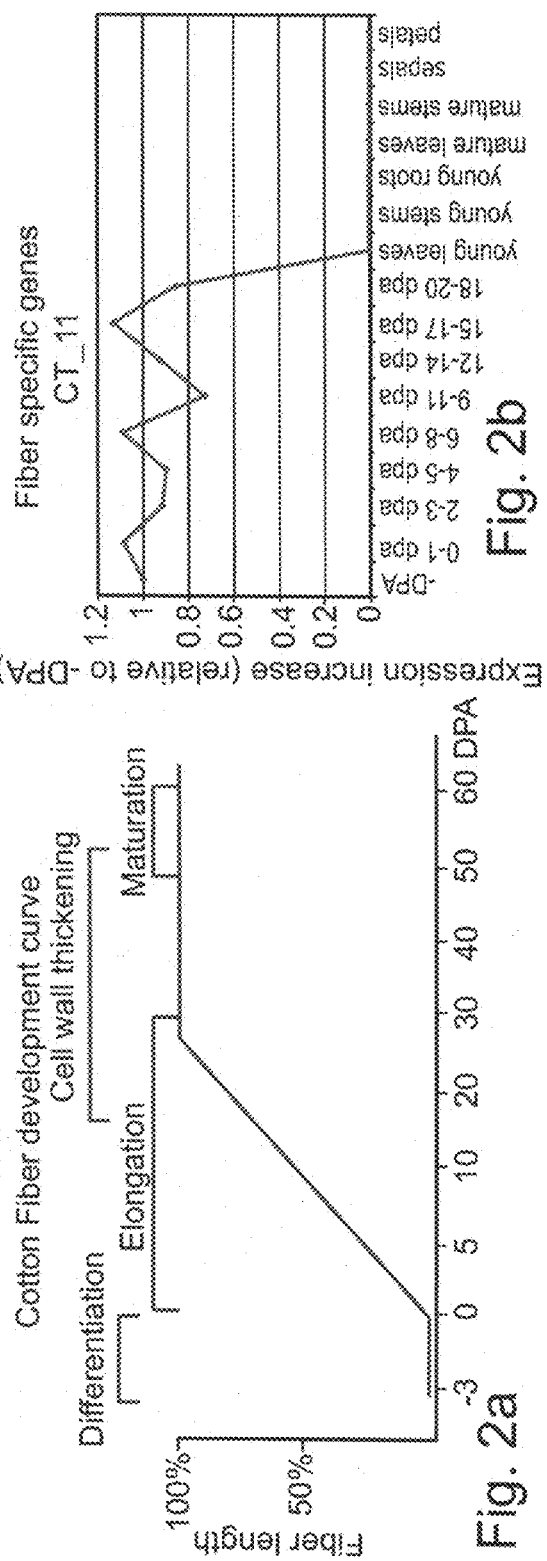
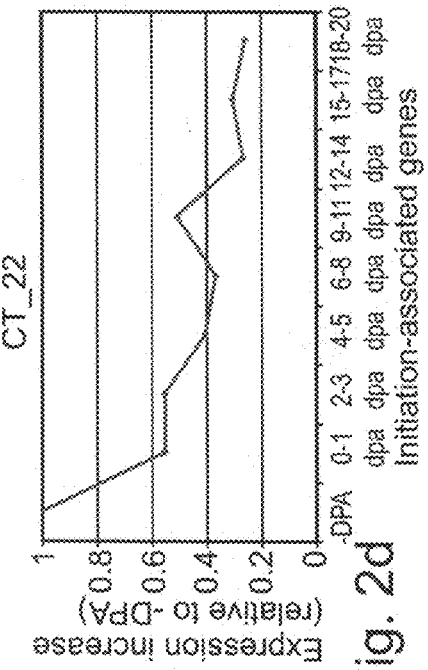
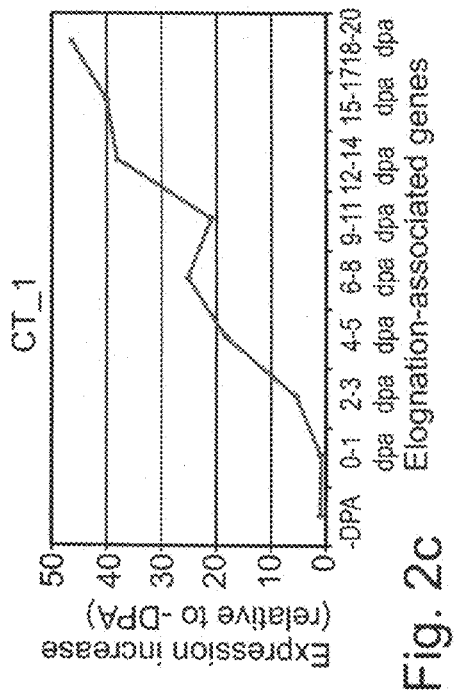

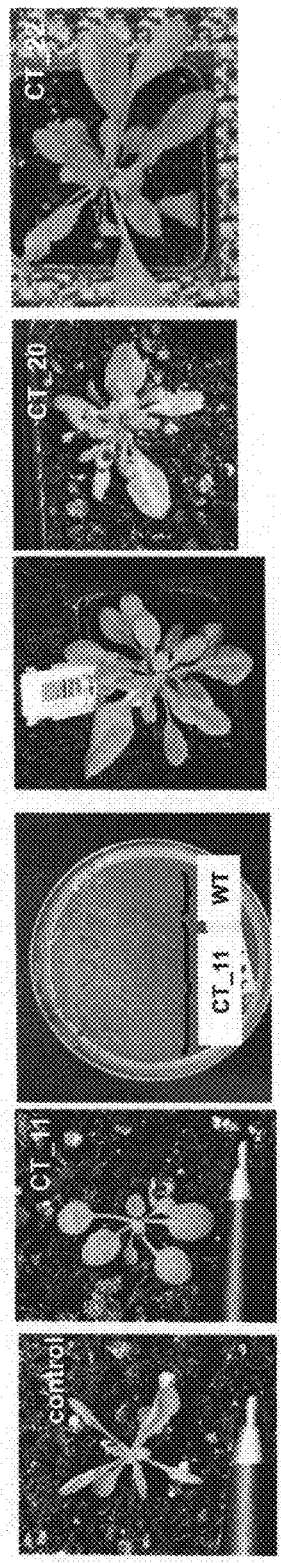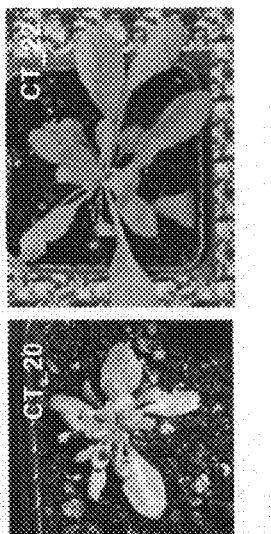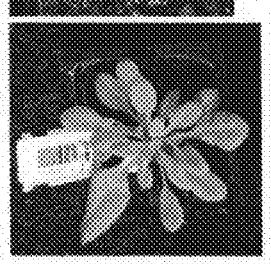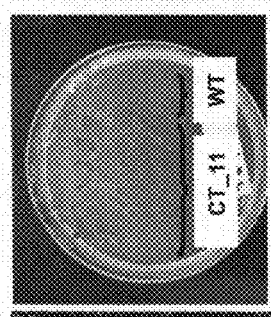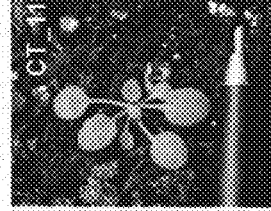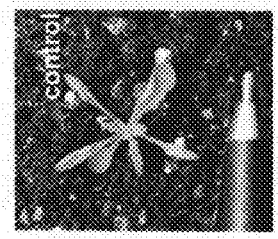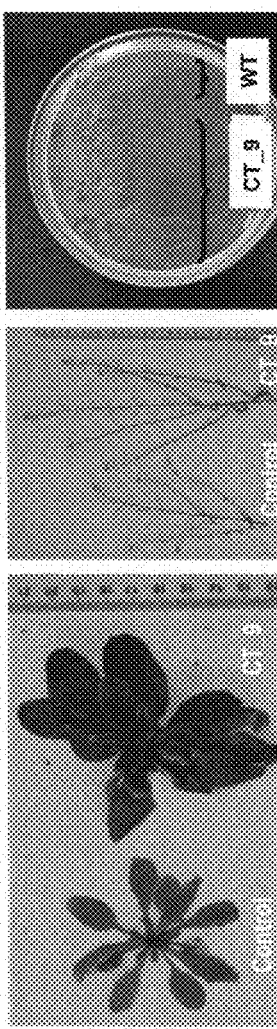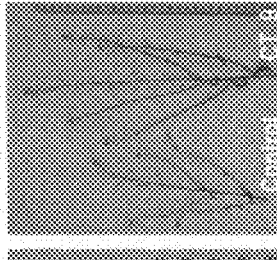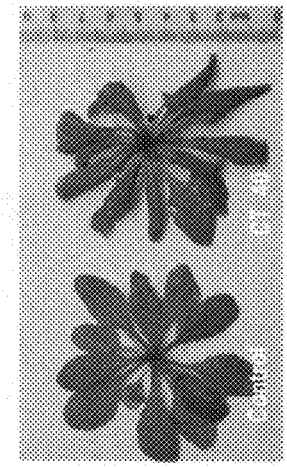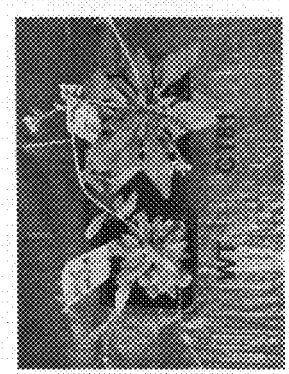

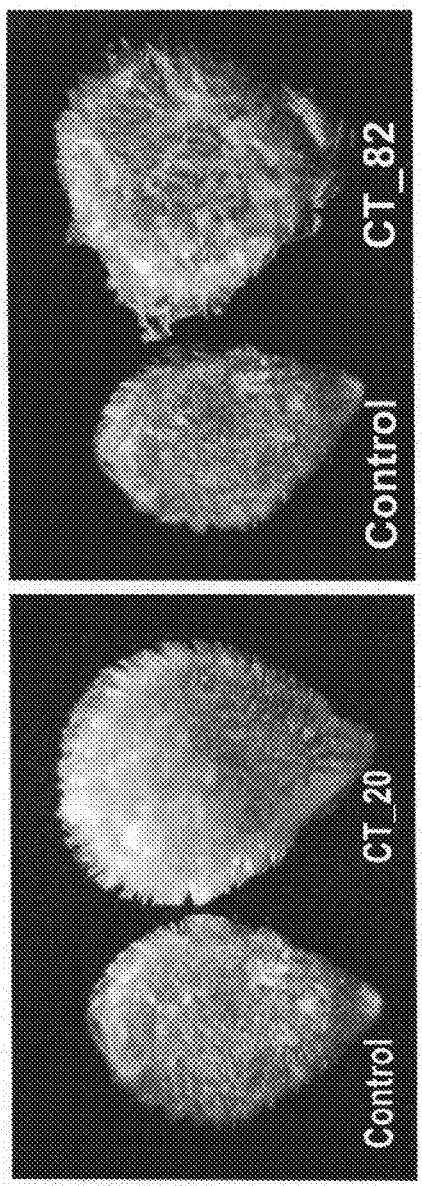
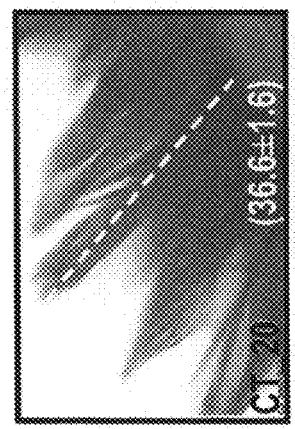
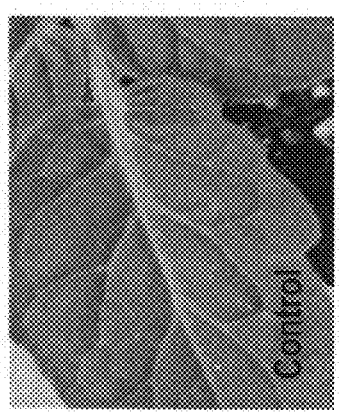
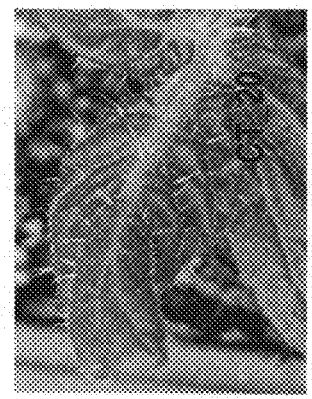
Fig. 6a  Fig. 6b  Fig. 6c  Fig. 6d  Fig. 6e  Fig. 6f

POLYNUCLEOTIDES AND POLYPEPTIDES INVOLVED IN PLANT FIBER DEVELOPMENT AND METHODS OF USING SAME

RELATED APPLICATIONS

This Application is a National Phase of PCT Patent Application No. PCT/IL2005/000627 having International Filing Date of Jun. 14, 2005, which claims the benefit of U.S. Provisional Patent Application No. 60/578,833 filed on Jun. 14, 2004. The contents of the above Applications are all incorporated herein by reference.

FIELD AND BACKGROUND OF THE INVENTION

The present invention relates to polynucleotides and polypeptides involved in plant-fiber development and methods of using same.

The present invention relates to a novel computational approach that utilizes comparative genomics to identify genes which play a role in fiber development.

Cotton and cotton by-products provide raw materials that are used to produce a wealth of consumer-based products in addition to textiles including cotton foodstuffs, livestock feed, fertilizer and paper. The production, marketing, consumption and trade of cotton-based products generate an excess of $100 billion annually in the U.S. alone, making cotton the number one value-added crop.

It is estimated that the use of cotton as a fiber by humans dates back 7000 years in Central America and 5000 years in India. Even with the growth of synthetic fibers in the last 50 years, cotton still accounts for approximately 50% of the world's textile fiber [Agrow Reports, Global Seed markets DS208, October 2000].

Even though 90% of cotton's value as a crop resides in the fiber (lint), yield and fiber quality has declined, especially over the last decade [Meredith (2000), Proc. World Cotton Research Conference II, Athens, Greece pp. 97-101]. This decline has been attributed to general erosion in genetic diversity of cotton varieties, and an increased vulnerability of the crop to environmental conditions [Bowman et al., Crop Sci. 36:577-581 (1996); Meredith, supra].

There are many varieties of cotton plant, from which cotton fibers with a range of characteristics can be obtained and used for various applications. Cotton fibers may be characterized according to a variety of properties, some of which are considered highly desirable within the textile industry for the production of increasingly high quality products and optimal exploitation of modern spinning technologies. Commercially desirable properties include length, length uniformity, fineness, maturity ratio, decreased fuzz fiber production, micronaire, bundle strength, and single fiber strength. Much effort has been put into the improvement of the characteristics of cotton fibers mainly focusing on fiber length and fiber fineness. In particular, there is a great demand for cotton fibers of specific lengths.

Methods for improving the characteristics or yield of cotton fibers can be classified into the following three categories:

1. Variety Improvement by Cross Breeding

This method has been utilized most widely so far. At present, almost all the cultivated varieties of cotton plant are bred by this method. However, improvement of cotton fiber yield using traditional breeding is relatively slow and inefficient and the degree of variability which can be achieved is limited.

2. Treatment with Plant Hormones

Plant hormones such as auxin, gibberellin, cytokinin and ethylene have been widely used in field crops or horticultural products. The influence of plant hormones, particularly gibberellin, auxin and brassinolide, on the fiber characteristics of cotton plants is known [e.g. U.S. Pat. No. 5,880,110 produces cotton fibers with improved fiber characteristics by treatment with brassinosteroids]. However, no measurable effect has been documented, making practical use of these hormones on a large scale highly unlikely.

3. Variety Improvement by Genetic Engineering:

The broad acceptance of genetically engineered cotton in the leading producing countries and the fact that it is a non-food crop make it an attractive candidate for genetic engineering for improvement of fiber yield and/or quality.

In recent years, remarkable progress has been made in plant genetic engineering, as a result several cases of successful variety improvement of commercially important crop plants have been reported (e.g., cotton, soybean, corn, canola, tomato). For example, methods of improving insect resistance by the introduction of a gene coding for BT toxin (i.e., insecticidal protein toxin produced by *Bacillus thuringiensis*) in a cotton plant, have been developed and put to practical use. In addition, cotton plants with improved herbicide (Glyphosate) resistance have been genetically engineered by the introduction of a gene coding for 5-enol-pyruvil-shikimic acid 3-phosphate synthetase.

The availability and success of plant genetic engineering combined with the fact that cotton is an excellent candidate for genetic manipulation via recombinant techniques have led researchers to postulate that if a gene associated with an improved cotton fiber property could be identified, it could be up-regulated using recombinant techniques thus improving the characteristics or yield of cotton fibers. Conversely, if a gene associated with a decline in a cotton fiber property could be identified, it could be down-regulated using gene silencing methods. For this purpose, the mechanisms of fiber elongation and formation must be elucidated on the genetic level and genes closely associated with these mechanisms must be identified.

A cotton fiber is composed of a single cell that has differentiated from an epidermal cell of the seed coat, developing through four stages, i.e., initiation, elongation, secondary cell wall thickening and maturation stages. More specifically, the elongation of a cotton fiber commences in the epidermal cell of the ovule immediately following flowering, after which the cotton fiber rapidly elongates for approximately 21 days. Fiber elongation is then terminated, and a secondary cell wall is formed and grown through maturation to become a mature cotton fiber.

Several candidate genes have been isolated which are associated with the elongation and formation of cotton fibers. For example, five genes from cotton plants have been identified that are specifically expressed at the cotton fiber elongation stage by differential screening method and differential display method, [U.S. Pat. No. 5,880,100 and U.S. patent application Ser. Nos. 08/580,545, 08/867,484 and 09/262,653].

WO0245485 describes methods and means to modulate fiber quality in fiber-producing plants, such as cotton, by modulating sucrose synthase (a sugar important for cell wall synthesis) activity and/or expression in such plants.

U.S. Pat. No. 6,472,588 and WO0117333 provide methods for increasing the quality of cotton fiber produced from a cotton plant by transformation with a DNA encoding sucrose phosphate synthase. The fiber qualities include strength, length, fiber maturity ratio, immature fiber content, fiber uniformity and micronaire.

WO9508914 discloses a fiber producing plant comprising in its genome a heterologous genetic construct. The genetic construct comprises a fiber-specific promoter and a coding sequence encoding a plant peroxidase, such as a cotton peroxidase.

WO9626639 provides methods whereby an ovary specific promoter sequence is utilized to express plant growth modifying hormones in cotton ovule tissue. The methods permit the modification of the characteristics of boll set in cotton plants and provide a mechanism for altering fiber quality characteristics such as fiber dimension and strength.

U.S. Pat. No. 5,981,834, U.S. Pat. No. 5,597,718, U.S. Pat. No. 5,620,882, U.S. Pat. No. 5,521,708 and U.S. Pat. No. 5,495,070 all disclose a method for genetically engineering a fiber-producing plant and the identification of cDNA clones useful for identifying fiber genes in cotton. The cDNA clones are useful in developing corresponding genomic clones from fiber producing plants to enable genetic engineering of cotton and other plants using these genes. Coding sequences from these isolated genes are used in sense or antisense orientation to alter the fiber characteristics of transgenic fiber producing plants.

U.S. patent applications U.S. 2002049999 and U.S. 2003074697 both disclose cotton plants of the genus Gossypium with improved cotton fiber characteristics. The cotton plant has an expression cassette containing a gene coding for an enzyme selected from the group consisting of endoxyloglucan transferase, catalase and peroxidase so that the gene is expressed in cotton fiber cells to improve the cotton fiber characteristics.

WO 01/40250 provides methods for improving cotton fiber quality by modulating transcription factor gene expression.

WO 96/40924 provides novel DNA constructs which may be used as molecular probes or alternatively inserted into a plant host to provide for modification of transcription of a DNA sequence of interest during various stages of cotton fiber development. The DNA constructs comprise a cotton fiber transcriptional initiation regulatory region associated with a gene, which is expressed in cotton fiber. Also provided is a novel cotton having a cotton fiber which has a natural color. The color was achieved by the introduction and expression in cotton fiber cell of a pigment gene construct.

EP0834566 provides a gene which controls the fiber formation mechanism in cotton plant and which can be used for industrially useful improvement.

However, beside Sucrose Synthase, there is no evidence to date that the expression of any particular gene plays an essential role in cotton fiber formation or enhanced fiber characteristics.

Thus, there remains a need for identifying other genes associated with fiber characteristics of cotton plants and a more thorough search for quality-related genes is required.

While reducing the present invention to practice the present inventors devised and employed a novel computational approach that utilizes comparative genomics to identify genes which play a pivotal role in fiber development. As demonstrated herein, expression of such genes correlates with fiber length and their overexpression is sufficient to modify tomato seed hair, an ultimate model for cotton fibers. These results suggest that polynucleotides of the present invention can be used for generating transgenic cotton plants which are characterized by fibers of desired length.

SUMMARY OF THE INVENTION

According to one aspect of the present invention there is provided an isolated polynucleotide comprising a nucleic acid sequence encoding a polypeptide having an amino acid sequence at least 80% homologous to SEQ ID NO: 26, 106, 107, 109, 110, 112, 114, 115, 118, 119, 122, 123, 124, 126, 95 or 96, wherein the polypeptide is capable of regulating cotton fiber development.

According to further features in preferred embodiments of the invention described below, the nucleic acid sequence is selected from the group consisting of SEQ ID NOs. 1, 2, 4, 5, 7, 9, 10, 16, 17, 20, 21, 22, 24, 25, 27 and 13.

According to still further features in the described preferred embodiments the polypeptide is as set forth in SEQ ID NO. 26, 106, 107, 109, 110, 112, 114, 115, 118, 119, 122, 123, 124, 126, 95 or 96.

According to still further features in the described preferred embodiments the amino acid sequence is as set forth in SEQ ID NO. 26, 106, 107, 109, 110, 112, 114, 115, 118, 119, 122, 123, 124, 126, 95 or 96.

According to still further features in the described preferred embodiments the cotton fiber development comprises fiber formation.

According to still further features in the described preferred embodiments the cotton fiber development comprises fiber elongation.

According to another aspect of the present invention there is provided an isolated polynucleotide comprising a nucleic acid sequence at least 80% identical to SEQ ID NO: 85 or 91, wherein the nucleic acid sequence is capable of regulating expression of at least one polynucleotide sequence operably linked thereto in an ovule endothelial cell.

According to still further features in the described preferred embodiments the ovule endothelial cell is of a plant fiber or a trichome.

According to yet another aspect of the present invention there is provided an oligonucleotide capable of specifically hybridizing to the isolated polynucleotide.

According to another aspect of the present invention there is provided a nucleic acid construct comprising the isolated polynucleotide.

According to still further features in the described preferred embodiments the nucleic acid construct further comprising at least one cis-acting regulatory element operably linked to the isolated polynucleotide.

According to still further features in the described preferred embodiments the polynucleotide sequence is selected from the group consisting of SEQ ID NOs: 1, 2, 4, 5, 7, 9, 10, 16, 17, 20, 21, 22, 24, 25, 27 and 13.

According to still further features in the described preferred embodiments the cis-acting regulatory element is as set forth in SEQ ID NO: 74, 75, 85 or 91 or functional equivalents thereof.

According to an additional aspect of the present invention there is provided a transgenic cell comprising the nucleic acid construct.

According to yet an additional aspect of the present invention there is provided a transgenic plant comprising the nucleic acid construct.

According to yet another aspect of the present invention there is provided a method of improving fiber quality and/or yield of a fiber producing plant, the method comprising regulating an expression level or activity of at least one polynucleotide encoding a polypeptide having an amino acid sequence at least 80% homologous to SEQ ID NO: 26, 106, 107, 109, 110, 112, 114, 115, 118, 119, 122, 123, 124, 126, 95 or 96 in the fiber producing plant, thereby improving the quality and/or yield of the fiber producing plant.

According to still further features in the described preferred embodiments the quality of the fiber producing plant comprises at least one parameter selected from the group consisting of fiber length, fiber strength, fiber weight per unit length, maturity ratio, uniformity and micronaire.

According to still further features in the described preferred embodiments the regulating expression or activity of the at least one polynucleotide is up-regulating.

According to still further features in the described preferred embodiments the up-regulating is effected by introducing into the cotton the nucleic acid construct.

According to still further features in the described preferred embodiments the regulating expression or activity of the at least one polynucleotide is down-regulating.

According to still further features in the described preferred embodiments the down-regulating is effected by gene silencing.

According to still further features in the described preferred embodiments the gene silencing is effected by introducing into the cotton the oligonucleotide.

According to still further features in the described preferred embodiments the fiber producing plant is selected from the group consisting of cotton, silk cotton tree (Kapok, *Ceiba pentandra*), desert willow, creosote bush, winterfat, balsa, ramie, kenaf, hemp, roselle, jute, sisal abaca and flax.

According to still an additional aspect of the present invention there is provided a method of increasing a biomass of a plant, the method comprising regulating an expression level or activity of at least one polynucleotide encoding a polypeptide having an amino acid sequence at least 80% homologous to SEQ ID NO: 26, 106, 107, 109, 110, 112, 114, 115, 118, 119, 122, 123, 124, 126, 95 or 96 in the plant, thereby increasing the biomass of the plant.

According to still further features in the described preferred embodiments the plant is a monocot plant.

According to still further features in the described preferred embodiments the plant is a dicot plant.

According to a further aspect of the present invention there is provided a method of identifying genes which are involved in cotton fiber development, the method comprising:
 (a) providing expressed nucleic acid sequences derived from cotton fibers;
 (b) providing expressed nucleic acid sequences derived from an ovule tissue;
 (c) computationally assembling the expressed nucleic acid sequences of (a) and (b) to generate clusters; and
 (d) identifying clusters of the clusters which comprise expressed nucleic acid sequences of (a) and (b), thereby identifying genes which are involved in cotton fiber development.

According to still further features in the described preferred embodiments the method further comprising identifying genes which are differentially expressed in the cotton fiber following (d).

According to still further features in the described preferred embodiments the differentially expressed comprises:
 (a) specific expression; and/or
 (b) change in expression over fiber development.

According to yet an additional aspect of the present invention there is provided a method of producing an insect resistant plant, comprising regulating an expression level or activity of at least one polynucleotide encoding a polypeptide having an amino acid sequence at least 80% homologous to SEQ ID NO: 26, 106, 107, 109, 110, 112, 114, 115, 118, 119, 122, 123, 124, 126, 95 or 96 in a trichome of the plant, thereby producing the insect resistant plant.

According to still an additional aspect of the present invention there is provided a method of producing cotton fibers, the method comprising:

(a) generating a transgenic cotton plant expressing at least one polypeptide having an amino acid sequence at least 80% homologous to SEQ ID NO: 26, 106, 107, 109, 110, 112, 114, 115, 118, 119, 122, 123, 124, 126, 95 or 96; and
 (b) harvesting the fibers of the transgenic cotton plant, thereby producing the cotton fibers.

The present invention successfully addresses the shortcomings of the presently known configurations by providing genes involved in cotton fiber development and methods of using same.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is an illustration depicting the bioinformatic methodology of the present invention effected to identify genes which may be used to improve cotton fiber yield and quality.

FIGS. 2a-d are bar graphs showing expression patterns of fiber specific genes (CT_11 FIG. 2b), elongation associated genes (CT_1, FIG. 2c) and initiation associated genes (CT_22, FIG. 2d).

Figure 3:
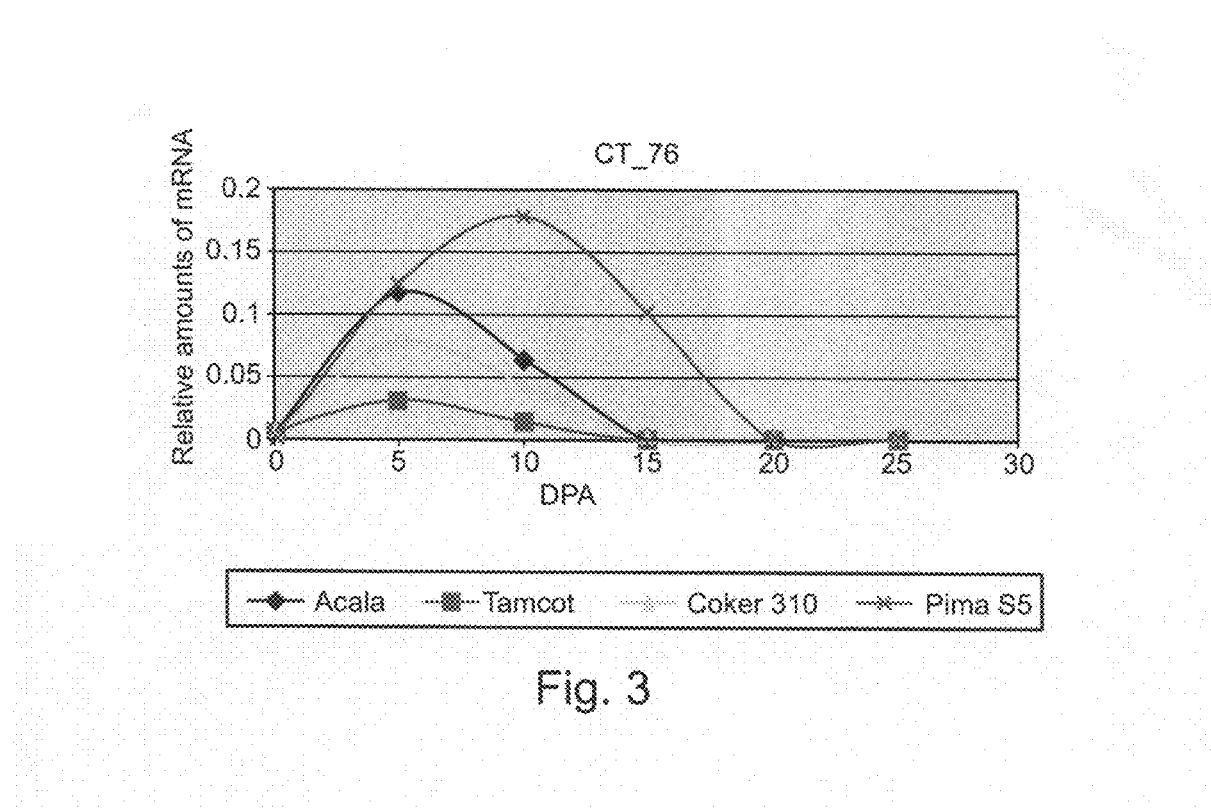

FIG. 3 is a graph depicting expression of CT_76 in varieties of cotton (*G. hirsutum* var Tamcot, Coker and Acala, and *G. barbadense* var Pima S5) plants, as determined by RT-PCR.

Figure 4:
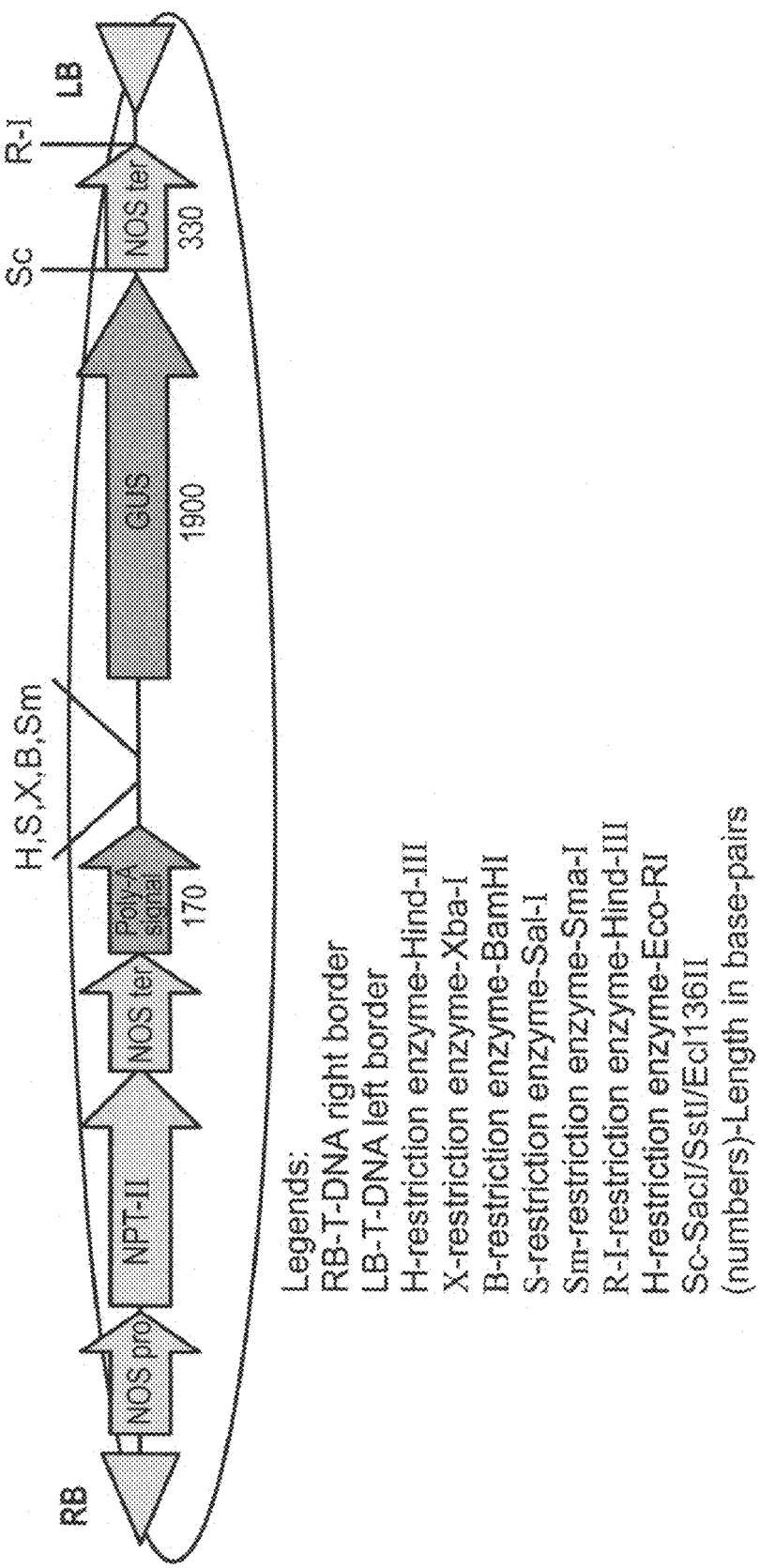

FIG. 4 is a schematic illustration of the pPi binary plasmid.

FIGS. 5a-l are photographs of wild-type and transgenic *arabidopsis* plants over-expressing genes of the present invention. FIG. 5a shows two week old rosette of wt plants; FIG. 5b shows two week old rosette of CT11 over-expressing *arabidopsis* plants; FIG. 5c shows two week old roots of CT11; FIG. 5d shows three week old wild type *arabidopsis*; FIG. 5e shows three week old CT_20; FIG. 5f shows three week old CT_22; FIG. 5g shows 30 days old rosettes of wt and CT_9; FIG. 5h shows 30 days inflorescence of wt and CT_9; FIG. 5i shows two week old roots of CT9; FIG. 5j shows 30 days old rosettes of wt and CT_40; FIG. 5k shows rosette of 5 week old wt and CT81 over-expressing plants; FIG. 5*l* shows a leaf of wt and CT81 over-expressing *arabidopsis* plants;

FIGS. 6*a-e* are photographs depicting wild-type and transgenic tomato plants over-expressing CT_20. FIG. 6*a* shows a leaf of wild-type plant; FIG. 6*b* shows a leaf of CT_20 transgenic tomato; FIG. 6*c* shows seed hairs of WT and CT_20 over-expressing tomato plants; FIG. 6*d* shows section of a wt tomato seed; FIG. 6*e* shows section of a CT_20 over-expressing tomato seed; FIG. 6*f* seed hairs of WT and CT_82.

Figures 7A, 7B:
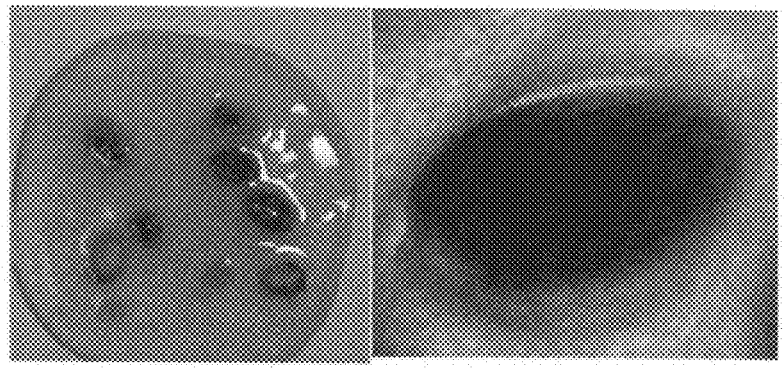
Figure 8A:
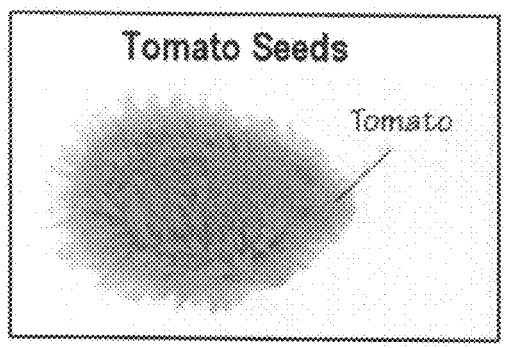
Figure 8B:
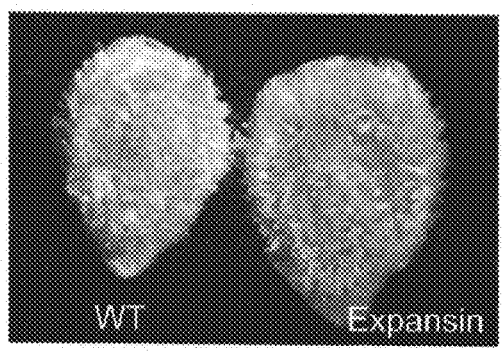

FIGS. 7*a-b* are photographs depicting transgenic tomato plants over-expressing GUS under the expression of the CT_2 promoter. FIG. 7*a* is a cut through transgenic tomato fruit, over-expressing GUS under CT2 promoter in the mature green stage (×5 magnification). FIG. 7*b* similar to FIG. 7*a* showing ×25 magnification;

FIGS. 8*a-b* are photographs depicting various magnifications of wild-type and transgenic tomato fruits or tomato seeds. FIG. 8*a* is a single wild type tomato seed covered with seed hairs ×10 magnification; FIG. 8*b* shows tomato seed over expressing expansin under 35S (×10 magnification).

DESCRIPTION OF THE PREFERRED EMBODIMENTS

The present invention is of polypeptides and polynucleotides encoding same which are involved in plant fiber development and which can be used to improve fiber quality and/or yield/biomass of a fiber producing plant.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Cotton and cotton by-products provide raw materials that are used to produce a wealth of consumer-based products; in addition to textiles, cotton is used to produce foodstuffs, livestock feed, fertilizer and paper. The production, marketing, consumption and trade of cotton-based products generate an excess of $100 billion annually in the U.S. alone, making cotton the number one value-added crop.

Over the past decade cotton fiber production has sharply declined prompting cotton growers and researchers to look for approaches, which can be used to improve fiber yield and quality.

Increasing fiber quality and/or yield under diverse environmental conditions will increase the profitability of cotton crop production and provide a new spectrum of material properties for exploitation by the processing industries.

While reducing the present invention to practice, the present inventors have configured a novel computational approach that utilizes comparative genomics to identify genes which play a role in fiber development. Genes identified using this approach may be successfully used for generating transgenic plants which are featured by fibers of desired properties.

Thus, according to one aspect of the present invention there is provided a method of identifying genes which are involved in cotton fiber development.

As used herein the term "cotton" refers to a wild-type, a cultivated variety (e.g., hybrid) or a transgenic cotton (*Gossypium*) plant.

As used herein the phrase "fiber development" refers to the development of the hair of the cotton seed.

As used herein the term "development" when used in context of cotton fibers refers to initiation of the fiber and/or elongation thereof, as well as to the fiber secondary cell wall thickening and maturation.

The method according to this aspect of the present invention is effected by:

(a) providing expressed nucleic acid sequences derived from cotton fibers;

(b) providing expressed nucleic acid sequences derived from an ovule tissue (i.e., a tissue developed from an ovary of a seed plant. Examples include, but are not limited to, carpels, seed coat, embryo, endosperm);

(c) computationally assembling the expressed nucleic acid sequences of (a) and (b) to generate clusters; and (d) identifying clusters of said clusters which comprise expressed nucleic acid sequences of (a) and (b), thereby identifying genes which are involved in cotton fiber development.

Expressed nucleic acid sequences used as a potential source for identifying genes involved in cotton fiber development according to this aspect of the present invention are preferably libraries of expressed messenger RNA [i.e., expressed sequence tags (EST), cDNA clones, contigs, pre-mRNA, etc.] obtained from tissue or cell-line preparations which can include genomic and/or cDNA sequence.

Expressed nucleic acid sequences, according to this aspect of the present invention can be retrieved from pre-existing publicly available databases (see Example 1 of the Examples section which follows or private databases).

Alternatively, the expressed nucleic acid sequences utilized by the present invention can be generated from sequence libraries (e.g., cDNA libraries, EST libraries, mRNA libraries and others).

cDNA libraries are suitable sources for expressed sequence information.

Generating a sequence database in such a case is typically effected by tissue or cell sample preparation, RNA isolation, cDNA library construction and sequencing.

It will be appreciated that such cDNA libraries can be constructed from RNA isolated from whole plant, specific tissues, or cell populations.

Once expressed sequence data is obtained from both cotton fibers and an ovule tissue, sequences may be clustered to form contigs. See Example 1 of the Examples section which follows Such contigs are then assembled to identify homologous sequences (of cotton fibers and ovule tissue) present in the same cluster, such contigs are considered to be involved in cotton fiber development.

A number of commonly used computer software fragment read assemblers capable of forming clusters of expressed sequences are commercially available. These packages include but are not limited to, The TIGR Assembler [Sutton G. et al. (1995) Genome Science and Technology 1:9-19], GAP [Bonfield J K. et al. (1995) Nucleic Acids Res. 23:4992-4999], CAP2 [Huang X. et al. (1996) Genomics 33:21-31], The Genome Construction Manager [Laurence C B. Et al. (1994) Genomics 23:192-201], Bio Image Sequence Assembly Manager, SeqMan [Swindell S R. and Plasterer J N. (1997) Methods Mol. Biol. 70:75-89], LEADS and GenCarta (Compugen Ltd. Israel).

Once genes which are involved in cotton fiber development are identified their pattern of expression can be analyzed as described in Example 2 of the Examples section which follows, to thereby identify genes which are differentially expressed in the cotton fiber (i.e., specific expression) or during cotton fiber development (i.e., change in expression during cotton fiber development).

Methods of identifying differentially expressed genes are well known in the art.

Using the above methodology, the present inventors were able to successfully identify genes which are involved in cotton fiber development.

As is illustrated in the Examples section which follows genes identified using the teachings of the present invention can be classified into 6 functional categories according to their sequence homology to known proteins and enzymes (Table 3, below). The Two genes were classified into a cell fate commitment category: homologous to the MYB transcription factor and to GL3 which are known to be involved in trichome development in *arabidopsis*. The expression pattern of both genes and the phenotype of CT20 transgene both in *arabidopsis* and tomato T1 plants support their involvement mainly in the initiation phase. Two other genes (Table 3, above) are transcription factors from the MYB and MADS BOX families. Many studies demonstrated the function of these two transcription factor families as homeotic genes with key role in different developmental processes, among them are trichome and fiber morphogenesis (Suo. J. et. al. 2003, Ferrario S et. al. 2004). Their role in early stages of fiber development is supported also by their RNA expression pattern, which, is induced before, and during the day of anthesis. One gene belongs to the pathways of starch and sucrose metabolism. A recent work demonstrates that another gene (SUS), which, belongs to this pathway, is a limiting factor in both fiber initiation and development. Another gene (Table 3, below) is classified as lipid transport whose RNA expression is highly induced during early fiber elongation stage fit to the fact that lipids are key components in fiber formation. Several genes (Table 3, below) were classified either as genes involved in desiccation, salinity response stimulated by abscisic acid and genes involved in electron transfer. Out of them 3 genes were selected by RNA expression pattern to be induced in the elongation stage.

In view of the above and together with the experimental results which correlate gene expression with fiber length, it is suggested that genes of the present invention can be used to generate fiber producing plants with commercially desired fiber quality.

Thus, the present invention encompasses polynucleotides identified using the present methodology and their encoded polypeptide as well as functional equivalents of the polypeptides identified herein (i.e., polypeptides which are capable of regulating cotton fiber development, as can be determined according to the assays described in the Examples section which follows) and their coding sequences. Such functional equivalents can be at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 75%, at least about 75%, at least about 75%, at least about 75%, say 100% homologous to SEQ ID NO: 106, 107, 108, 109, 110, 111, 112, 113, 114, 115, 116, 117, 118, 119, 120, 121, 122, 123, 124, 125, 126, 95 or 96.

Polynucleotides encoding functional equivalents can be at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 75%, at least about 75%, at least about 75%, at least about 75%, say 100% identical to SEQ ID NO: 1, 2, 3, 4, 5, 6, 7, 8, 9, 10, 11, 12, 16, 17, 18, 19, 20, 21, 22, 23, 24, 25 or 27.

Homology (e.g., percent homology) can be determined using any homology comparison software, including for example, the BlastP software of the National Center of Biotechnology Information (NCBI) such as by using default parameters.

Identity (e.g., percent homology) can be determined using any homology comparison software, including for example, the BlastN software of the National Center of Biotechnology Information (NCBI) such as by using default parameters.

As used herein the phrase "an isolated polynucleotide" refers to a single or double stranded nucleic acid sequences which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

According to a preferred embodiment of this aspect of the present invention, the nucleic acid sequence is as set forth in SEQ ID NO: 1, 2, 3, 4, 5, 6, 7, 8, 9, 10, 12, 13, 14, 15, 16, 17, 19, 21, 22, 23, 24, 25 or 26.

According to another preferred embodiment of this aspect of the present invention, the isolated polynucleotide is as set forth in SEQ ID NO: 1, 2, 3, 4, 5, 6, 7, 8, 9, 10, 11, 12, 16, 17, 18, 19, 20, 21, 22, 23, 24, 25 or 27.

According to yet another preferred embodiment of this aspect of the present invention, the polypeptide is as set forth in SEQ ID NO: 106, 107, 108, 109, 110, 111, 112, 113, 114, 115, 116, 117, 118, 119, 120, 121, 122, 123, 124, 125, 126, 95 or 96.

According to still another preferred embodiment of this aspect of the present invention, the amino acid sequence is as set forth in SEQ ID NO: 106, 107, 108, 109, 110, 111, 112, 113, 114, 115, 116, 117, 118, 119, 120, 121, 122, 123, 124, 125, 126, 95 or 96.

The isolated polynucleotides of this aspect of the present invention can also be qualified using a hybridization assay by incubating the isolated polynucleotides described above in the presence of oligonucleotide probe or primer under moderate to stringent hybridization conditions.

Moderate to stringent hybridization conditions are characterized by a hybridization solution such as containing 10% dextrane sulfate, 1 M NaCl, 1% SDS and 5×10⁶ cpm $^{32}$P labeled probe, at 65° C., with a final wash solution of 0.2× SSC and 0.1% SDS and final wash at 65° C. and whereas moderate hybridization is effected using a hybridization solution containing 10% dextrane sulfate, 1 M NaCl, 1% SDS and 5×10⁶ cpm $^{32}$P labeled probe, at 65° C., with a final wash solution of 1×SSC and 0.1% SDS and final wash at 50° C.

Thus, the present invention encompasses nucleic acid sequences described hereinabove; fragments thereof, sequences hybridizable therewith, sequences homologous thereto, sequences encoding similar polypeptides with different codon usage, altered sequences characterized by mutations, such as deletion, insertion or substitution of one or more nucleotides, either naturally occurring or man induced, either randomly or in a targeted fashion.

Since the polynucleotide sequences of the present invention encode previously unidentified polypeptides, the present invention also encompasses novel polypeptides or portions thereof, which are encoded by the isolated polynucleotides and respective nucleic acid fragments thereof described hereinabove.

Thus, the present invention also encompasses polypeptides encoded by the polynucleotide sequences of the present invention. The amino acid sequences of these novel polypeptides are set forth in SEQ ID NO: 26, 106, 107, 109, 110, 112, 114, 115, 118, 119, 122, 123, 124, 126, 95 or 96.

The present invention also encompasses homologues of these polypeptides, such homologues can be at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, or more say 100% homologous to SEQ ID NO: 26, 106, 107, 109, 110, 112, 114, 115, 118, 119, 122, 123, 124, 126, 95 or 96.

The present invention also encompasses fragments of the above described polypeptides and polypeptides having mutations, such as deletions, insertions or substitutions of one or more amino acids, either naturally occurring or man induced, either randomly or in a targeted fashion.

The ability of polynucleotides of the present invention and their products to regulate cotton fiber development can be determined directly on at least one structural parameter of a cotton fiber such as fiber length or fiber finesse, or fiber growth rate (further described hereinbelow). However cotton fiber development can also determined indirectly such as by plant model systems for cotton fiber development. For example, its is well established that trichome cells and root hairs share common characteristics with cotton fiber cells, and as such can be used as model systems for cotton fiber development [Reviewed in Wagner. G. J. et. al. (2004)], as demonstrated in details in Example 12 of the Examples section which follows.

By analyzing expression profiles, the present inventors were able to determine the involvement of the biomolecular sequences (i.e., polynucleotides and polypeptides) of the present invention in fiber initiation and/or elongation. These results were further substantiated by establishing a correlation between gene expression and fiber length (see Example 7).

These results suggest that biomolecular sequences of the present invention (e.g., polynucleotides, polypeptides, promoters, oligonucleotides, antibodies, also referred to herein as agents) can be used to improve fiber quality and/or yield of a fiber producing plant.

Thus, according to yet another aspect of the present invention there is provided a method of improving fiber quality and/or yield of a fiber producing plant.

The method of this aspect of the present invention is effected by regulating an expression level or activity of at least one polynucleotide or polypeptide of the present invention (described hereinabove) in the fiber producing plant, thereby improving the quality and/or yield of the fiber producing plant.

As used herein the phrase "fiber producing plant" refers to plants that share the common feature of having an elongated shape and abundant cellulose in thick cell walls, typically termed as secondary walls. Such walls may or may not be lignified, and the protoplast of such cells may or may be viable at maturity. Such fibers have many industrial uses, for example in lumber and manufactured wood products, paper, textiles, sacking and boxing material, cordage, brushes and brooms, filling and stuffing, caulking, reinforcement of other materials, and manufacture of cellulose derivatives.

According to a preferred embodiment of this aspect of the present invention the fiber producing plant is cotton.

The term "fiber" is usually inclusive of thick-walled conducting cells such as vessels and tracheids and to fibrillar aggregates of many individual fiber cells. Hence, the term "fiber" refers to (a) thick-walled conducting and non-conducting cells of the xylem; (b) fibers of extraxylary origin, including those from phloem, bark, ground tissue, and epidermis; and (c) fibers from stems, leaves, roots, seeds, and flowers or inflorescences (such as those of Sorghum vulgare used in the manufacture of brushes and brooms).

Example of fiber producing plants, include, but are not limited to, agricultural crops such as cotton, silk cotton tree (Kapok, Ceiba pentandra), desert willow, creosote bush, winterfat, balsa, kenaf, roselle, jute, sisal abaca, flax, corn, sugar cane, hemp, ramie, kapok, coir, bamboo, spanish moss and Agave spp. (e.g. sisal).

As used herein the phrase "fiber quality" refers to at least one fiber parameter which is agriculturally desired, or required in the fiber industry (further described hereinbelow). Examples of such parameters, include but are not limited to, fiber length, fiber strength, fiber fitness, fiber weight per unit length, maturity ratio and uniformity (further described hereinbelow.

Cotton fiber (lint) quality is typically measured according to fiber length, strength and fineness. Accordingly, the lint quality is considered higher when the fiber is longer, stronger and finer.

As used herein the phrase "fiber yield" refers to the amount or quantity of fibers produced from the fiber producing plant.

As used herein the term "improving" refers to at least about 5%, at least about 10%, at least about 15%, at least about 20%, at least about 30%, at least about 40%, at least about 50%, change in fiber quality/yield as compared to a native plant (i.e., not modified with the biomolecular sequences of the present invention).

As used herein the term "regulating" refers to up regulating, down regulating or a combination thereof. For example, when an increase in fiber number is desired the present invention can be effected by upregulating at least one polynucleotide of the present invention, which is involved in fiber initiation (e.g., SEQ ID NOs: 4, 10, 9, 12, 16 and 25). Alternatively, when short fibers are desired such as for example, in corn, then the present invention is effected by down regulating at least one polynucleotide of the present invention which is involved in fiber elongation (e.g., SEQ ID NOs. 1, 2, 3, 5, 6, 7, 17, 18, 19, 20, 21, 22, 23, 24 and 27). Alternatively, the present invention can be effected by upregulating expression of at least one polynucleotide (such as involved in fiber elongation) and down regulating at least one polynucleotide (such as involved in fiber initiation) of the polynucleotides of the present invention. In this manner it is feasible to obtain a fiber producing plant with improved fiber yield of each of short length.

Up regulating an expression level of at least one of the polynucleotides of the present invention can be effected at the genomic level (e.g., activation of transcription by means of promoters, enhancers, or other regulatory elements), at the transcript level, or at the protein level.

Following is a non-comprehensive list of agents capable of upregulating the expression level and/or activity of the biomolceular sequences (i.e., nucleic acid or protein sequences) of the present invention.

An agent capable of upregulating expression of a polynucleotide of interest may be an exogenous polynucleotide sequence designed and constructed to express at least a functional portion thereof (e.g., improving fiber yield/quality, increasing biomass etc.). Accordingly, the exogenous polynucleotide sequence may be a DNA or RNA sequence encoding a polypeptide molecule, capable of improving fiber yield or quantity. Alternatively, the exogenous polynucleotide may be a cis-acting regulatory region (e.g., SEQ ID NO: 74, 75, 85, 88 or 91) which may be introduced into the plant to increase expression of any polynucleotide which is involved in fiber development (e.g., sucrose phosphate synthase, as described in U.S. Pat. No. 6,472,588).

To express exogenous polynucleotides in plant cells, a polynucleotide sequence of the present invention is preferably ligated into a nucleic acid construct suitable for plant cell expression. Such a nucleic acid construct includes a cis-acting regulatory region such as a promoter sequence for directing transcription of the polynucleotide sequence in the cell in a constitutive or inducible manner. The promoter may be homologous or heterologous to the transformed plant/cell.

Preferred promoter sequences which can be used in accordance with this aspect of the present invention are endothelial cell promoters.

For example, promoter sequences of each of the polynucleotide sequences of the present invention may be preferably used in the nucleic acid constructs of the present invention.

According to a preferred embodiment of this aspect of the present invention the promoter is at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to SEQ ID NO. 85 or 91, which is capable of regulating expression of at least one polynucleotide sequence operably linked thereto in an ovule endothelial cell (i.e., capable of exerting a regulatory effect on the coding sequence linked thereto).

As is clearly illustrated in the Examples section which follows, such promoter sequences are capable of regulating expression of a coding nucleic acid sequence (e.g., GUS) operably linked thereto.

Other examples of cotton fiber-enhanced promoters include those of the cotton fiber-expressed genes E6 (John et al., Plant Mol. Biol., 30:297-306 (1996) and John et al., Proc. Natl. Acad. Sci., 93:12768-12773 (1996) e), H6 (John et al., Plant Physiol., 108:669-676, (1995)), FbL2A (Rinehart et al., Plant Physiol., 112:1331-1341 (1996) and John et al, Proc. Natl. Acad. Sci. USA, 93:12768-12773 (1996)), rac (Delmer et al., Mol. Gen. Genet., 248:43-51 (1995)); CelA (Pear et al., Proc. Natl. Acad. Sci. USA, 93:12637-12642 (1996)); CAP (Kawai et al., Plant Cell Physiol. 39:1380-1383 (1998)); ACP (Song et al., Biochim. Biophys. Acta 1351:305-312 (1997); and LTP (Ma et al., Biochim. Biophys. Acta 1344:111-114 (1997)). Other cotton fiber specific promoters are disclosed in U.S. Pat. No. 5,495,070.

Other promoters which can be used in accordance with this aspect of the present invention are those that ensure expression only in specified organs, such as the leaf, root, tuber, seed, stem, flower or specified cell types such as parenchyma, epidermal, trichome or vascular cells.

Preferred promoters for enhancing expression in trichome cells are disclosed in WO 2004/111183, to Evogene Ltd.

Preferred promoters enhancing expression in vascular tissue include the CAD 2 promoter (Samaj et al., Planta, 204:437-443 (1998)), the Pt4C11 promoter (Hu et al., Proc. Natl. Acad. Sci. USA, 95:5407-5412 (1998)), the C4H promoter (Meyer et al., Proc. Natl. Acad. Sci. USA, 95:6619-6623 (1998)), the PtX3H6 and PtX14A9 promoters (Loopstra et al., Plant Mol. Biol., 27:277-291 (1995)), the RolC promoter (Graham, Plant Mol. Biol., 33:729-735 (1997)), the Hvhsp17 promoter (Raho et al., J. Expt. Bot., 47:1587-1594 (1996)), and the COMT promoter (Capellades et al., Plant Mol. Biol., 31:307-322 (1996)).

Preferred promoters enhancing expression in stem tissue include pith promoters (Datta, Theor. Appl. Genet., 97:20-30 (1998) and Ohta et al., Mol. Gen. Genet., 225:369-378 (1991)), and the anionic peroxidase promoter (Klotz et al., Plant Mol. Biol., 36:509-520 (1998)). Preferred promoters enhancing expression in phloem, cortex and cork, but not xylem or pith, include the Psam-1 promoter (Mijnsbrugge et al., Plant and Cell Physiol., 37:1108-1115 (1996)).

Preferred promoters enhancing expression in seeds include the phas promoter (Geest et al., Plant Mol. Biol. 32:579-588 (1996)); the GluB-1 promoter (Takaiwa et al., Plant Mol. Biol. 30:1207-1221 (1996)); the gamma-zein promoter (Torrent et al. Plant Mol. Biol. 34:139-149 (1997)), and the oleosin promoter (Sarmiento et al., The Plant Journal 11:783-796 (1997)).

Other promoter sequences which mediate constitutive, inducible, tissue-specific or developmental stage-specific expression are disclosed in WO 2004/081173 to Evogene Ltd.

Truncated or synthetic promoters including specific nucleotide regions conferring tissue-enhanced expression may also be used, as exemplified by identification of regulatory elements within larger promoters conferring xylem-enhanced expression (Seguin et al., Plant Mol. Biol., 35:281-291 (1997); Torres-Schumann et al., The Plant Journal, 9:283-296 (1996); and Leyva et al., The Plant Cell, 4:263-271 (1992)).

The nucleic acid construct can be, for example, a plasmid, a bacmid, a phagemid, a cosmid, a phage, a virus or an artificial chromosome. Preferably, the nucleic acid construct of the present invention is a plasmid vector, more preferably a binary vector.

The phrase "binary vector" refers to an expression vector which carries a modified T-region from Ti plasmid, enable to be multiplied both in *E. coli* and in *Agrobacterium* cells, and usually comprising reporter gene(s) for plant transformation between the two boarder regions. A binary vector suitable for the present invention includes pBI2113, pBI121, pGA482, pGAH, pBIG, pBI101 (Clonetech), pPI (see Example 5 of the Examples section which follows) or modifications thereof.

The nucleic acid construct of the present invention can be utilized to transform a host cell (e.g., bacterial, plant) or plant.

As used herein, the terms "transgenic" or "transformed" are used interchangeably referring to a cell or a plant into which cloned genetic material has been transferred.

In stable transformation, the nucleic acid molecule of the present invention is integrated into the plant genome, and as such it represents a stable and inherited trait. In transient transformation, the nucleic acid molecule is expressed by the cell transformed but not integrated into the genome, and as such represents a transient trait.

There are various methods of introducing foreign genes into both monocotyledonous and dicotyledonous plants (Potrykus, I. (1991). Annu Rev Plant Physiol Plant Mol Biol 42, 205-225; Shimamoto, K. et al. (1989). Fertile transgenic rice plants regenerated from transformed protoplasts. Nature (1989) 338, 274-276).

The principal methods of the stable integration of exogenous DNA into plant genomic DNA includes two main approaches:

(i) *Agrobacterium*-mediated gene transfer. See: Klee, H. J. et al. (1987). Annu Rev Plant Physiol 38, 467-486; Klee, H. J. and Rogers, S. G. (1989). Cell Culture and Somatic Cell Genetics of Plants, Vol. 6, Molecular Biology of Plant Nuclear Genes, pp. 2-25, J. Schell and L. K. Vasil, eds., Academic Publishers, San Diego, Calif.; and Gatenby, A. A. (1989). Regulation and Expression of Plant Genes in Microorganisms, pp. 93-112, Plant Biotechnology, S. Kung and C. J. Arntzen, eds., Butterworth Publishers, Boston, Mass.

(ii) Direct DNA uptake. See, e.g.: Paszkowski, J. et al. (1989). Cell Culture and Somatic Cell Genetics of Plants, Vol. 6, Molecular Biology of Plant Nuclear Genes, pp. 52-68, J. Schell and L. K. Vasil, eds., Academic Publishers, San Diego, Calif.; and Toriyama, K. et al. (1988). Bio/Technol 6, 1072-1074 (methods for direct uptake of DNA into protoplasts). See also: Zhang et al. (1988). Plant Cell Rep 7, 379-384; and Fromm, M. E. et al. (1986). Stable transformation of maize after gene transfer by electroporation. Nature 319, 791-793 (DNA uptake induced by brief electric shock of plant cells). See also: Klein et al. (1988). Bio/Technology 6, 559-563; McCabe, D. E. et al. (1988). Stable transformation of soybean (*Glycine max*) by particle acceleration. Bio/Technology 6, 923-926; and Sanford, J. C. (1990). Biolistic plant transformation. Physiol Plant 79, 206-209 (DNA injection into plant cells or tissues by particle bombardment). See also: Neuhaus, J. M. et al. (1987). Theor Appl Genet. 75, 30-36; and Neuhaus, J. M. and Spangenberg, G. C. (1990). Physiol Plant 79, 213-217 (use of micropipette systems). See U.S. Pat. No. 5,464,765 (glass fibers or silicon carbide whisker transformation of cell cultures, embryos or callus tissue). See also: DeWet, J. M. J. et al. (1985). "Exogenous gene transfer in maize (*Zea mays*) using DNA-treated pollen," Experimental Manipulation of Ovule Tissue, G. P. Chapman et al., eds., Longman, New York-London, pp. 197-209; and Ohta, Y. (1986). High-Efficiency Genetic Transformation of Maize by a Mixture of Pollen and Exogenous DNA. Proc Natl Acad Sci USA 83, 715-719 (direct incubation of DNA with germinating pollen).

The *Agrobacterium*-mediated system includes the use of plasmid vectors that contain defined DNA segments which integrate into the plant genomic DNA. Methods of inoculation of the plant tissue vary depending upon the plant species and the *Agrobacterium* delivery system. A widely used approach is the leaf-disc procedure, which can be performed with any tissue explant that provides a good source for initiation of whole-plant differentiation (Horsch, R. B. et al. (1988). "Leaf disc transformation." Plant Molecular Biology Manual A5, 1-9, Kluwer Academic Publishers, Dordrecht). A supplementary approach employs the *Agrobacterium* delivery system in combination with vacuum infiltration. The *Agrobacterium* system is especially useful for in the creation of transgenic dicotyledenous plants.

There are various methods of direct DNA transfer into plant cells. In electroporation, the protoplasts are briefly exposed to a strong electric field, opening up mini-pores to allow DNA to enter. In microinjection, the DNA is mechanically injected directly into the cells using micropipettes. In microparticle bombardment, the DNA is adsorbed on microprojectiles such as magnesium sulfate crystals or tungsten particles, and the microprojectiles are physically accelerated into cells or plant tissues.

Following stable transformation, plant propagation occurs. The most common method of plant propagation is by seed. The disadvantage of regeneration by seed propagation, however, is the lack of uniformity in the crop due to heterozygosity, since seeds are produced by plants according to the genetic variances governed by Mendelian rules. In other words, each seed is genetically different and each will grow with its own specific traits. Therefore, it is preferred that the regeneration be effected such that the regenerated plant has identical traits and characteristics to those of the parent transgenic plant. The preferred method of regenerating a transformed plant is by micropropagation, which provides a rapid, consistent reproduction of the transformed plants.

Micropropagation is a process of growing second-generation plants from a single tissue sample excised from a selected parent plant or cultivar. This process permits the mass reproduction of plants having the preferred tissue and expressing a fusion protein. The newly generated plants are genetically identical to, and have all of the characteristics of, the original plant. Micropropagation allows for mass production of quality plant material in a short period of time and offers a rapid multiplication of selected cultivars with preservation of the characteristics of the original transgenic or transformed plant. The advantages of this method of plant cloning include the speed of plant multiplication and the quality and uniformity of the plants produced.

Micropropagation is a multi-stage procedure that requires alteration of culture medium or growth conditions between stages. The micropropagation process involves four basic stages: stage one, initial tissue culturing; stage two, tissue culture multiplication; stage three, differentiation and plant formation; and stage four, greenhouse culturing and hardening. During stage one, the tissue culture is established and certified contaminant-free. During stage two, the initial tissue culture is multiplied until a sufficient number of tissue samples are produced to meet production goals. During stage three, the newly grown tissue samples are divided and grown into individual plantlets. At stage four, the transformed plantlets are transferred to a greenhouse for hardening where the plants' tolerance to light is gradually increased so that they can continue to grow in the natural environment.

Although stable transformation is presently preferred, transient transformation of, for instance, leaf cells, meristematic cells, or the whole plant is also envisaged by the present invention.

Transient transformation can be effected by any of the direct DNA transfer methods described above or by viral infection using modified plant viruses.

Viruses that have been shown to be useful for the transformation of plant hosts include cauliflower mosaic virus (CaMV), tobacco mosaic virus (TMV), and baculovirus (BV). Transformation of plants using plant viruses is described in, for example: U.S. Pat. No. 4,855,237 (bean golden mosaic virus, BGMV); EPA 67,553 (TMV); Japanese Published Application No. 63-14693 (TMV); EPA 194,809

(BV); EPA 278,667 (BV); and Gluzman, Y. et al. (1988). Communications in Molecular Biology: Viral Vectors, Cold Spring Harbor Laboratory, New York, pp. 172-189. The use of pseudovirus particles in expressing foreign DNA in many hosts, including plants, is described in WO 87/06261.

Construction of plant RNA viruses for the introduction and expression of non-viral exogenous nucleic acid sequences in plants is demonstrated by the above references as well as by: Dawson, W. O. et al. (1989). A tobacco mosaic virus-hybrid expresses and loses an added gene. Virology 172, 285-292; French, R. et al. (1986) Science 231, 1294-1297; and Takamatsu, N. et al. (1990). Production of enkephalin in tobacco protoplasts using tobacco mosaic virus RNA vector. FEBS Lett 269, 73-76.

If the transforming virus is a DNA virus, one skilled in the art may make suitable modifications to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of the DNA will produce the coat protein, which will encapsidate the viral DNA. If the virus is an RNA virus, the virus is generally cloned as a cDNA and inserted into a plasmid. The plasmid is then used to make all of the plant genetic constructs. The RNA virus is then transcribed from the viral sequence of the plasmid, followed by translation of the viral genes to produce the coat proteins which encapsidate the viral RNA.

Construction of plant RNA viruses for the introduction and expression in plants of non-viral exogenous nucleic acid sequences, such as those included in the construct of the present invention, is demonstrated in the above references as well as in U.S. Pat. No. 5,316,931.

In one embodiment, there is provided for insertion a plant viral nucleic acid, comprising a deletion of the native coat protein coding sequence from the viral nucleic acid, a non-native (foreign) plant viral coat protein coding sequence, and a non-native promoter, preferably the subgenomic promoter of the non-native coat protein coding sequence, and capable of expression in the plant host, packaging of the recombinant plant viral nucleic acid, and ensuring a systemic infection of the host by the recombinant plant viral nucleic acid. Alternatively, the native coat protein coding sequence may be made non-transcribable by insertion of the non-native nucleic acid sequence within it, such that a non-native protein is produced. The recombinant plant viral nucleic acid construct may contain one or more additional non-native subgenomic promoters. Each non-native subgenomic promoter is capable of transcribing or expressing adjacent genes or nucleic acid sequences in the plant host and incapable of recombination with each other and with native subgenomic promoters. In addition, the recombinant plant viral nucleic acid construct may contain one or more cis-acting regulatory elements, such as enhancers, which bind a trans-acting regulator and regulate the transcription of a coding sequence located downstream thereto. Non-native nucleic acid sequences may be inserted adjacent to the native plant viral subgenomic promoter or the native and non-native plant viral subgenomic promoters if more than one nucleic acid sequence is included. The non-native nucleic acid sequences are transcribed or expressed in the host plant under control of the subgenomic promoter(s) to produce the desired products.

In a second embodiment, a recombinant plant viral nucleic acid construct is provided as in the first embodiment except that the native coat protein coding sequence is placed adjacent to one of the non-native coat protein subgenomic promoters instead of adjacent to a non-native coat protein coding sequence.

In a third embodiment, a recombinant plant viral nucleic acid construct is provided comprising a native coat protein gene placed adjacent to its subgenomic promoter and one or more non-native subgenomic promoters inserted into the viral nucleic acid construct. The inserted non-native subgenomic promoters are capable of transcribing or expressing adjacent genes in a plant host and are incapable of recombination with each other and with native subgenomic promoters. Non-native nucleic acid sequences may be inserted adjacent to the non-native subgenomic plant viral promoters such that said sequences are transcribed or expressed in the host plant under control of the subgenomic promoters to produce the desired product.

In a fourth embodiment, a recombinant plant viral nucleic acid construct is provided as in the third embodiment except that the native coat protein coding sequence is replaced by a non-native coat protein coding sequence.

Viral vectors are encapsidated by expressed coat proteins encoded by recombinant plant viral nucleic acid constructs as described hereinabove, to produce a recombinant plant virus. The recombinant plant viral nucleic acid construct or recombinant plant virus is used to infect appropriate host plants. The recombinant plant viral nucleic acid construct is capable of replication in a host, systemic spread within the host, and transcription or expression of one or more foreign genes (isolated nucleic acid) in the host to produce the desired protein.

In addition to the above, the nucleic acid molecule of the present invention can also be introduced into a chloroplast genome thereby enabling chloroplast expression.

A technique for introducing exogenous nucleic acid sequences to the genome of the chloroplasts is known. This technique involves the following procedures. First, plant cells are chemically treated so as to reduce the number of chloroplasts per cell to about one. Then, the exogenous nucleic acid is introduced into the cells preferably via particle bombardment, with the aim of introducing at least one exogenous nucleic acid molecule into the chloroplasts. The exogenous nucleic acid is selected by one ordinarily skilled in the art to be capable of integration into the chloroplast's genome via homologous recombination, which is readily effected by enzymes inherent to the chloroplast. To this end, the exogenous nucleic acid comprises, in addition to a gene of interest, at least one nucleic acid sequence derived from the chloroplast's genome. In addition, the exogenous nucleic acid comprises a selectable marker, which by sequential selection procedures serves to allow an artisan to ascertain that all or substantially all copies of the chloroplast genome following such selection include the exogenous nucleic acid. Further details relating to this technique are found in U.S. Pat. Nos. 4,945,050 and 5,693,507, which are incorporated herein by reference. A polypeptide can thus be produced by the protein expression system of the chloroplast and become integrated into the chloroplast's inner membrane.

Downregulation of a gene of interest can be effected on the genomic and/or the transcript level using a variety of molecules that interfere with transcription and/or translation (e.g., antisense, siRNA), or on the protein level using, e.g., antibodies, immunization techniques and the like.

For example, an agent capable of downregulating an activity of a polypeptide of interest is an antibody or antibody fragment capable of specifically binding a polypeptide of the present invention. Preferably, the antibody specifically binds at least one epitope of the polypeptide of interest. As used herein, the term "epitope" refers to any antigenic determinant on an antigen to which the paratope of an antibody binds.

Down-regulation at the RNA level can be effected by RNA-based silencing strategies which are effective in plants. See for example, Kusaba (2004) RNA interference in crop plants. Curr. Opin. Biotechnol. 15(2):139-43; Matzke (2001) RNA based silencing strategies in plants. Curr. Opin. Genet. 11:221-7.

For example, an agent capable of downregulating a polynucleotide of interest is a small interfering RNA (siRNA) molecule in the process of RNA interference (RNAi).

dsRNAs can be delivered to plants in several ways (reviewed in Waterhouse P, Helliwell C. 2003. Exploring plant genomes by RNA-induced gene silencing. *Nature Genet.* 4: 29-38): microprojectile bombardment with dsRNA or intron-containing hairpin RNA (ihpRNA)-expressing vectors; infiltration of plant tissue with an *Agrobacterium* strain carrying a T-DNA expressing an ihpRNA transgene; virus induced gene silencing (VIGS), in which the target sequence is integrated into viral sequences which are used to infect the plant, or are expressed from *Agrobacterium*-introduced transgenes, and by stable transformation with ihpRNA expressing transgenes. The various RNAi techniques each have advantages and disadvantages with respect to how persistent their effect is and the range of plants to which they can be applied, e.g. bombardment can be applied to any plant, but produces only transient effects. Alternatively, transformation with ihpRNA-expressing transgenes provides stable and heritable gene silencing, but requires efficient plant transformation techniques. ihpRNA transgenes have been shown to be very effective for a wide range of target genes in various plant species (reviewed in Waterhouse P, Helliwell C. 2003. Exploring plant genomes by RNA-induced gene silencing. *Nature Genet.* 4: 29-38; Wesley S, Helliwell C, Smith N, et al. 2001. Construct design for efficient, effective and high-throughput gene silencing in plants. *Plant J* 27: 581-590), indicating that the RNAi mechanism is probably conserved in all plant species. This is supported by a recent report of RNAi in the non-vascular moss *Physcomitrella patens* (Bezanilla M, Pan A, Quatrano R. 2003. RNA interference in the moss *Physcomitrella patens. Plant Physiol* 133: 470-474).

Antisense genetic constructs for fiber specific promoters (e.g., for SEQ ID NO: 85, 91) can be used to inhibit or lessen the expression of one or more fiber genes in fiber cells. The use of antisense constructs is described in U.S. Pat. No. 5,495,070 and in Smith, et al. Nature 334 724-726, 1988; Bird, et al. Bio/Technology 9: 635-639, 1991; Van der Krol, et al. Gene 72: 45-50, 1988.

It will be appreciated that the generation of fiber producing plant of desired traits according to the present invention can also be effected by crossing each of the above genetically modified plants with wild type, hybrid or transgenic plants, using methods which are well known in the art.

Once the transgenic planta of the present invention are generated, fibers are harvested (for example by mechanical picking and/or hand-stripping) and fiber yield and quality is determined.

The following describes methods of qualifying cotton fibers.

Fiber length—Instruments such as a fibrograph and HVI (high volume instrumentation) systems are used to measure the length of the fiber. HVI instruments compute length in terms of "mean" and "upper half mean" (UHM) length. The mean is the average length of all the fibers while UHM is the average length of the longer half of the fiber distribution.

Fiber strength—As mentioned, fiber strength is usually defined as the force required to break a bundle of fibers or a single fiber. In HVI testing the breaking force is converted to "grams force per tex unit." This is the force required to break a bundle of fibers that is one tex unit in size. In HVI testing the strength is given in grams per tex units (grams/tex). Fibers can be classified as low strength (e.g., 19-22 gms/tex), average strength (e.g., 23-25 gms/tex), high strength (e.g., 26-28 gms/tex), and very high strength (e.g., 29-36 gms/tex).

Micronaire—The micronaire reading of a fiber is obtained from a porous air flow test. The test is conducted as follows. A weighed sample of cotton is compressed to a given volume and controlled air flow is passed through the sample. The resistance to the air flow is read as micronaire units. The micronaire readings reflects a combination of maturity and fineness. Since the fiber diameter of fibers within a given variety of cotton is fairly consistent, the micronaire index will more likely indicate maturity variation rather than variations in fineness. A micronaire reading of 2.6-2.9 is low while 3.0-3.4 is below average, 3.5-4.9 is average and 5.0 and up are high. For most textile applications a micronaire of 3.5-4.9 is used. Anything higher than this is usually not desirable. It will be appreciated though, that different applications require different fiber properties. Thus, it is understood that a fiber property that is disadvantageous in one application might be advantageous in another.

As is illustrated in the Examples section, which follows, biomolecular sequences of the present invention are capable of increasing trichome/leaf hair number and length, as well as seed hair. As such biomolecular sequences of the present invention can be used to generate transgenic plants with increased trichome number/length which better deter herbivores, guide the path of pollinators, or affect photosynthesis, leaf temperature, or water loss through increased light reflectance. Additionally such transgenic plants may be used for the compartmentalized production of recombinant proteins and chemicals in trichomes, as described in details in WO 2004/111183 to Evogene Ltd.

Interestingly and unexpectedly, the present inventors found that polynucleotide sequences of the present invention are capable of increasing a biomass of a plant. It will be appreciated that the ability of the polypeptides of the present invention to increase plant yield/biomass/vigor is inherent to their ability to promote the increase in plant cell-size or volume (as described herein).

Thus, the present invention also envisages a method of increasing a biomass/vigor/yield of a plant (coniferous plants, moss, algae, monocot or dicot, as well as other plants listed in World Wide Web (dot) nationmaster (dot) com/encyclopedia/Plantae). This is effected by regulating expression and/or activity of at least one of the polynucleotides of the present invention, as described above.

As used herein the phrase "plant biomass" refers to the amount or quantity of tissue produced from the plant in a growing season, which could also determine or affect the plant yield or the yield per growing area.

As used herein the phrase "plant vigor" refers to the amount or quantity of tissue produced from the plant in a given time. Hence increase vigor could determine or affect the plant yield or the yield per growing time or growing area.

As used herein the phrase "plant yield" refers to the amount or quantity of tissue produced and harvested as the plant produced product. Hence increase yield could affect the economic benefit one can obtain from the plant in a certain growing are and/or growing time.

Thus, the present invention is of high agricultural value for promoting the yield of commercially desired crops (e.g., biomass of vegetative organ such as poplar wood, or reproductive organ such as number of seeds or seed biomass).

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

In Silico Identification of Cotton Genes Involved in Fiber Formation

Experimental Procedures

Figure 1:
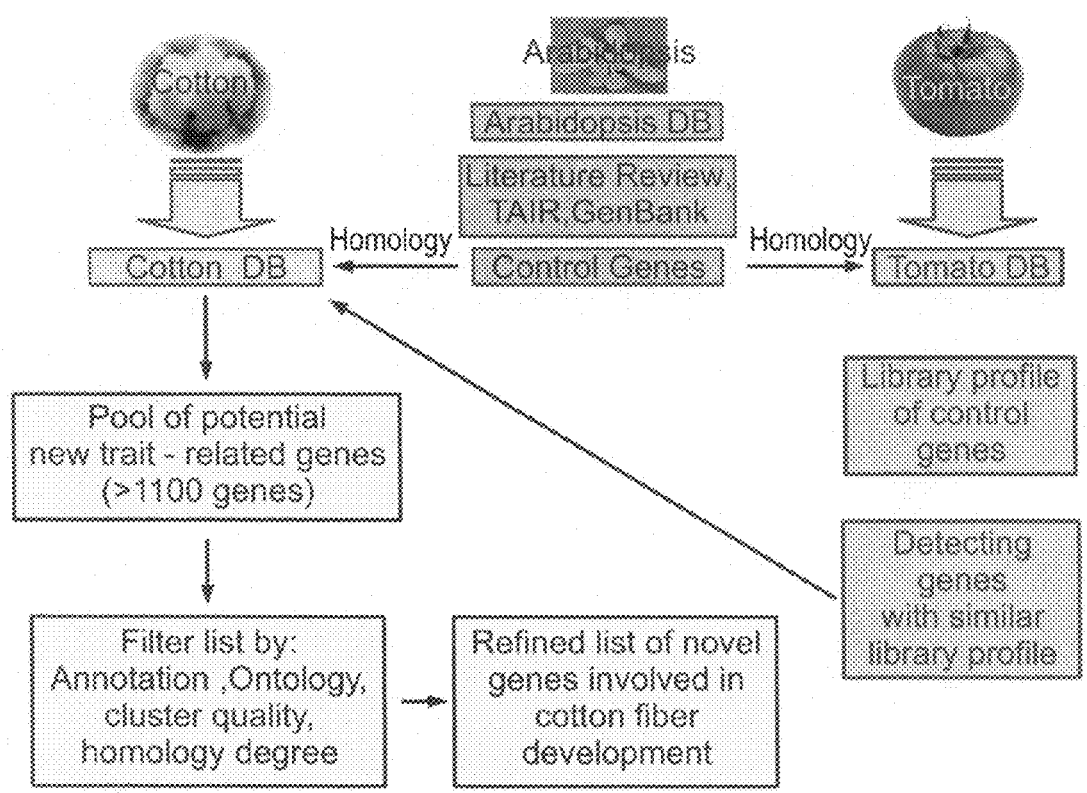

Interspecies comparison of expressed sequences—Two main tools were used during the data mining stage. Large numbers of gene profiles were queried from an ORACLE database housing Compugen's GeneCarta platform (Compugen Ltd. Israel). This data was loaded into MicroSoft Excel spreadsheets for further manual refinement. Using this data a cross species genomic comparison was effected, aiming at defining organs from other plant species for which publicly available EST libraries can be used both as models and as new sources of information to define new genes with key role in fiber formation (FIG. 1). This comparison analysis used mainly the cotton, *arabidopsis* and tomato databases.

Clustering and inter-species clustering of EST sequences—The cotton genomic database included less than 50,000 ESTs (Genbank release #135) originating primarily from two species *Gossypium arboreum* (~35,000 ESTs) and *Gossypium hirsutum* L. (~9,000 ESTs, Table 1, below). These ESTs were clustered and assembled using the LEADS™ software platform (Compugen Ltd, Israel) in two alternative approaches.

In the first approach, the ESTs from two species were clustered and assembled together (thereby mimicking the evolutionary process since *G. arboreum* is an ancestor of *G. hirsutum*). This process revealed 6478 clusters among them 3243 new clusters (without mRNA in the public database) that were defined as high quality clusters (Table 1, below).

In the second approach, ESTs from each species were clustered and assembled separately. Comparison between the two approaches showed that using the first approach adds valuable information to the cotton clusters without a significant bias in the analysis. The tomato genomic database contains 126,156 ESTs originating from about 30 well defined libraries that through the clustering and assembling process revealed 14034 clusters of which a large group of 12787 new high quality clusters (Table 1). The genomic data of *arabidopsis* includes 99417 ESTs (ftp://ftp (dot) ncbi (dot) nih (dot) gov/genbank/), 8573 full length cDNA (Rikken and genbank mRNAs ftp://ftp.ncbi.nih.gov/genbank/) and the entire DNA sequence. Using the LEADS software 23,148 clusters and 6777 singeltones (Single ESTs which no other EST was clustered therewith) were revealed, all of which were supported by ESTs sequences, contrary to the public consortium (TAIR, World Wide Web (dot) *arabidopsis* (dot) org/).

EST libraries from other plants and organs that share similar biological processes as cotton fiber were sought. Such ESTs are expected to serve as models and as new information sources for the identification of genes which are involved in the fiber development. To this end, a list of known genes that are suspected to be involved in fiber formation was generated. These genes originated from *arabidopsis* and were shown in various studies to have a key role in trichome formation (i.e., GL2, CPC, bHLH, TTG1, GL1, reviewed in Larkin J. C. et. al. 2003, Schellmann S. et al. 2002). Extensive comparative genomic analysis revealed that tomato genes, with high homology to cotton fiber genes and to *arabidopsis* trichome genes have a significant EST content in either leaf trichome and specific flower development libraries. Further analysis compared the genomic data of these three species—cotton, *Arabidopsis* and tomato (focusing on the tomato libraries mentioned above) as key parameters in the present database search (FIG. 1).

TABLE 1

Genomic databases of Cotton, Tomato and *Arabidopsis*

| Species | EST Lib description | EST count | mRNA | After LEADS (clusters) |
|---|---|---|---|---|
| G. arboreum | Fiber 6 DPA | 37,276 | 12 | 16,294 clusters |
| G. hirsutum | Fiber 7-10 DPA | 7,944 | 236 | on mixed |
| G. hirsutum | Flower ovule 1 DPA | 1,272 | 870 | production* |
| L. esculentum | All libraries | 115,859 | 7 | 25,678 clusters |
| L. hirsutum | Trichome libraries | 2,409 | 7 | on mixed production |
| L. pennellii | Trichome libraries | 2,723 | 24,450 | |
| A. thaliana | All libraries | 160,698 | mRNA | 25,678 clusters |

*clusters derived from different species, cotton *G. arboreum* and *G. hirsutum*, tomato *L. esculentum*, *L. hirsutum* and *L. pennellii*

In silico identification of cotton genes with a role in fiber development To find whether tomato genomic data can be used as a relevant source of genomic data to study cotton fiber development an extensive genomic comparison was effected to identify both tomato and cotton genes that have high homology to key genes determining *arabidopsis* trichome development (e.g., GL2, CPC, bHLH, TTG1, GL1).

Homologous genes were identified in cotton and tomato. Because almost all cotton ESTs were produced from cotton fibers, it was impossible to do in-silico prediction of the expression profile of those genes. However, wide tissue sources used for the production of the tomato EST database enabled identification of tissues in which trichome specific genes are expressed.

In tomato it was revealed that both trichome and ovule ESTs are enriched in clusters representing trichome specific genes. Interestingly, it was found that cotton fibers are produced from ovule coat cells. As tomato seeds are covered with hairy like tissue, similarly to cotton seeds, it was postulated that those hairs are developmentally linked to trichome and cotton fiber formation.

In tomato ~1100 clusters were found to include at least one EST from trichome libraries. Among them about 1000 sequences included sequences also originating from tomato flower libraries (in which the ovule tissue is present). Comparing this group of genes to cotton data revealed ~2300 cotton genes with high homology to the tomato trichome genes. Mining the database using these two groups of genes together with other bioinformatic information [cross species homology, Gene Onthology (GO)] revealed 80 cotton clusters predicted to have a key role in fiber formation. Those genes were selected based on the following criteria:

Cotton clusters with at least 2 ESTs;

Homology to tomato cluster with e-score higher than 1e-5;

Homology to tomato cluster with at least one EST coming from trichome libraries or one EST coming from ovule containing tissues;

The following criteria were considered as advantageous although not necessary:

Large number of ESTs in a cluster;

Transcription factor/signal transduction proteins;

Gene annotation related to cell expansion, turgor pressure, cell-wall synthesis.

The new genes together with the control cotton genes known to be involved in fiber formation were further analysed for their RNA expression profile in cotton plants.

Example 2 mRNA Expression Analysis of Genes Identified According to the Teachings of the Present Invention To study the RNA expression profile of candidate genes identified as described in Example 1 above, a reverse transcription was effected followed by real time PCR (RT-qPCR).

Experimental Procedures

Quantitative Real time PCR analysis (qRT PCR)—To verify the levels of expression specificity and trait-association, Reverse Transcription following quantitative (Real-Time) PCR (RTqPCR) was effected. Total RNA was extracted at different stages of fiber development (from the day of anthesis till day 20—post anthesis). To study the specificity of expression, RNA from other tissues of the cotton plants were collected and analysed for control expression (i.e., young leaves, young stems, mature stems, young roots, sepals, petals, and stamen). For this purpose, RNA was extracted from Cotton tissue using Hot Borate RNA Extraction protocol according to World Wide Web (dot) eeob (dot) iastate (dot) edu/faculty/WendelJ/ultramicrorna (dot) html Reverse transcription was effected using 1.5 µg total RNA, using 300 U Super Script II Reverse Transcriptase enzyme (Invitrogen), 225 ng random deoxynucleotide hexamers (Invitrogen), 500 µM dNTPs mix (Takara, Japan), 0.2 volume of ×5 RT buffer (Invitrogen), 0.01M DTT, 60 U RNAsin (Promega), DEPC treated double distilled water was added up to 37.5 µl. RT reactions were incubated for 50 min at 42° C., followed by 70° C. for 15 min. cDNA was diluted 1:20 in Tris EDTA, pH=8. 5 mL of the diluted cDNA was used for qRT-PCR.

Quantitative RT-PCR was performed on cDNA (5 µL), using ×1 SYBR GREEN PCR master mix (Applied Biosystems), forward and reverse primers 0.3 µM each. The ABI7000 real-time PCR machine was used with the following conditions 50° C. for 2 min, 95° C. for 10 min, 40 times of 95° C. for 15 sec and 1 min at 60° C., followed by 95° C. for 15 sec, 60° C. for 60 sec, and 70 times of 60° C. for 10 sec+0.5° C. increase in each cycle. For each gene, a standard curve was prepared from a pool of RTs from all samples, in 5 dilutions (dilutions—1:60, 1:200, 1:600, 1:2000, 1:10000). The standard curve plot [ct (cycle threshold) vs. log (concentration)] should have R>=0.98 with an efficiency in the range of 100%+/−5%. The levels of expression (Qty) measured in the qPCR were calculated using the efficiency (E) of the amplification reaction and the corresponding C.T. (the cycle at which the samples crossed the threshold) Qty=E−C.T. The dissociation curves obtained were inspected for the absence of unwanted additional PCR products or primer-dimers. Reactions were repeated at least twice. The calculation method is based in the fact that the efficiencies of the reactions of the GOI (gene of interest) and of the housekeeping genes are similar.

To normalize the expression level between the different tissues, specific primers were designed for specifically hybridizing with the following housekeeping genes: Actin (GenBank Accession No. D88414 SEQ ID NO: 28, Forward and reverse primers are set forth in SEQ ID NO: 68 and 69, respectively), GAPDH (GenBank Accession No. COTCW-PPR, partial sequence, SEQ ID NO: 29, Forward and reverse primers are set forth in SEQ ID NO: 97 and 98, respectively), and RPL19 (GenBank Accession No. AI729179, SEQ ID NO: 30, Forward and reverse primers are set forth in SEQ ID NO: 99 and 100, respectively).

Using this methodology it was possible to identify genes that show elevated expression during fiber elongation, as well as genes that show unique cotton fiber specificity. Genes that showed elevated expression during anthesis that decreases during fiber elongation were considered good candidates to be involved in fiber differentiation and initiation. Notably, the above-described quantification methodology did not provide absolute expression levels, but provided good parameters for scoring the relative gene expression along fiber development as differences as high as over 1000 fold in the maximal levels of expression reached by different genes were detected (Table 2, below).

Results 88 cotton genes were evaluated for expression profile in different tissues of cotton (*Gossypium hirsutum*, var Acala). According to the gene expression results, 23 genes were predicted to improve fiber yield and quality. Expression profile of all the candidate genes are presented in Table 2.

TABLE 2

| SEQ ID NO. | Gene ID | | | | | | | | |
|---|---|---|---|---|---|---|---|---|---|
| | -DPA* | 0-1 dpa | 12-14 dpa | 15-17 dpa | 18-20 dpa | 2-3 dpa | 4-5 dpa | 6-8 dpa | 9-11 dpa |
| CT1/1 | 0.053** | 0.049 | 2.034 | 2.138 | 2.477 | 0.295 | 0.976 | 1.347 | 1.118 |
| CT2/2 | 0.025 | 0.040 | 0.870 | 0.735 | 0.819 | 0.060 | 0.183 | 0.238 | 0.267 |
| CT3/3 | 0.082 | 0.070 | 0.511 | 0.632 | 0.819 | 0.057 | 0.084 | 0.116 | 0.092 |
| CT4/4 | 1.313 | 0.719 | 0.389 | 0.561 | 0.419 | 0.622 | 0.666 | 0.757 | 0.774 |
| CT6/5 | 0.093 | 0.075 | 0.580 | 0.732 | 0.916 | 0.066 | 0.095 | 0.104 | 0.110 |
| CT7/6 | 0.074 | 0.055 | 0.362 | 0.297 | 0.197 | 0.112 | 0.219 | 0.228 | 0.263 |
| CT9/7 | 0.276 | 0.980 | 1.166 | 0.715 | 0.960 | 0.980 | 1.265 | 1.103 | 2.095 |
| CT11/8 | 0.148 | 0.163 | 0.132 | 0.163 | 0.121 | 0.142 | 0.131 | 0.163 | 0.097 |
| CT20/9 | 0.074 | 0.035 | 0.021 | 0.013 | 0.016 | 0.045 | 0.042 | 0.032 | 0.033 |
| CT22/10 | 2.989 | 1.631 | 0.870 | 0.838 | 0.749 | 1.693 | 1.268 | 1.017 | 1.589 |
| CT26/11 | 0.022 | 0.001 | 0.017 | 0.001 | 0.018 | 0.017 | 0.028 | 0.039 | 0.017 |
| Ct27/12 | 0.010 | 0.009 | 0.009 | 0.009 | 0.010 | 0.008 | 0.005 | 0.005 | 0.003 |
| CT40/16 | 0.016 | 0.016 | 0.014 | 0.023 | 0.024 | 0.012 | 0.013 | 0.016 | 0.017 |
| CT49/17 | 0.056 | 0.114 | 0.156 | 0.131 | 0.111 | 0.161 | 0.283 | 0.315 | 0.332 |
| CT70/18 | 1.406 | 2.247 | 8.460 | 7.782 | 10.709 | 2.152 | 5.313 | 7.361 | 4.796 |
| CT71/19 | 0.095 | 0.403 | 1.736 | 2.079 | 2.670 | 0.338 | 0.685 | 1.139 | 0.809 |
| CT74/20 | 2.971 | 2.555 | 3.474 | 4.398 | 5.859 | 3.135 | 4.301 | 4.272 | 6.983 |
| CT75/21 | 1.727 | 0.282 | 16.012 | 15.856 | 20.171 | 3.812 | 8.935 | . | 20.295 |
| CT76/22 | 0.000 | 0.002 | 0.041 | 0.039 | 0.080 | 0.007 | 0.020 | 0.015 | 0.036 |
| CT77/23 | 0.005 | 0.011 | 0.555 | 0.892 | 1.434 | 0.057 | 0.161 | 0.166 | 0.123 |
| CT81/24 | 0.161 | 0.196 | 3.455 | 4.880 | 14.028 | 0.210 | 0.354 | 0.515 | 1.153 |
| CT82/25 | 0.024 | 0.022 | 0.005 | 0.004 | 0.006 | 0.018 | 0.016 | 0.014 | 0.011 |
| CT84/27 | 0.007 | 0.005 | 0.136 | 0.167 | 0.371 | 0.004 | 0.014 | 0.027 | 0.031 |
| CT88/13 | 0.002 | 0.371 | 0.841 | 2.978 | 3.045 | 4.947 | 14.725 | 17.514 | 28.290 |

| SEQ ID NO. | Gene ID | | | | | | | |
|---|---|---|---|---|---|---|---|---|
| | mature leaves | mature stems | petals | sepals | stamen | young leaves | young roots | young stems |
| CT1/1 | 0.53 | 0.029 | 9.368 | 0.336 | 0.277 | 0.347 | 0.002 | 0.202 |
| CT2/2 | 0.014 | 0.000 | 0.001 | 0.008 | 0.01 | 0.021 | 0.068 | 0.025 |
| CT3/3 | 0.109 | 0.032 | 0.038 | 0.086 | 0.020 | 0.142 | 0.037 | 0.063 |
| CT4/4 | 0.001 | 0.001 | 0.004 | 0.000 | 0.044 | 0.001 | 0.003 | 0.003 |
| CT6/5 | 0.113 | 0.028 | 0.037 | 0.085 | 0.026 | 0.148 | 0.037 | 0.044 |
| CT7/6 | 0.066 | 0.001 | 0.125 | 0.007 | 0.001 | 0.055 | 0.000 | 0.049 |
| CT9/7 | 0.012 | 0.000 | 0.019 | 0.032 | 0.004 | 0.008 | 0.000 | 0.012 |
| CT11/8 | 0.000 | 0.000 | 0.000 | 0.000 | 0.068 | 0.000 | 0.000 | 0.000 |
| CT20/9 | 0.051 | 0.051 | 0.459 | 0.076 | 0.572 | 0.037 | 0.069 | 0.067 |
| CT22/10 | 0.541 | 0.636 | 0.168 | 0.408 | 0.521 | 0.463 | 1.308 | 0.762 |
| CT26/11 | . | . | 0.006 | . | 0.001 | . | . | 0.000 |
| Ct27/12 | . | 0.007 | 0.008 | 0.005 | 0.001 | 0.001 | 0.001 | 0.007 |
| CT40/16 | 0.007 | 0.000 | 0.002 | 0.022 | 0.005 | 0.005 | 0.001 | 0.004 |
| CT49/17 | 0.031 | 0.002 | 0.011 | 0.007 | 0.007 | 0.060 | 0.005 | 0.047 |
| CT70/18 | 1.065 | 0.492 | 9.976 | 0.671 | 1.207 | 1.904 | 1.177 | 1.294 |
| CT71/19 | 0.627 | 1.708 | 1.258 | 1.268 | 6.599 | 1.301 | 0.004 | 0.480 |
| CT74/20 | 0.017 | 0.002 | 0.203 | 0.015 | 0.136 | 0.030 | 0.003 | 0.464 |
| CT75/21 | 4.473 | 3.644 | 83.72 | 6.317 | 28.659 | 8.534 | 0.872 | 2.759 |
| CT76/22 | 0.000 | 0.000 | 0.000 | 0.000 | 0.000 | . | 0.000 | 0.000 |
| CT77/23 | 0.016 | 0.026 | 0.020 | 0.009 | . | 0.023 | 0.001 | 0.003 |
| CT81/24 | 9.477 | 26.444 | 1.165 | 0.913 | 0.021 | 6.614 | 0.004 | 1.089 |
| CT82/25 | 0.053 | 0.034 | 0.017 | 0.045 | 0.036 | 0.004 | . | 0.000 |
| CT84/27 | 0.036 | 0.346 | 0.034 | 0.196 | 0.101 | 0.061 | 0.071 | 0.035 |
| CT88/13 | 0.001 | 0.034 | 0.005 | 0.000 | . | 0.005 | 0.004 | 0.007 |

Reverse-transcription following quantitative PCR was performed using real-time PCR, on tissues of either young or mature cotton (*G. hirsutum* var Acala) plants. Relative amounts of mRNA of each gene are presented in all examined tissues. dpa—days post anthesis, of ovule and fibers tissues (until 10 dpa) or only fiber tissue (after 10 dpa).

Two main criteria were used to select cotton genes as candidates that may be involved in fiber development according to their RNA profiling. Genes showing a high degree of fiber expression specificity and genes displaying expression level, which changes concomitantly with fiber development (Table 3, below).

Twenty three genes met these selection criteria:
CT-1 (SEQ ID NOs. 1 and 106), CT_2 (SEQ ID NOs. 2 and 107), CT_3 (SEQ ID NOs. 3 and 108), CT_4 (SEQ ID NOs. 4 and 109) CT_6 (SEQ ID NOs. 5 and 110), CT_7 (SEQ ID NOs. 6 and 111), CT_9 (SEQ ID NOs. 7 and 112), CT_11 (SEQ ID NOs. 8 and 113), CT_20 (SEQ ID NOs. 9 and 114), CT_22 (10 and 115), CT_26 (SEQ ID NOs. 11 and 116), CT_27 (SEQ ID NOs. 12 and 117), CT_40 (SEQ ID NOs. 16 and 118), CT_49 (SEQ ID NOs. 17 and 119), CT_70 (SEQ ID NOs. 18 and 120), CT_71 (SEQ ID NOs. 19 and 121), CT_74 (SEQ ID NOs. 20 and 122), CT_75 (SEQ ID NOs. 21 and 123), CT_76 (SEQ ID NOs. 22 and 124), CT_77 (SEQ ID NOs. 23 and 125), CT_81 (SEQ ID NOs. 24 and 126), CT_82 (SEQ ID NOs. 25 and 95), CT_84 (SEQ ID NOs. 27 and 96) and CT_88 (SEQ ID NOs. 13 and 26).

CT-4, 22, 20, 27, 40, 82 (SEQ ID NOs: 4, 10, 9, 12, 16 and 25, respectively) were chosen mainly as candidate genes that may have a role in fiber initiation (Table 3) while CT 27 (SEQ ID NO: 12), which is a homologue gene to GL3, was also used as a control (in FIG. 2d CT 22, SEQ ID NO: 10 is shown).

CT-1, 2, 3, 6, 7, 9, 49, 70, 71, 74, 75, 76, 77, 81, 84 (SEQ ID NOs. 1, 2, 3, 5, 6, 7, 17, 18, 19, 20, 21, 22, 23, 24 and 27, respectively, see FIGS. 2a, c) were predicted to be involved in the fiber elongation and quality (strength and finesse) according to their expression pattern (Table 3, FIG. 2C CT 1 is shown).

CT11, 40, 74 and CT 26 (SEQ ID NOs. 8, 16, 20 and 11, respectively, see FIGS. 2a, b) which are homologous to Glabrous1 from Arabidopsis (GenBank Accession No. AB006078) are fiber specific genes that showed uniform and fiber-specific expression during all stages of fiber development (Table 3, in FIG. 2B CT 11 is shown as an example). Expression profile of all the chosen genes are shown in Table 2, above.

The selected genes were over-expressed in transgenic *arabidopsis* and tomato, using the constitutive CaMV promoter of 35S (SEQ ID NO. 31). Transgenic plants were further evaluated for epidermal modifications, trichome density and length and seed hair yield (as further described hereinbelow).

Example 3

Analysis of Gene Expression Using Publicly Available Microarrays

Further information about the expression of the selected genes (Example 2, above) was retrieved by statistical analysis of microarray data from *arabidopsis*. Essentially, the best homologs of the new candidate genes in *arabidopsis* were compared to a set of 77 microarrays experiment of different tissues of *Arabidopsis* (AtGenExpress databases, the Principal investigator for AFGN: Prof. Dr. Lutz Nover, Botanisches Institut, Molekulare Zellbiologie, FB Biologie and Informatik der J. W. Goethe Universität Frankfurt; Biozentrum N200 3OG, Marie-Curie-Strasse 9, 60439 Frankfurt am Main, World Wide Web (dot) *arabidopsis* (dot) org/info/expression/ATGenExpress.jsp).

Polynucleotide sequences that were highly expressed in elongated cells or inflorescence meristems were selected for further analysis.

Table 4 below lists tissues which exhibit the highest levels of gene expression.

TABLE 4

| | Tissues with high expression | <Fold change/ specificity | Related to fiber |
|---|---|---|---|
| CT_1 | Seed, siliques | 10-20 | Elongated cells |
| CT_11 | carpels, flower, seed, siliques | Tissue specific | Flower specific |
| CT_2 | root, seedlin and sepals | Tissue specific | Elongated cells, |
| CT_22 | carpels, flower, inflorescence, shoot | 4-10 | inflorescence |

TABLE 3

| CT # | Gene annotation | Initiation | Fiber Quality & Elongation | Stable and Specific Fiber Expression | Fiber Specific | Biological Process |
|---|---|---|---|---|---|---|
| CT_2 | Acid sucrose-6-phosphate hydrolase | | v | | Yes | carbohydrate metabolism |
| CT_7 | Putative acyltransferase | | v | | | unknown |
| CT_9 | Hypothetical protein | | v | | Yes | tRNA processing |
| CT_49 | Hypothetical protein | | v | | | unknown |
| CT_1 | GDSL-motif lipase/hydrolase-like protein | | v | | | unknown |
| CT_3 | Putative mitochondrial protein | | v | | | unknown |
| CT_6 | Aspartyl protease | | v | | | proteolysis and peptidolysis |
| CT_70 | Cysteine protease | | v | | | water deprivation |
| CT_71 | Dehydration-responsive protein | | v | | | dessication |
| CT_75 | Lipid transfer protein, putative | | v | | | |
| CT_76 | Putative receptor kinase | | v | | Yes | protein amino acid phosphorylation |
| CT_77 | Hypothetical protein | | v | | Yes | |
| CT_81 | APETAL2-like protein | | v | | | cell wall organization and biogenesis |
| CT_84 | Hypothetical protein | | v | | | aromatic amino acid family biosynthesi |
| CT_4 | Cytochrome P450-like protein | v | | | Yes | electron transport |
| CT_20 | MYB-related protein homologue | v | | | | regulation of transcription |
| CT_22 | Hypothetical protein | v | | | | unknown |
| CT_27 | bHLH transcription factor-like protein | v | | | | regulation of transcription |
| CT_82 | MADS box protein-like | v | | | | regulation of transcription |
| CT_11 | Agamous-like MADS-box transcription factor | | | v | Yes | regulation of transcription |
| CT_26 | MYB-related protein homologue | | | v | Yes | cell fate commitment |
| CT_40 | Lipid-transfer protein 3 precursor (LTP 3) | | | v | Yes | lipid transport |
| CT_74 | EN/SPM-like transposon protein | | | v | Yes | cell wall organization and biogenesis |

TABLE 4-continued

| | Tissues with high expression | <Fold change/ specificity | Related to fiber |
|---|---|---|---|
| CT_4 | Petals, stamen | >10 | Elongated cells, |
| CT49 | siliques | >2 | Elongated cells, |
| CT_7 | carpels, flower, inflorescence, petals, shoot, siliques, | 10-30 | inflorescence |
| CT_70 | flower, root, stamen | Almost tissue specific | |
| CT_76 | carpels, flower, inflorescence, shoot, siliques | >2 | Elongated cells, & inflorescence |
| CT_77 | seeds, pollen, stemen, petals, sepals, siliques | 10-50 | Elongated cells |
| CT_82 | inflorescence, shoot stem | 3-6 | inflorescence |
| CT_88 | petals, stamen | | Elongated cells |

Example 4

Establishing a Correlation Between Expression of Candidate Genes and Fiber Length In order to define correlations between the levels of RNA expression of the selected genes and fiber length, fibers from 4 different cotton lines were analyzed. These fibers were selected showing very good fiber quality and high lint index (Pima types, originating from other cotton species, namely *G. barbadense*) and different levels of quality and lint indexes from various *G. hirsutum* lines: good quality and high lint index (Acala type), medium lint index (Coker type) and poor quality and short lint index (Tamcot type).

Experimental Procedures

RNA extraction—Fiber development stages, representing different fiber characteristic, at 5, 10 15 and 20 DPA were sampled and RNA was extracted as describe in Example 2.

Fiber assessment—Fiber length of the above lines was measured using fibrograph. The fibrograph system was used to compute length in terms of "Upper Half Mean" length. The upper half mean (UHM) is the average length of longer half of the fiber distribution. The fibrograph measures length in span lengths at a given percentage point (World Wide Web (dot) cottoninc (dot) com/ClassificationofCotton/?Pg=4#Length.)

Results

Four different cotton lines were grown in Rehovot, Israel during summer 2004, and their fiber length was measured. The fibers UHM values are summarized in Table 5, below:

TABLE 5

| | Length (UHM) |
|---|---|
| Pima S5 | 1.40 ± 0 a |
| Acala | 1.23 ± 0.01 b |
| Coker 310 | 1.18 ± 0.01 c |
| Tamcot | 1.15 ± 0.02 c |

Five genes were tested for correlation between gene expression and fiber length (presented for CT_76 in FIG. 3). The results are summarized in the Table 6 below:

TABLE 6

| | | Tissue Sampling Day (DPA) | | | | | | |
|---|---|---|---|---|---|---|---|---|
| | | 0 | 5 | | 10 | | 15 | |
| | | Relative amounts of mRNA | Relative amounts of mRNA | Relative expression Related to T0 | Relative amounts of mRNA | Relative expression Related to T0 | Relative amounts of mRNA | Relative expression Related to T0 |
| CT_1 | Tamcot | 0.75 | 2.99 | 4.0 | 4.71 | | | |
| | Coker 310 | 0.51 | 4.80 | 9.3 | 7.56 | | | |
| | Acala | 0.64 | 5.08 | 7.9 | 8.01 | | | |
| CT_2 | Tamcot | 0.03 | 0.19 | 7.6 | 8.17 | | | |
| | Coker 310 | 0.03 | 0.35 | 11.4 | 15.04 | | | |
| | Acala | 0.02 | 0.36 | 17.7 | 15.28 | | | |
| | Pima S5 | 0.02 | 0.41 | 23.6 | 17.58 | | | |
| CT_40 | Tamcot | 0.28 | | | | | 0.47 | 1.67 |
| | Coker 310 | 0.37 | | | | | 0.46 | 1.24 |
| | Acala | 0.30 | | | | | 0.67 | 2.25 |
| | Pima S5 | 0.37 | | | | | 1.03 | 2.75 |
| CT_76 | Tamcot | 0.01 | 0.03 | 5.4 | 0.01 | 2.3 | 0.00 | 0.10 |
| | Coker 310 | 0.01 | 0.08 | 8.9 | 0.04 | 5.1 | 0.00 | 0.10 |
| | Acala | 0.01 | 0.12 | 16.6 | 0.06 | 9.1 | 0.00 | 0.12 |
| | Pima S5 | 0.01 | 0.13 | 122.4 | 0.18 | 177.9 | 0.12 | 99.51 |
| CT_81 | Tamcot | 0.50 | 1.33 | 2.68 | 5.03 | 10.15 | 1.11 | 2.24 |
| | Coker 310 | 0.31 | 2.64 | 8.65 | 4.51 | 14.76 | 0.84 | 2.75 |
| | Acala | 0.49 | 4.38 | 8.98 | 6.36 | 13.05 | 3.65 | 7.49 |

Reverse-transcription following quantitative PCR was performed using real-time PCR, on tissues of 0, 5 10 and 15 DPA of cotton (*G. hirsutum* var Tamcot, Coker and Acala, and *G. barbadense* var Pima S5) plants. Relative amounts of mRNA and Relative expression related to T0 of each gene are presented in all examined tissues.

Example 5

Cloning of the Selected Genes in a Binary Vector Under Constitutive Regulation and Recombinant Expression of the Same ORF analysis—Gene sequences of the present invention were analyzed for ORFs using Gene Runner software version 3.05 (Hasting Software, Inc: World Wide Web (dot) generunner (dot) com/). ORFs of each gene were compared to Genbank database, using Blast (World Wide Web (dot) ncbi (dot) nlm (dot) nih (dot) gov/BLAST/). By comparing to highest homologous ORFs, the position of the ATG initiation codon was determined. All the sequences described herein were shown to have a predicted full length ORF and to include the predicted ATG starting codon.

Cloning into the pPI expression vector—For cloning genes of the present invention, total RNAs from the various developmental stages of fiber producing cells was extracted, using Hot Borate RNA Extraction from Cotton Tissue according to World Wide Web (dot) eeob (dot) iastate (dot) edu/faculty/WendelJ/rnaextraction (dot) html. Complementary DNA (cDNA) molecules were produced from mRNA using M-MuLV reverse-transcriptase (RT) enzyme (Roche) and $T_{16}NN$ DNA primer, following protocol provided by the manufacturer. cDNA amplification was done for 19 genes, out of the sequences above, namely CT clones number 1, 2, 3, 6, 7, 9, 11, 20, 22, 27, 40, 71, 74, 75, 76, 81, 82, 84 and 88, by PCR using PFU proof reading DNA polymerase enzyme (Promega World Wide Web (dot) promega (dot) com/pnotes/68/738_07/7381_07 (dot) html) following the protocol provided by the manufacturer. Primers for each gene were designed to span the full ORF. Additional restriction endonuclease sites were added to the 5' end of each primer to facilitate further cloning of the CTs to the binary vector (pPI). Table 7 below, lists the primers used for cloning each of the genes:

TABLE 7

| CT No | Forward Primer/SEQ ID NO: | Reverse Primer/SEQ ID NO: | upstream restriction site | downstream restriction site |
|---|---|---|---|---|
| CT_1 | ACCCGGGATGGATGGTTATTGTAGCAGAAGG/32 | GCCGAGCTCGAATCAAATGAGGGCAATGCC/33 | SmaI | SacI |
| CT_2 | AATCTAGACAAGTACAGAAGCTCAATTCCC/34 | TGATAATCATGTGGAAGCAACC/35 | XbaI | |
| CT_3 | CAGCCCGGGTGATGGAACTGAGCATTCAG/36 | CGTGAGCTCTGATTAGAGTTTCAAGTGCATG/37 | SmaI | SacI |
| CT_6 | TTTCCCGGGTTGTTGTCATGGCTTCTCTGC/38 | ATGGAGCTCATATTCATGGCCAAAACAC/39 | SmaI | SacI |
| CT_7 | G CACCCGGGAAAGGAAATGGCAGGCGTC/40 | TTTCGATATCCACAGTACCCTACTTCCATGC/41 | SmaI | EcoRV |
| CT_9 | TACCCGGGTACCATTACTCTACTACAGCTGC/42 | GAGAGCTCAACAGACAAAGACCAGACTGG/43 | SmaI | SacI |
| CT_11 | ACCCCCGGGCAAGTGATCAAAGAGAATGG/44 | CATGAGCTCTTTCTCCAACTCCTCTACCC/45 | SmaI | SacI |
| CT_20 | CCCCCGGGTCCCTATTGCATGCCTTTC/46 | TTGAGCTCACTCGATCTTACTCATCC/47 | SmaI | SacI |
| CT_22 | AGCCCGGGAGATAGAGAGATGGGAGGTCC/48 | TCGAGCTCTGGGGCAACAATCATTTACC/49 | SmaI | SacI |
| CT_27 | TCCCCGGGCATCTGATCTAATTGTTGGTGG/50 | TTGGATATCGCACCTTATGACATGGGATC/51 | SmaI | EcoRV |
| CT_40 | TTCCCGGGTACAAACATGGCTAGTTCCG/52 | TCGAGCTCATCAACCTCACTGCACCTTG/53 | SmaI | SacI |
| CT_71 | TAGTCACTCCTGTTCTAGATGAAG/54 | CTGAGCTCCAGGATTTTTACTTAGGGACCC/55 | XbaI | SacI |
| CT_74 | TACCCGGGCATACAGAGATGGAGAGGC/56 | ACGAGCTCAAAGGTGTTTGCTTAGGTCC/57 | SmaI | SacI |
| CT_75 | AGCCCGGGAGAAAGATGATGAAAAGGGG/58 | AAGATATCAAATCCCATGCAAAACCCC/59 | SmaI | EcoRV |
| CT_76 | AACCCGGGCGGCAACTTAAAAGAAAACC/60 | AAGAGCTCCTTTGTTGGCTTCTCAAG/61 | SmaI | SacI |
| CT_81 | GACCCGGGACTGTAAAAAAGCATAGG/62 | GCGAGCTCAGCTTAAGGATGATGGGGAG/63 | SmaI | SacI |
| CT_82 | ATCCCGGGGATGGTGAGAGGCAAAATTC/64 | ACGAGCTCTAGCAATGGCGATAACGTAC/65 | SmaI | SacI |
| CT_84 | ATCCCGGGTTCCATGAAAAGGGTCTCG/66 | GTGAGCTCTATCGTCGTTGTCCTTCAGC/67 | SmaI | SacI |

The resultant PCR blunt ended products, were purified using PCR Purification Kit (Qiagen, Germany), digested with the appropriate restriction endonucleases (Roche) and cloned into the pPI binary vector (FIG. 4), while replacing the existing GUS reporter gene. pPI is a modified version of pBI101.3 (Clontech, Accession No. U12640). pPI was constructed by inserting a synthetic poly-(A) signal sequence, which originated from pGL3 Basic plasmid vector (Promega, Acc No U47295, where the synthetic poly-(A) signal sequence is located between base-pairs 4658-4811), into the HindIII restriction site of pBI101.3 (while reconstituting the HindIII site, downstream to the poly-(A) insert), to avoid the possibility of read-through effect of the upstream Nos-promoter. To replace the GUS gene with each one of the CT genes in the pPI binary vector, pPI was digested with the appropriate restriction enzymes [5' prime restriction enzyme is either SmaI or XbaI and 3' prime restriction enzyme is either SacI or EcoRV (Roche—using the protocol provided by the manufacturer)]. Open binary vector was purified using PCR Purification Kit (Qiagen, Germany). 5-75 ng of PCR product of each of the CT genes and 100 ng of open pPI plasmid vector were ligated in 10 μL ligation reaction volume using T4 DNA ligase enzyme (Roche), following the protocol provided by the manufacturer. Ligation products were introduced into *E. coli* cells.

Recombinant expression in bacteria—60 μL of *E. coli*, strain DH5-α competent cells (about $10^9$ cells/mL) were transformed using 1 μl of ligation reaction mixture by electroporation, using a MicroPulser electroporator (Biorad), 0.2 cm cuvettes (Biorad) and EC-2 electroporation program (Biorad). *E. coli* cells were grown on 0.8 mL LB liquid medium at 37° C. for 1 hrs and 0.2 mL of the cell suspension were plated on LB-agar plates supplemented with the antibiotics kanamycin 50 mg/L (Sigma). Plates were then incubated at 37° C. for 16 hrs. Bacteria colonies were grown and expression was confirmed by PCR amplification using primers which were designed to span the inserted sequence in the binary vector. Primers used for DNA amplification of the inserts in the pPI binary vector were:

```
5'-GGTGGCTCCTACAAATGCCATC-3'    (forward, SEQ ID
                                 NO. 70)
and
5'-AAGTTGGGTAACGCCAGGGT-3'.     (reverse, SEQ ID
                                 NO. 71)
```

PCR products were separated on 1.5% agarose gels and product sizes were estimated by comparing to DNA ladder (MBI Fermentas). PCR products with the predicted size were sequenced using the same primers previously used for PCR amplification (See Table 7, above).

Additional primers, which were designed based on the sequence of each gene insert, were used to complete the sequencing of the full length ORF insert.

Sequencing of the inserted sequence was performed to verify that the clones were introduced in the right orientation, and to eliminate the possibility that sequence errors were included during PCR amplification. DNA sequences were determined using ABI 377 sequencer (Amersham Biosciences Inc).

Into each one of the 19 pPI binary constructs harboring the CT genes, the constitutive, Cauliflower Mosaic Virus 35S promoter was cloned.

Cauliflower Mosaic Virus 35S promoter sequence, originated from the pBI121 vector (Clontech, Accession No AF485783) was cloned by digesting the pBI121 vector with the restriction endonucleases HindIII and BamHI (Roche) and ligated into the binary constructs, digested with the same enzymes (SEQ ID NO. 31).

Example 6

*Agrobacterium* Transformation of Binary Plasmids Harboring the Genes of Interest and Expression in *Arabidopsis* and Tomato Plants Each of the nineteen binary constructs, comprising the 35S promoter upstream of each of the CTs genes was transformed into *Arabidopsis* or tomato plants via *Agrobacterium tumefacience* transformation.

60 μL of *Agrobacterium tumefaciens* GV301 or LB4404 competent cells (about $10^9$ cells/mL) were transformed with 20 ng of binary plasmid via electroporation, using a MicroPulser electroporator (Biorad), 0.2 cm cuvettes (Biorad) and EC-2 electroporation program (Biorad).

*Agrobacterium* cells were grown on 0.8 mL LB liquid medium at 28° C. for 3 hrs and 0.2 mL of the cell suspension were plated on LB-agar plates supplemented with the antibiotics gentamycin 50 mg/L (for *Agrobacterium* strains GV301) or streptomycin 300 mg/L (for *Agrobacterium* strain LB4404) and kanamycin 50 mg/L (Sigma). Plates were then incubated at 28° C. for 48 hrs. *Agrobacterium* colonies were grown and PCR amplification was performed on *Agrobacterium* cells, using primers which were designed to span the inserted sequence in the binary vector.

Primers used for PCR amplification were: 5'-GGTG-GCTCCTACAAATGCCATC-3' (forward, SEQ ID NO. 70) and 5'-AAGTTGGGTAACGCCAGGGT-3' (reverse, SEQ ID NO. 71).

PCR products were separated on 1.5% agarose gels and product sizes were determined by comparing to DNA ladder (MBI Fermentas). PCR products with the predicted size were sequenced using the primers which were used for the PCR amplification. Sequencing of the inserted sequence was performed to verify that the right clones were introduced into the *Agrobacterium* cells. DNA sequencing was effected using ABI 377 sequencer (Amersham Biosciences Inc.).

Plant Transformation and Cultivation:

Transformation of *Arabidopsis thaliana* plants with putative cotton genes—*Arabidopsis thaliana* Columbia plants (T0 plants) were transformed using the Floral Dip procedure described by Clough and Bent and by Desfeux et al., with minor modifications. Briefly, T0 Plants were sown in 250 ml pots filled with wet peat-based growth mix. The pots were covered with aluminum foil and a plastic dome, kept at 4° C. for 3-4 days, then uncovered and incubated in a growth chamber at 18-24° C. under 16/8 hr light/dark cycles. The T0 plants were ready for transformation six days prior to anthesis. Single colonies of *Agrobacterium* carrying the binary constructs, were cultured in LB medium supplemented with kanamycin (50 mg/L) and gentamycin (50 mg/L). The cultures were incubated at 28° C. for 48 hrs under vigorous shaking and then centrifuged at 4,000 rpm for 5 minutes. The pellets comprising *Agrobacterium* cells were re-suspended in a transformation medium containing half-strength (2.15 g/L) Murashig-Skoog (Duchefa); 0.044 μM benzylamino purine (Sigma); 112 μg/L B5 Gambourg vitamins (Sigma); 5% sucrose; and 0.2 ml/L Silwet L-77 (OSI Specialists, CT) in double-distilled water, at pH of 5.7. Transformation of T0 plants was effected by inverting each plant into an *Agrobacterium* suspension, such that the above ground plant tissue was submerged for 3-5 seconds. Each inoculated T0 plant was immediately placed in a plastic tray, then covered with clear plastic dome to maintain humidity and was kept in the dark at room temperature for 18 hrs, to facilitate infection and transformation. Transformed (i.e., transgenic) plants were then uncovered and transferred to a greenhouse for recovery and maturation.

The transgenic T0 plants were grown in the greenhouse for 3-5 weeks until siliques were brown and dry. Seeds were harvested from plants and kept at room temperature until sowing. For generating T1 transgenic plants harboring the genes, seeds collected from transgenic T0 plants were surface-sterilized by soaking in 70% ethanol for 1 minute, followed by soaking in 5% sodium hypochloride and 0.05% triton for 5 minutes. The surface-sterilized seeds were thoroughly washed in sterile distilled water then placed on culture plates containing half-strength Murashig-Skoog (Duchefa); 2% sucrose; 0.8% plant agar; 50 mM kanamycin; and 200 mM carbenicylin (Duchefa). The culture plates were incubated at 4° C. for 48 hours then transferred to a growth room at 25° C. for an additional week of incubation. Vital T1 *Arabidopsis* plants were transferred to a fresh culture plates for another week of incubation. Following incubation the T1 plants were removed from culture plates and planted in growth mix contained in 250 ml pots. The transgenic plants were allowed to grow in a greenhouse to maturity.

Transformation of Micro-Tom tomato plants with putative cotton genes—Tomato (*Lycopersicon esculentum*, var MicroTom) transformation and cultivation of transgenic plants was effected according to Curtis et al. 1995, and Meissner et. al. 2000.

Example 7

Growth of *Arabidopsis* Transformed Plants and Phenotype Characterizations

T1 *arabidopsis* plants were grown as described above and phenotypes were characterized.

PCR analysis of transgenic plants—*Arabidopsis* T2 seeds were sown directly in growth mix contained in 250 ml pots. Positive transgenic plants were screen for kanamycin resistance in two weeks old leaves by PCR. Primers used for PCR amplification of the kanamycin were: 5'-CTATTCGGCTAT-GACTGGGC-3' (forward, SEQ ID NO. 72) and 5'-ATGTC-CTGATAGCGGTCCGC-3' (reverse, SEQ ID NO. 73).

Root performance—In order to visualized root performance, T2 seeds were surface-sterilized by soaking in 70% ethanol for 1 minute, followed by soaking in 5% sodium hypochloride and 0.05% triton for 5 minutes. The surface-sterilized seeds were thoroughly washed in sterile distilled water and then placed in culture plates containing half-strength Murashig-Skoog (Duchefa); 2% sucrose; 0.8% plant agar; 50 mM kanamycin; and 200 mM carbenicylin (Duchefa). The culture plates were incubated at 4° C. for 48 hours then transferred to a growth room at 25° C. till reaching the right size for phenotypic characterization.

TABLE 8

Results
Analysis of *Arabidopsis* T2 plants caring the putative cotton genes

| CT | Putative Gene function | T generation | No of Independent plants | T2 Phenotype |
|---|---|---|---|---|
| CT_11 | Agamous-like MADS-box transcription factor | 2 | 5 | Curled and narrow leaves, with long petioles, roots are longer and denser (FIGS. 5a-c) |
| CT_9 | Hypothetical protein | 2 | 5 | The rosette leaves and the inflorescent are longer and bigger compared to control. The roots are longer and denser. The phenotype resembles the phenotype of *Arabidopsis* plants over expressing expansin as was characterized by Hyung-Taeg Cho and Daniel J. Cosgrove in PNAS u Aug. 15, 2000. (FIGS. 5g-i) |
| CT_20 | MYB-related protein | 1 | 1 | Small rankled and hairy leaves (FIGS. 5d and e) |
| CT_40 | Lipid-transfer protein 3 | 2 | 5 | Longer and curlier leaves (FIG. 5j) |
| CT_22 | Hypothetical protein | | | Narrow leaves, with long petioles (FIGS. 5d and f) |
| CT_81 | APETAL2-like protein | 1 | 1 | The rosette leaves are almost double then wild type (FIGS. 5k and l) |
| CT_1 | hydrolase-like protein | 1 | 6 | Narrow leaves, with long petioles (same as CT_22, not shown) |

Example 8

Growth of MicroTom Transformed Plants and Phenotype Characterizations

Experimental Procedures

Transgenic tomato plants—Plant were transformed as described in Example 6, above. Following transformation, T1 MicroTom tomato plants were grown in mix contained in 1000 ml pots.

TABLE 9

Results
Analyzing Micro-Tom tomato T1 and T2 plants and seeds caring the putative cotton genes

| CT | Putative Gene function | T generation | No of Independent plants | T1 seed hair length (wt 0.3 mm) | T2 Phenotype |
|---|---|---|---|---|---|
| CT20 | MYB-related protein homologue | I | 10 | 0.366 ± 0.006 mm (FIGS. 6c-e) | Small and wrinkled leaves, the trichome on the leaves are longer and denser. (FIG. 6a-b) |
| CT75 | Lipid transfer protein, putative | I | 2 | 0.347 ± 0.019 mm | Big inflorescent |
| CT_6 | Aspartyl protease | 1 | 1 | 0.343 ± 0.019 | |
| CT_82 | MADS box protein-like | 1 | 3 | 0.423 ± 0.013 mm (FIG. 5f) | Normal plants |

Discussion

Examples 1-8

In-silico identification of genes involved in cotton fiber development—Little is known about the genetic control of cotton fiber initiation and elongation. Since both cotton fiber and *Arabidopsis* trichomes are developed from single epidermal cells they are assumed to share similar genetic regulation (Reviewed at Wagner G. J. et. al. 2004). In *Arabidopsis*, a large number of studies have revealed extensive information on the genetic mechanisms regulating trichome initiation and elongation. Several studies demonstrated the similarities between trichome and fiber by showing that cotton fiber specific promoters in *arabidopsis* and tobacco plants confer trichome specific expression (Kim and Triplett, 2001; Hsu et. al. 1999; Liu et. al. 2000, Wang et al. 2004). Most of the research that studies fiber development uses *arabidopsis* trichome as a model system to identify cotton genes in a small scale manner (Kim and Triplett, 2001; Wang et al. 2004).

In this study the present inventors have used tomato trichome and flower EST libraries as model systems to study cotton fiber development. Analysis of the EST libraries profile of the tomato homologous clusters to known *arabidopsis* trichome genes showed that tomato trichome and flower EST libraries significantly contributed to this set of clusters.

This result was confirmed while analyzing the EST libraries profile of the new cotton clusters that were selected by their RNA expression pattern as cotton fiber genes. 9 and 10 clusters contained ESTs which originated from the flower and trichome libraries respectively. Furthermore the group of tomato trichome clusters (trichome ESTs/total ESTs>0.1) comprise large portion from the tomato genes that show high degree of homology to cotton (~50%) even though their percentage in the total population is only ~5%. It may indicate that both organ share common developmental processes. Even though there is a large group of studies about the genetic control of tomato fruit and trichome development no publications could be found to use these organs as a source of genomic data to study cotton fiber development. All of the 23 cotton genes were compared to unique EST data produced separately from embryo and suspensor of Scarlet Runner bean developing seeds (World Wide Web (dot) mcdb (dot) ucla (dot) edu/Research/Goldberg/ests/intro-index (dot) htm). All sequences, except one, share high homologies with sequences originated from the suspensor, which is a maternal tissue. This result supports the in silico results and identifies the role of these cotton clusters in fiber development, which originated from maternal cells as well.

Identifying cotton genes with a role in fiber development through analysis of RNA expression profile—The differentiation/initiation phase is represented by gene expression at or before anthesis. The elongation phase mainly in hirsutum cultivars is represented by very fast growth rate mainly during 5 to 20 DPA. One pattern is represented by genes such as CT 1, 2, 3 expressed at their highest levels, slightly before and during the period of peak fiber expansion about 20 DPA. Another pattern of gene expression is displayed by the CT40, 11 or 70 which have the same expression level throughout all fiber development. Likewise, known genes encoding actin, endoxyloglucan transferase or Suc synthase also display unvarying RNA levels throughout fiber development (Shimizu et al., 1997).

Since the initiation occurs mainly before anthesis till 1 DPA it suggests that genes with a peak in expression during this time may have a role in fiber initiation. CT 4, 20, 22 and 11 have expression patterns that indicate their involvement at this stage.

One limitation of the current cotton EST database is the absence of ESTs that were extracted from flower at initiation stage (there is one library that was taken from ovary 1 DPA but of poor quality) most ESTs were taken only later on, between 6 to 10 DPA. This EST composition could explain why most of the chosen genes have expression pattern that indicate their association with the elongation stage.

Role of the selected genes in fiber development, possible mechanisms—The 23 fiber-associated clusters could be classified into 6 functional categories according to their sequence homology to known proteins and enzymes (Table 3, above). The classification was made according to the GO consortium (World Wide Web (dot) geneontology (dot) org/). The largest group comprises unique sequences without homology to any known protein. The rest of the clusters were classified according to categories known to be associated with fiber development. Two genes (Table 3, above) were classified into a cell fate commitment category: a new gene that belongs to the MYB transcription factor and a cotton homologous gene to GL3 that are known to be involved in trichome development in *arabidopsis*. The expression pattern of both genes and the phenotype of CT20 transgene both in *arabidopsis* and tomato T1 plants support their involvement mainly in the initiation phase.

Accumulative evidence link cotton MYB genes with fiber development (Suo. J. et. al. 2003, Cerdoni. M. L. et. al. 2003, Loguerico L. L. et al 1999). Over expression of a number of genes that work in the same pathway related to the initiation phase, could further induce initiation. Kirik et al. (2004) showed that by over-expressing two or three genes from the initiation phase they enhance the number of trichome and root hairs. Genes that relate to the initiation phase could be used for uniformity of fiber initiation on the cotton seed, initiate of more of the seeds epidermis cells into fibers. Over expression of those genes in vegetative meristems such as stems and leaves could be used as protect against insects (as has been shown in canola, World Wide Web (dot) westerngrains (dot) com/news/nr_050413 (dot) html) and a-biotic stresses. However, there is no substantial evidence that proves direct involvement of any MYB gene to fiber development.

Two other genes (Table 3, above) are transcription factors from the MYB and MADS BOX families. Many studies demonstrated the function of these two transcription factor families as homeotic genes with key role in different developmental processes, among them are trichome and fiber morphogenesis (Suo. J. et. al. 2003, Ferrario S et. al. 2004). Their role in early stages of fiber development is supported also by their RNA expression pattern, which, is induced before, and during the day of anthesis. One gene (CT_2, Table 3, above) was classified to the pathways of starch and sucrose metabolism. A recent work demonstrates that another gene (SUS), which, belongs to this pathway, is a limiting factor in both fiber initiation and development. CT_40, 75 were classified as lipid transport whose RNA expression is highly induced during early fiber elongation stage fit to the fact that lipids are key components in fiber formation. Several genes (Table 3, above, CT_4, 70, 71) were classified either as genes involved in desiccation, salinity response stimulated by abscisic acid and genes involved in electron transfer. Out of them 3 genes (CT 7, 9 and 49) were selected by RNA expression pattern to be induced in the elongation stage. Several studies consider changing proton and potassium pump mechanisms as key factor in the rapid growth rate of the fiber (Smart L. B, et. al. 1998). Combine the over-expression of several genes relate to fiber elongation such as genes relate to starch and sucrose metabolism that will enhance cell wall formation with lipid transport genes or genes relate to desiccation that my influence on the pressure in the cell, might result in longer fibers then over expressed of single gene.

Example 9

Cloning and Analyses of Promoter Sequences Upstream of the Genes of the Present Invention Differential gene expression in fiber tissues vs. other tissues in cotton is the result of complicated gene regulation. The genomic regions upstream of the 23 selected genes are predicted to possess promoter activities that direct gene expression to fiber cells in unique quantitative and qualitative manner. A precise gene expression, directed to fiber cells, is crucial for the development of cotton plants with enhanced fiber performance, without negatively affecting other plant tissues.

Experimental Procedures

Cloning of promoter sequences—The genomic sequence upstream of CT2 and CT6 were cloned from genomic DNA of cotton (*Gossypium hirsutum* L. var Acala), as follows. Total genomic DNA was extracted from plant leaf tissues of 4 week old cultivated cotton plants (*Gossypium hirsutum* L., var Acala), using DNA extraction kit (Dneasy plant mini kit, Qiagen, Germany). Inverse PCR (IPCR), DNA digestion, self-ligation, and PCR reaction were performed on genomic DNA, following common protocol (World Wide Web (dot) pmci (dot) unimelb (dot) edu (dot) au/core_facilities/manual/mb390 (dot) asp) with the following modifications. To avoid mistakes in the IPCR, the genomic sequence of the 5' sequence of a relevant cDNA (i.e. including introns) was first identified to produce Genomic Island (GI). The desired region from the genomic DNA was PCR-amplified using direct oligonucleotide primers designed based on the cDNA cluster sequence (for CT_2 and CT_6, respectively GI sequences are as set forth in SEQ ID NOs. 74 and 75 for CT_2 and CT_6. Primers are set forth in SEQ ID NOs. 14-15 (CT_2) and 101-102 CT_6). PCR reaction was performed in a DNA thermal cycler, using common PCR protocols. For example:

92° C./3 min 31×[94° C./30 sec→56° C./30 sec→72° C./3 min]→72° C./10 min).

PCR products were purified using PCR purification kit (Qiagen) and sequencing of the amplified PCR products was performed, using ABI 377 sequencer (Amersham Biosciences Inc).

In some cases, a different technique [UP-PCR (Dominguez and Lopez-Larrea. 1994)] was used when IPCR resulted in poor amplification. UP-PCR technique was used in order to amplify unknown upstream region of known cluster sequences. Generally, the procedure involved four oligo-nucleotide primers: two sequence specific primers (SPs, external and internal) (listed below), both with same orientation of 3' end towards the unknown, yet desired, 5' region of the gene, and two universal walking primers (WP28 5'-TTTTTTTTTTGTTTGTTGTGGGGGTGT (SEQ ID NO. 76 and sWP 5'-TTTTTGTTTGTTGTGGG, SEQ ID NO. 77). Reactions were carried out using the following reaction mixtures: sample mixture (SM)—genomic DNA of cotton species (30-40 ng), WP28 primers (20 pmol), and double distilled water was added to a final volume of 10 µl. Polymerase mixture (PM)—dNTPs (Roche, Switzerland, 10 nmol each), Expand Long Template Enzyme mix (Roche, Switzerland, 1 U), 10× buffer supplied with the enzyme and double distilled water was added to a final volume of 8 µl.

SMs were placed in a thermocycler (Biometra, USA), where it was subjected to an amplification program of 1 minute at 90° C., held (pause) at 80° C. until PM was added, 30 seconds at 15° C., 10 minutes at 25° C., 3 minutes at 68° C., held at 90° C. until the external SP (2 µl of 10 µM concentration) was added. The process was followed by external PCR reaction of 30 seconds at 92° C., 10 seconds at 94° C., 30 seconds at 65.5° C., 3 minutes at 68° C., for 30 cycles followed by final extension of 10 minutes at 68° C.

External PCR product diluted 5000-25000 fold was used as a template, and PCR amplification was effected using specific internal sWP and SP (30 pmol each) primers, 1 U Ex Taq (Takara), in 50 µl reaction volume. Internal PCR reaction was subjected to an amplification program of 2 minutes at 92° C., followed by 30 seconds at 94° C., 30 seconds at 58° C., and 3 minutes at 72° C. for 30 cycles and a final extension of 10 minutes at 72° C. IPCR/Up-PCR products were purified (PCR Purification Kit, Qiagen, Germany) and sequenced (ABI 377 sequencer, Amersham Biosciences Inc).

Primers for CT_2 were as follows (UP-PCR):

```
External primers:
                                      (SEQ ID NO. 78)
sWP28-5'-TTTTTTTTTTGTTTGTTGTGGGGGTGT-3'

(SEQ ID NO: 79)
SP (External)-5'-CTGGGGTTACTTGCTAATGG-3'

Internal (Nested) primers:
                                      (SEQ ID NO: 80)
sWP-5'-TTTTTGTTTGTTGTGGG-3'

(SEQ ID NO: 81)
SP (Internal)-5'-GCTCCGGGCTTTGGTTAACG-3'
```

Internal genomic sequence of CT_2 resulting from the above procedure is provided in SEQ ID NO: 14.

Primers for CT_6 were as follows (UP-PCR):

```
External primers:
                                      (SEQ ID NO. 78)
sWP28-5'-TTTTTTTTTTGTTTGTTGTGGGGGTGT-3'

(SEQ ID NO: 82)
SP (External)-5'-GGCTTTGGGATGTTTGAGGTGG-3'

Internal (Nested) primers:
                                      (SEQ ID NO: 83)
sWP-5'-TTTTTGTTTGTTGTGGG-3'

(SEQ ID NO: 84)
SP (Internal)-5'-GGTGGTGGGCTCTTGCAACAG-3'
```

Internal genomic sequence of CT_2 resulting from the above procedure is provided in SEQ ID NO: 85.

For cloning the putative promoters and 5' UTRs, PCR amplification was carried out using a new set of primers (below) to which 8-12 bp extension that included one restriction site (HindIII, SalI, XbaI, BamHI, or SmaI) on the 5' prime end. For each promoter, restriction sites that do not exist in the promoter sequence were selected. Moreover, the restriction sites in the primer sequences were design so the resultant PCR products will be cloned into the binary vector pPI in the right orientation, upstream of the GUS reporter gene.

The plasmid pPI was constructed by inserting a synthetic poly-(A) signal sequence, originating from pGL3 basic plasmid vector (Promega, Acc No U47295; bp 4658-4811) into the HindIII restriction site of the binary vector pBI101.3 (Clontech, Accession No. U12640).

Below are the primers used for promoter and 5' UTR (P+U) amplification and cloning into pPI, and the amplified and cloned sequence. Restriction sites within each primer are shown in bold letters:

```
CT_2:
P + U forward (HindIII):
                               (SEQ ID NO: 86)
5'-ATTCAAGCTTTTTTGTTTGTTGTGGGGG-3'

P + U reverse (BamHI):
                               (SEQ ID NO: 87)
5'-TTGGATCCTTGGGCATTGAGCTTCTGTAC-3'

P + U sequence of CT_2 is as set forth in

SEQ ID NO: 88.

CT6:
P + U forward (HindIII):
                               (SEQ ID NO: 89)
5'-TTAAAGCTTTGGGCTCTTGCAACAGAGGC-3'

P + U reverse (BamHI):
                               (SEQ ID NO: 90)
5'-AAGGATCCGACGACGACAACAACAACAAC-3'

P + U sequence of CT_6 is as set forth in

SEQ ID NO: 91.
```

Genomic DNA or the IPCR/UP-PCR product was used as DNA template for PCR-amplification, using the newly designed oligonucleotide primers. PCR products were purified (PCR Purification Kit, Qiagen, Germany) and digested with the restriction sites exist in the primers (Roche, Switzerland). The digested PCR products were re-purified and cloned into the binary vector pPI, which was digested with the same restriction enzymes. PCR product and the open plasmid vector were ligated using T4 DNA ligase enzyme (Roche, Switzerland).

Example 10

Transforming *Agrobacterium* Tumefacience Cells with Binary Vectors Harboring Cotton Fiber Promoters pPi Binary vector, including either CT2 or CT6 promoter, upstream to the GUS reporter gene were used to transform *Agrobacterium* cells.

The binary vectors were introduced to *Agrobacterium tumefaciens* GV301, or LB4404 competent cells (about $10^9$ cells/mL) by electroporation. Electroporation was performed using a MicroPulser electroporator (Biorad), 0.2 cm cuvettes (Biorad) and EC-2 electroporation program (Biorad). The treated cells were cultured in LB liquid medium at 28° C. for 3 hr, then plated over LB agar supplemented with gentamycin (50 mg/L; for *Agrobacterium* strains GV301) or streptomycin (300 mg/L; for *Agrobacterium* strain LB4404) and kanamycin (50 mg/L) at 28° C. for 48 hrs. *Agrobacterium* colonies which developed on the selective media were analyzed by PCR using the primers set forth in SEQ ID NOs: 70-71, which were designed to span the inserted sequence in the pPI plasmid. The resulting PCR products were isolated and sequenced as described in Example 4 above, to verify that the correct sequences were properly introduced to the *Agrobacterium* cells.

Example 11

Cotton Fiber Specific Promoters are Expressed in Tomato Leaves and Tomato Fruits GUS staining was effected to illustrate specific expression in trichomes and tomato fruits.

Experimental Procedures

Transformation of Micro-Tom tomato plants with putative cotton promoter—As describe above.

Transformation of *Arabidopsis thaliana* plants with putative cotton promoter—As describe above.

GUS staining of *Arabidopsis*-Gus staining of *arabidopsis* plants was effected as previously described (Jefferson R A. et. al. 1987, Meissner et. al. 2000).

GUS staining of tomato leaves—Gus staining of tomato plants was effected as previously described (Jefferson R A. et. al. 1987, Meissner et. al. 2000).

Tissue fixation was effected as follows. Tomato leaves were immersed in 90% ice cold acetone, then incubated on ice for 15-20 minutes following by removal of the acetone. Thereafter tissue was rinsed twice with the Working Solution [100 mM Sodium Phosphate (Sigma, USA) buffer pH=7, Ferricyanide (Sigma, USA) 5 mM, Ferrocyanide (Sigma, USA) 5 mM, EDTA (BioLab) pH=8 1 mM, Triton X-100 (Sigma, USA) 1%] for 15-20 minutes in dark. Rinsing solution was then removed and replaced with X-gluc staining solution [Working Solution+5-bromo-4-chloro-3-indolyl-β-D-glucuronic acid (X-GlcA, Duchefa) solubilized in N,N-Dimethylformamide (BioLab) 0.75 mg/ml, Dithiothreitol (BioLab) 100 mM] and incubated for over night at 37° C. in the dark (tubes wrapped with aluminum foil). Distaining was effected by sinking the plant tissue in 70% ethanol and heating at 50° C. for ~120 minutes. Distaining step was repeated until the plant tissue became transparent excluding the blue stained regions. Distained plants were stored in 70% ethanol (BioLab) at room temperature.

GAS staining of Tomato Fruits—Gus staining of tomato fruits was effected as previously described (Jefferson R A. et. al. 1987, Meissner et. al. 2000). Briefly: thin tomato fruit slice were sunk in staining solution [100 mM Sodium Phosphate (Sigma, USA) buffer pH=8, Ferricyanide (Sigma, USA) 5 mM, Ferrocyanide (Sigma, USA) 5 mM, EDTA (BioLab) pH=8 15 mM, Methanol (BioLab) 20%, 5-bromo-4-chloro-3-indolyl-β-D-glucuronic acid (X-GlcA, Duchefa) solubilized in N,N-Dimethylformamide (BioLab) 0.75 mg/ml] in the dark (tubes wrapped with aluminum foil) and incubated for over night at 37° C. Distaining was effected by sinking the plant tissue in 70% ethanol and heating to 50° C. for ~20 minutes. Distaining step was repeated until the fruit slice became transparent except for the blue stained regions. Distained fruits were stored in 70% ethanol (BioLab) at room temperature.

Results

GUS Staining was Performed on Seeds of T1 Tomato Plants.

GUS was expressed under the regulation of CT2 and CT6, promoters in the genetically transformed tomato plants (FIGS. 7a-b).

Results for tomato T1 generation are summarized in the Table 10, below.

TABLE 10

| Promoter | No of Independent T1 plants | Leaf | Leaf trichome | Seed cover of Young fruit | Seed cover of Mature green | Seed cover of Ripen fruit |
| --- | --- | --- | --- | --- | --- | --- |
| CT2 | four | 0 | 2 | 3 | 5 | 3 |
| CT6 | one | 0 | 1 | 1 | 2.5 | 1 |

The numbers represent average grade, 0-not expressed, 5-high expression

Example 12

Tomato Seed Hairs as a Model System for Cotton Fibers

The genetic modification of cotton is long and time consuming. Hence to find genes which are capable of improving cotton fiber yield and quality, a need exists for a model system for cotton fiber development in other plants.

Trichome cells and root hairs share common characteristics with cotton fiber cells, and are widely accepted as model systems for cotton fiber development [Reviewed in Wagner. G. J. et. al. 2004) and Wang et al. 2004].

However measuring changes in growth rate, length and thickness as well as other structural parameters is not an easy task because of the small size, remote accessibility and lack of uniformity in sizes of trichome cells.

To overcome these limitations, tomato seed hairs were analyzed for their possible use as a model tissue for cotton fiber development. To this end, the GUS reporter gene was over-expressed under the regulation of cotton fiber specific promoter element derived from CT2, as describe above.

Tomato transformation of the binary construct, plant regeneration and GUS staining was effected as described above.

Tomato seed hairs (FIG. 8a) are maternal epidermal cells, covering the ovule surface of the seeds. In anatomical aspects, tomato seed hairs are much closer to cotton fibers than either trichome cells or root hairs.

4 independent transgenic tomato fruits over-expressing GUS gene under cotton specific promoter CT_2 were produced. GUS staining of fruits at the mature-green stage (fruit is in full size just before the ripening process) was observed uniquely on the seed envelope, where seed hairs are being developed (FIGS. 7a and b).

Five independent transgenic tomato fruits over-expressing 35S-expansin (AF043284) were produced, and the seed hair length was measured and compare to wt. The seed hair of transgenic plants was significantly longer than of wt (FIGS. 8a-b).

TABLE 11

| Plant | Number of Independent plant | Seed hair length (mm) |
| --- | --- | --- |
| WT | 3 | 0.300 ± 0.019 |
| 35S:expansin | 5 | 0.357 ± 0.017 (FIG. 8b) |

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

REFERENCES CITED BY AUTHOR NAME IN THE APPLICATION

Other References are Cited in the Document

Cedroni M. L, Cronn R. C, Adams K. L, Wilkins T. A, and Wendel J. F. 2003. Evolution and expression of MYB genes in diploid and polyploid cotton. Plant Mol. Biol. 51, 313-25.

Clough S. J, and Bent A. F (1998). Floral dip: a simplified method for *Agrobacterium*-mediated transformation of *Arabidopsis thaliana. Plant J.* 16, 735-43.

Curtis I. S, Davey M. R, and Power J. B. 1995. Leaf disk transformation. *Methods Mol. Biol.* 44, 59-70.

Desfeux C, Clough S. J, and Bent A. F (2000). Female reproductive tissues are the primary target of *Agrobacterium*-mediated transformation by the *Arabidopsis* floral-dip method. *Plant Physiol.* 123, 895-904.

Dominguez O, and Lopez-Larrea. C. 1994. Gene walking by unpredictably primed PCR. *Nucleic Acids Research.* 22:3247-3248.

Hsu C. Y, Creech R. G, Jenkins J. N, and Ma D. P. 1999. Analysis of promoter activity of cotton lipid transfer protein gene LPT6 in transgenic tobacco plants. *Plant Sci* 143, 63-70.

Kim H. J, and Triplett B. A. 2001. Cotton fiber growth in planta and in vitro. Models for plant cell elongation and cell wall biogenesis. Plant Physiol. 2001 December; 127 (4): 1361-6.

Larkin J. C, Brown M. L, and Schiefelbein J. 2003. How do cells know what they want to be when they grow up? Lessons from epidermal patterning in *Arabidopsis. Ann. Rev. Plant Mol. Biol.* 54, 403-430.

Liu H. C, Creech R. G, Jenkins J. N, Ma D. P. 2000. Cloning and promoter analysis of the cotton lipid transfer protein gene Ltp3(1). *Biochim Biophys Acta* 24): 106-11

Loguerico L. L, Zhang J. Q, and Wilkins T. A. 1999. Differential regulation of six novel MYB-domain genes defines two distinct expression patterns in allotetraploid cotton (*Gossypium hirsutum* L.). *Mol. Gen. Genet.* 261, 660-71.

Meissner R, Chague V, Zhu Q, Emmanuel E, Elkind Y, Levy A. A. 2000. Technical advance: a high throughput system for transposon tagging and promoter trapping in tomato. *Plant J.* 22, 265-74.

Ruan Y. L, Llewellyn D. J, and Furbank R. T. 2003. Suppression of Sucrose Synthase gene expression represses cotton fiber cell initiation, elongation and seed development. *Plant Cell* 15, 952-964.

Schellmann. S, Schnittger. A, Kirik. V, Wada. T, Okada. K, Beermann. A, Thumfahrt. J, Jurgens. G, and Hulskamp. M. 2002. *TRIPTYCHON* and *CAPRICE* mediate lateral inhibition during trichome and root hair patterning in *Arabidopsis*. *EMBO J.* 21, 5036-5046.

Smart L. B, Vojdani F, Maeshima M, Wilkins T. A. 1998. Genes involved in osmoregulation during turgor-driven cell expansion of developing cotton fibers are differentially regulated. *Plant Physiol.* 116, 1539-49.

Suo. J, Liang. X, Pu. Li, Zhang. Y, and Xue. Y. 2003. Identification of GhMYB109 encoding a R2R3 MYB transcription factor that expressed specifically in fiber initials and elongating fibers of cotton (*Gossypium hirsutum* L.). *Biochem. Biophys. Acta* 1630, 25-34.

Wagner. G. J, Wang. E and Shepherd. R. W. 2004. New approaches for studying and exploiting an old protuberance, the plant trichome. *Ann. Bot.* 93, 3-11.

Wang E, Gan S, and Wagner G. J. 2002. Isolation and characterization of the trichome-specific promoter from *Nicotiana tabacum* L. *J Exp Bot.* 53(376):1891-7.

What is claimed is:

1. A transgenic plant cell comprising a nucleic acid construct which comprises a polynucleotide encoding the polypeptide having the amino acid sequence set forth in SEQ ID NO: 123 and at least one cis-acting regulatory element operably linked to said polynucleotide.

2. A transgenic plant comprising the transgenic plant cell of claim 1.

3. A method of improving fiber quality or yield of a fiber producing plant, the method comprising expressing within cells of a plant an exogenous polynucleotide encoding a polypeptide having the amino acid sequence set forth in SEQ ID NO: 123, thereby improving the quality and/or yield of the fiber producing plant.

4. The method of claim 3, wherein the quality of the fiber producing plant comprises at least one parameter selected from the group consisting of fiber length, fiber strength, fiber weight per unit length, maturity ratio, uniformity and micronaire.

5. The method of claim 3, wherein said fiber producing plant is selected from the group consisting of cotton, silk cotton tree (Kapok, *Ceiba pentandra*), desert willow, creosote bush, winterfat, balsa, ramie, kenaf, hemp, roselle, jute, sisal abaca and flax.

6. A method of increasing the biomass of a plant, the method comprising expressing within cells of a plant an exogenous polynucleotide encoding a polypeptide having the amino acid sequence set forth in SEQ ID NO: 123, thereby increasing the biomass of the plant.

7. The method of claim 6, wherein the plant is a monocot plant.

8. The method of claim 6, wherein the plant is a dicot plant.

9. A method of producing cotton fibers, the method comprising:
(a) generating a transgenic cotton plant expressing an exogenous polynucleotide encoding a polypeptide having the amino acid sequence set forth in SEQ ID NO:123, and
(b) harvesting the fibers of said transgenic cotton plant, thereby producing the cotton fibers.

10. The transgenic plant cell of claim 1, wherein said polynucleotide is at least 95% identical to the nucleic acid sequence set forth in SEQ ID NO:21.

11. The transgenic plant cell of claim 1, wherein the nucleic acid sequence of said polynucleotide is set forth in SEQ ID NO:21.

12. The method of claim 3, wherein said exogenous polynucleotide is at least 95% identical to the nucleic acid sequence set forth in SEQ ID NO:21.

13. The method of claim 3, wherein the nucleic acid sequence of said exogenous polynucleotide is set forth in SEQ ID NO:21.

14. The method of claim 6, wherein said exogenous polynucleotide is at least 95% identical to the nucleic acid sequence set forth in SEQ ID NO:21.

15. The method of claim 6, wherein the nucleic acid sequence of said exogenous polynucleotide is set forth in SEQ ID NO:21.

16. The method of claim 9, wherein said exogenous polynucleotide is at least 95% identical to the nucleic acid sequence set forth in SEQ ID NO:21.

17. The method of claim 9, wherein the nucleic acid sequence of said exogenous polynucleotide is set forth in SEQ ID NO:21.

* * * * *

SEQUENCE LISTING

```
<160> NUMBER OF SEQ ID NOS: 126

<210> SEQ ID NO 1
<211> LENGTH: 1086
<212> TYPE: DNA
<213> ORGANISM: Gossypium hirsutum

<400> SEQUENCE: 1
cccgggatgg atggttattg tagcagaagg gtaatcatgt ttttggtgtt tgcatttgca      60
gcaataagca gagggtatgg acaagaatca accactcttg ttcctgcaat catcaccttt     120
ggtgactctg tggtagatgt gggcaataat gactatctcc ctaccatctt caaggctaac     180
tatcctcctt atggacggga ctttgccaac aaaaagccta ctgggaggtt ttgcaatgga     240
aaattagcca ctgacatcac tgctgaaact ctggggttta caacttatcc accagcttac     300
cttagcccag aagcatcagg gaagaacctt ctgcttggag ccaattttgc ttcagctggc     360
tctggctatg atgacaaagc tgccatggtg aatcatgcca tcacattgac ccagcaatta     420
gagtatttca aggaatacca ggcaaagcta gcaaaggtag caggcagcac caaatcagca     480
tccattacca aggatgcact gtatgtattg agtgcaggaa gcggtgactt cctccagaac     540
tactatgtca accctctact taaccatgcc tatactccag accagtacgg ctcattcctt     600
attgatacct tcacaaactt cgtcaagaac ctctatgggt tgggagctag gaaaattggg     660
gttacctcac ttccaccgtt aggttgcgtt ccattagcaa gaacattgtt cggttaccac     720
gagaaaggat gcatctccag gttcaatacc gatgctcaac aattcaataa aaagctcaac     780
gccgcagcag ccaatctcca gaagcagcat cctggtctta agattgtggt tttcgacata     840
ttcaaggcac tttacgacat tgttaaatct ccctctaact atggttttgt tgaagcaaca     900
aaagggtgtt gtggaactgg aacagtagag acaaccgcat ttttgtgcaa tccaaaggca     960
ccaggaactt gttccaatgc cagccaatat gtattttggg acagtgttca tccatctcag    1020
gctgctaatc aagtccttgc agatgcattg attgttcagg gcattgccct catttgattc    1080
gagctc                                                              1086

<210> SEQ ID NO 2
<211> LENGTH: 1975
<212> TYPE: DNA
<213> ORGANISM: Gossypium hirsutum

<400> SEQUENCE: 2
tctagacaag tacagaagct caattcccaa gatggaggcc agcagcagca cctcccatga       60
```

-continued

```
cccagcattg ttccatgctc ccttgctata ccaccctcgg agaaggagca gcagaccctt    120
aaagggtttc gcagtgataa ttgggtccgt cgttttccta ctctcactgg tcacattaat    180
cgttaaccaa agcccggagc cattagcaag taacccagt agtgtaacgg aggcagggtc     240
gtattcaatg gcggcgcagc caagagggat agctgaaggt gtttcagcca agtcaaaccc    300 atcactttt gacaaagttg ggtttaattg gacaaacgct atgttttact ggcaaagaac     360
tgcctaccac tttcagcctc aaaagaattg gatgaatgat cctgacggtc cgttatatca    420
caagggatgg taccatcttt tctatcaata caacccctgat tcagccatat ggggaaacat   480
cacttggggc cacgctgtat caacggacct cattcactgg ttctatctcc cactcgccat    540
ggtccctgat caatggtacg atatcaacgg ttgttggacg gggtcggcca ctctcctgcc    600
agatggccga atcgtaatgc tttacaccgg cagcaccaat gactccgtgc aagtccaaaa    660
ccttgcatat cccgccaacc tatctgatcc cctcctcctt cagtggttaa ataccggg     720 taacccggtt gttgttcccc caaccgggat cgaagacgaa gagttccgag acccgacaac    780
agcttggctt ggacccgatg gttcctggcg gattgttgtt ggtacaaggt ttaataccac    840
cataggaaca gcccttgttt ttcaaacgac aaacttttcg gactatgaat tattggatgg    900
ggtcttacat gctgttccgg gtacgggtat gtgggaatgt gtagattttt accccgttgc    960
aataaacggg tcggtcggac tggacacgac ggcacttggg cctggaatta agcatgtcct   1020
gaaggctagt ttggatgata cgaaagttga tcattatgca ataggaccct acgacatgat   1080
aacggataaa tggacacctg ataacccgga agaagatgta ggcatcgggt tgaaagtgga   1140
ttatgggaga tactatgcct ccaagacatt ttttgatcag agtaaacaaa ggaggattct   1200
ttatggttgg gttaatgaaa ctgattctga agctgatgac ctcgaaaaag gatgggcttc   1260
cattcagaca attcccagga gtgtgttgta tgacaacaag accggaaccc atttactaca   1320
gtggcctgtg gaagaagtgg agagcttgag actgaatgct acagtgttta aggatgttgt   1380
agttgaagca ggatcagttg tgcccctcga cataggcacc gctactcagt tggatatatt    1440
agcagagttt gaaatagaga cgttggtatt gaacagcacg gaggatgaag tcagtgattg    1500
cggtgatggg gcggttgata ggagcactta cgggccattt ggggtcctgg ttattgctga    1560
tgattcactt tctgagctca ctcctatata tttccgtcca cttaatacat ccgatgggag    1620
tcttgaaact tactttttgcg ctgacgaaac aaggtcttct aaagctcccg atgtcacaaa    1680
acgagtgtat ggaggcaaaa ttccagtgct tgacgatgaa aactacaaca tgagggtatt    1740
ggtggatcat tcagtagtgg aaagttttgg aggaggaggg aggacggtga acatcaag      1800 agtgtatcca acgaagcca tatatggagc agcacggctg ttcttgttca acaatgcaag    1860
tggagtgaat gtgaaggcca cactcaaaat atgggagatg aattctgcct ttattcgtcc    1920
tttcccattt gaagaaacat tatttcagga aatggttgct tccacatgat tatca         1975
```

<210> SEQ ID NO 3
<211> LENGTH: 560
<212> TYPE: DNA
<213> ORGANISM: Gossypium hirsutum

<400> SEQUENCE: 3

```
cccgggtgat ggaactgagc attcagaaaa tagaagcctt gattaggcta agtacgatag     60
tgatgttggt tttaacagct tgtttaattg ggttggattc tcaaacaaag gtcatcttct    120
acgttcaaaa gaaagcttct ttcaaggatt tgcgtgctct tgttggattg ctgtatatca    180
```

```
cttcattggc tgctgcttat aatctacttc aactatgctg ttcttcattc tcagcttctt    240
acaaaggaac ctcgctgcaa tcttacgcat atctggcttg gcttcgttat attttggatc    300
aggcagtagt gtacgcagtg tttgcgggaa acctagcggc tttggagcat tcattttttgg   360 tattaaccgg agaagagaac ttccaatggc tcaagtggtg caataaatat actcgattct    420
gcacccaaat cggaggatcc ttgctctgcg gcttcgttgc aagcttacta atgttttcca    480
tcgcttccat ctccgcattc aacttgttca ggctgtattc ccccaccaag ttcatgcact    540
tgaaactcta atcagagctc                                                560

<210> SEQ ID NO 4
<211> LENGTH: 1143
<212> TYPE: DNA
<213> ORGANISM: Gossypium hirsutum
<220> FEATURE:
<221> NAME/KEY: misc_feature
<222> LOCATION: (24)..(24)
<223> OTHER INFORMATION: n is a, c, g, or t

<400> SEQUENCE: 4
tgtgtataaa tatgtagaca cagnagatcc aatatatttt cactttcaca gcaaccttct     60
tctccactcc tccatctata tatatagtta gaggcagaag ggaggaagtg acattggcaa    120
tatggctttg ctgcattctt acttcttaag cgctggtgag tatgtttcag ggtccacggt    180
cttggcagtg gcaatgtcca ttgcttccta ttttctgatc cctatggtgt ttggtggtcg    240
ccataaaaac tggaagaatg caccaccagg ccctgttggt tggcctatcc ttggcagcct    300
tccacacctc tccaatcgtc tccatgaaga tttctttgac atggccaagg tctacggtcc    360
ccttttcagt ctaaacttgg gaataaagcc ggccatagtg gtgtcatcac cggaaatggc    420
agcccaagtt ttgaaggaaa aggaagggat gttctccagt cggaccataa ccgagaccat    480
tcgagtcatc tcttatgatg cccattccat cattttctcg ccctatggtc ccaggtggaa    540
ggttcttcga aggatcttga tcaccgaact actttctcct aaggcctttg aacaatttga    600
gccacttcgt acctcacagg ttcatggttt gctcaagtat ttgtacttgg tctcaaagtc    660
caacactcaa gtgaacatag cagaatatgc ttttacagca ctggccaacc tagtgagtaa    720
tttcgtctgc tccaaggacc ttttcgacaa ctcaatgcct gaaggaagaa aaatgaaaga    780
gaggttctgg gagttgataa aggtgattgg gaccccgaat ttttctgatc tcattccatt    840
tgttaaacca tttgatccac aaggccttga agagaaaaat caacaagatc tycggacagt    900
tggatgcttt ctatgagaag tatatcgagg agaagtttgc tgacaaggga aaagctcaac    960
ttgatgggac gataccctac caacggaaaa atggatatgt tagatgttct gttgagttat   1020
gagaagaatt gataaacaaa atgggtttgg acccgtttac cacaatccta tcgtccaaag   1080
gaatgctttt ctgaaaatgg ttaattggca gcgaactgaa aaacacccct caacgcacct   1140
ggg                                                                 1143

<210> SEQ ID NO 5
<211> LENGTH: 1464
<212> TYPE: DNA
<213> ORGANISM: Gossypium hirsutum

<400> SEQUENCE: 5
cccgggttgt tgtcatggct tctctgcctt tcatcttctt cttatctttc tttataatct     60
ccacaacatt gacgtcagcc ggcgccgccg ccgccaccat caaactctcc ctctctccct    120
tccctcaccc ttcttcctcc catccttacc aaattctcaa caacttagtc acttcttctg    180
```

-continued

```
ttgcaagagc ccaccacctc aaacatccca aagccaaggc cgataatact acctcttctc    240
ttctcagggc tcccctattt tctcacagtt atggggcta cactatctcc ctcaaatttg    300
gaactccgcc tcaaaccctt cctttcgtca tggacaccgg gagcagcctc tcctggttcc    360
cttgcacctc tcgttacctt tgttcccaat gcgcattccc caatgttgac cctgcaaaaa    420
tccccacttt tgcccctaaa ctttcatctt ccagtaagct cgtaggttgt agaaacccca    480
agtgtagttg cttttttggc cccgacgttg agtctcgttg ccaagactgt gaacccactt    540
ccgaaaactg cactcaaacc tgccctcctt acataattca atacggttta ggttccactg    600
ctgggcttct attagtagaa aaccttgctt tcccccagaa aaccttccaa gatttccttg    660
tcggatgctc catcctctcc aaccgacagc ccgctggaat agccgggttc ggtcggagcg    720
ctgagtctat accctcccaa ttaggcctca agaaattctc ttactgtctc gtttctcgcc    780
ggttcgatga cactggcgtc agcagcaaca tgttgttgga aaccgggtcg ggttccggtg    840
atgccaagac cccaggcctt agctacacac cgttttacag gaaccaagtg gcttcaaacc    900
cagttttcaa agagttctac tacgtaactc tacgtaaaat tctggtgggc gataagcacg    960
tcaaagttcc gtacagttat ttggtcccag gatcagacgg taacggtggc accatagtgg   1020
actcgggatc aacattcact tttatggaga gaccagtgtt cgaggtagtc tcgaaagagt   1080
tcgagaaaca aatgggaaat tatagaagag tgcgtgaaat agaaaacaga tcgggtttag   1140
ccccatgctt caacacttcg ggctatactt aatagaaat ccccgaattg agtttccagt   1200
tcaaaggagg agccaaaatg gcattgcctt tggttaacta tttctcattt gacggtgatg   1260
ataaggttgt gtgtttgatg atcgtttcaa acaatgtggt cggccaaggc tcacacagcg   1320
gtcctgcaat aatactaggg agctttcagc agcagaatta ttacatcgaa tttgatatcg   1380
caaacaatag gtttggatgg gctgaacgaa gctgtgcgtg agctgcactt tgttatttttg   1440 tgttttggcc atgaatatga gctc                                          1464
```

<210> SEQ ID NO 6
<211> LENGTH: 1402
<212> TYPE: DNA
<213> ORGANISM: Gossypium hirsutum

<400> SEQUENCE: 6

```
cccgggaaag gaaatggcag gcgtcgaagc agggaaggag gaggaggcga ccgctgtgag     60
aatcaccgga aaaagccacg tcaagccggg taagttgata ggaagaaaag agtgtcagtt    120
ggtcacattt gatctcccct acctggcttt ctattataac cagaagctgc tgttttacaa    180
gaacgacggt ggtggtgagt tcgaggacaa ggttgaaaag ctcaagggag ggctgagggt    240
ggtgttagag gagtttttatc agctaggagg taagctcggg aaagatgacg atggggttct    300
tagagttgat tatgacgatg atatggatgg tgttgaagtg gtggaagccg tggcagaggg    360
gattaccgtc gatgaattga ccggtgatga tggtacgagc tcatttaagg aattgatacc    420
ttttaatggc gtcttgaact tggagggtct tcacaggcct cttttgtcca tacagttgac    480
gaagttgaaa gatggtgttg caatgggtgt tgctttcaac catgccatcc tcgacggaac    540
ctccacttgg catttatga gctcttgggc tcaaatctgt aacggtactt cgagctccgt    600
cgttgtgccg ccgtttcttg atcggaccac agctcgaaac cccgcgtga agctcgacct    660 cagtccggtt gtttcctgca acggcgacga cgccaccaaa caaggccagc cggcgccgca    720
gatgagggag aaactcttcc gttttttccga agccgccgtc gataagatca aatcgagagt    780
```

```
taattcaacc ccaccaccgt ccgatggctc taaaccgttc tcgactttcc aatctctagc      840
tgtccacatt tggcgacacg tatcccaagc acgtaacctt aaacccgaag actacacggt      900
ttttactgtc ttcgccgatt gtcgtaaaag ggttgatcca ccgatgcccg acagttactt      960
cggaaacttg attcaagcca tcttcaccgc cacagcggcc gggttgttat tggaaaaccc     1020
accgtcattc ggagcttcag tgatacaaaa agctatagaa tcccacgacg ctaaagccat     1080
cgatgaacgt aacaaggcat gggaagcagc gccgaagatt ttccagttca agacgccgg     1140 tgtcaactgc gtagcggtcg gaagctcccc gaggtttaaa gtttacgaag tggatttcgg     1200
gtggggaaag ccgtaggggg tgaggagtgg atccaacaac aggttcgatg gaatggtgta     1260
tttgtatcaa gggaagagcg gtggccggag cattgacgtt gaaatcacca tggaagctca     1320
agctatggag aaattggaga aggataaaga gttttaatg gaagtatagt attttgcatg     1380
gaagtagggt actgtggatc tc                                              1402

<210> SEQ ID NO 7
<211> LENGTH: 1480
<212> TYPE: DNA
<213> ORGANISM: Gossypium hirsutum

<400> SEQUENCE: 7
cccgggtacc attactctac tacagctgct atcattacta catacatgtc cacccaaagt       60
cgagcagttg gcggcaccga gcacaactgg tgccgagcgg tggtcggggg aaccgggata      120
gccgtcttgg ctatcatttc ttccaaaaac cccgacgttt cacatcttaa aaatgccctc      180
cacaagctcc aaatctccca tcccattctt aggtctcgcc tccattacag tcctactgcc      240
aacagttact ccttcgttac ctcccctcc cctttcattc aaatcaagta ctttaaccat      300
tctacaactt gtcaaatcct tgaaaacaac caaaacatct caccccttca tttgattctc      360
gaacacgagc ttaaccaaaa cgcttgggtt agttcttcat gtaccaccaa acacgacgtg      420 ttttttcgcca gtgtttatgc cttgcctggt gcaacaaggt gggtgttggt gctccgccta      480
catgcggctg cttgtgaccg gaccacggcg gtgtcgttgc tgagagagtt gttgacgtta      540
atggctattg aggaggagga acagggtttt cagcaaggtc aaaaagaaat tacgatgaac      600
aaaggagaga tcagtttggc catggaagat attcttccaa aaggcattgt taagaaaaca      660
ctttgggcac gaggagtgga catgctaagc tactctgtta attctttaag gttcacgaac      720
ttgaggttca agatgccaa atctcctaga tctactcaag tagtgaggtt gcttatcaac      780
cctgatgaca ctcagaagat cttgactggt tgcaaggcaa gagggattaa gttatgtgga      840
gcattaggag ctgccgggct gatttctgca cacagttcta aaagccgttc agatcatcaa      900
aagaagaaat atggcgttgt aacactcaca gattgccgct caattcttga acctccgctc      960
tccaatcacc atttcggttt ttaccactca gctattctga acacgcacgc catcaaagga     1020
ggagagaagc tttgggagct agcagagaaa gtgtacaccg tatttacaca ctacaagagc     1080
tgcaacaagc acttgtcaga catggcagac ctgaatttct taatgtgcag ggccatggag     1140
aaccctggct tgactccatc tgcctcattg aggacatgtt tgatatcggt cttcgaggat     1200
acggtgatag atgagtctag taaccagcaa aatcaagtcg gcgtagagga ctatatggga     1260
tgcgcttccg ctcatggcat cgcgccgtcc atcgcgatat tcgacaccat acgagatggg     1320
cgactggatt gcatttgcgt ttatccttcg ccgttgcatt caagggaaca aatgcaggag     1380
ctggttgata atatgaagtg catacttgtg gatgcaggga agaatgttgc tgatgaaact     1440
gagagttaag gagccagtct ggtctttgtc tgttgagctc                           1480
```

<210> SEQ ID NO 8
<211> LENGTH: 720
<212> TYPE: DNA
<213> ORGANISM: Gossypium hirsutum

<400> SEQUENCE: 8

| | | |
|---|---|---|
| acccccgggc aagtgatcaa agagaatggg aagaggaaaa atagagataa agaggatcga | 60 |
| aaacacaaca aatcgtcagg ttaccttttg caaacgcagg aatggcctgc tgaagaaagc | 120 |
| ttacgaactg tcagtcctct gtgatgctga agttgctctc attgtcttct ccagtcgagg | 180 |
| ccgtctgtat gagtactcca acaacaacat aagatcaaca atagacaggt acaagaaggc | 240 |
| ttgctcagat acttctaaca caaacactgt tactgaaatc aatgctcagt attatcaaca | 300 |
| agaatcagcc aagttgagac agcagattca aatgttacag aattctaaca ggcacctaat | 360 |
| gggagattcc ttgagttcct taactgtgaa agagttaaag caggtagaaa acaggcttga | 420 |
| aagaggaatt actaggatca ggtccaagaa gcacgaaatg ctactagctg aaatagagtt | 480 |
| tttgcagaaa agggaaatcg aattggaaaa tgaaagtgtt tgtctccgaa ccaagattgc | 540 |
| agaaattgag aggcttcagc aggcaaacat ggtgactgga cctgagctta atgctattca | 600 |
| agctttagct tctcgcaatt tctttagccc caatgtcatt gagcatccat ctgcttactc | 660 |
| ccatctctct gacaagaaga ttctccatct tgggtagagg agttggagaa agagctcatg | 720 |

<210> SEQ ID NO 9
<211> LENGTH: 973
<212> TYPE: DNA
<213> ORGANISM: Gossypium hirsutum

<400> SEQUENCE: 9

| | | |
|---|---|---|
| cccgggtccc tattgcatgc ctttcaattt gatttcatgg atgtaacaag cacaccaaat | 60 |
| agaaagaaa tggatcggat caaaggtcca tggagccccg aagaagatga cttgctccag | 120 |
| cagctggtac agaaacatgg ccccagaaac tggtctttga tcagcaaatc aatccccggc | 180 |
| cgatccgta atcctgtcg gctccgatgg tgcaatcaac tgtcaccgca agttgagcac | 240 |
| cgtgccttca ccccggaaga agacgagacc atcatccgag cacatgccag gttcggtaac | 300 |
| aagtgggcca ccatagcccg actcctcaac ggccgtaccg acaacgccat taaaaaccac | 360 |
| tggaactcca cgctaaaacg taagtgcttg ccggttgggg aagagtgtaa tttcgttgct | 420 |
| aatggagggt atgatggtaa tctgggagga gaggaacggc aaccgttgaa agatcggtg | 480 |
| agtgctggtc tatacatgag tccagggagc ccatcgggat cggatgtgag cgattctagt | 540 |
| gttcccgtct tatcatcttc ttacgtgtac aagccgatcc caaggaccgg cggtgttaac | 600 |
| gttgatgtaa atgttacgcc agctggagtg gaagcggcat catcttccaa cgatccaccg | 660 |
| acctcactga gtctgtcttt accggggtg gagtcatgtg aggtggtgtc aacccagcca | 720 |
| ataacggagt caactcagaa tcggagtgaa gaaagggag gtgggtgat gggtttcagt | 780 |
| gcggagttta tggcggtgat gcaagagatg ataaggttg aggtgaggaa ttacatgacg | 840 |
| cagatgcagc aacagcagca gcagcaaaac ggcgcagttc cgggaggagc gggaatgggg | 900 |
| atgtgtttgg atgggggtt caggaatctt atggctgtga acccagtcgg gatgagtaag | 960 |
| atcgagtgag ctc | 973 |

<210> SEQ ID NO 10
<211> LENGTH: 1861
<212> TYPE: DNA

<213> ORGANISM: Gossypium hirsutum

<400> SEQUENCE: 10

| | | | | | |
|---|---|---|---|---|---|
| cccggggata | gagagatggg | aggtccaccg | tacgattgct | tggcgaatcc | cctaggagcc | 60 |
| gtccgattaa | cattcgagaa | ggcaatatgg | tcagaatcgg | agactcctcc | gatccatccc | 120 |
| tccgccttta | acggcaaaga | ttggggtgcc | cttgaactct | tccgccactt | cctcttccaa | 180 |
| ggatcagggc | tttcccaggt | tcccatcctt | aatcccaaaa | cattaagatg | ggttcaaccc | 240 |
| aacagtcttg | tacgttaccg | tggtatgatc | caagacatgt | tgggaaatga | attctatgcc | 300 |
| ggcgcttaca | aggatggaaa | tttatggcgg | accaacaaat | tcatgatgt | ttctcaatac | 360 |
| ccaatgggtt | cctctcctga | tatgtgtatt | tgggaacgcc | gcttgctcta | ctgtgttcct | 420 |
| gtcccaggac | agaattcatg | gactgaacct | tctagtgaaa | tggaacctaa | ttggtcatct | 480 |
| caaaccaggg | agaagcggcg | taggatggat | gacgaagata | atgatcccat | ggatttggtt | 540 |
| cctgatgatg | agattaaaag | ctctccaatt | accaagaaga | tgagagaaga | tggacttcct | 600 |
| tccccttcac | aatccaggga | tactaaaact | acaagctctt | cttctatcac | aagtacattt | 660 |
| caatctgttg | acgaagataa | ccttccttgc | ctagtcaaga | tatatgattc | tccagaatca | 720 |
| gaattgaagc | tgaatgatgt | ttttgaattt | attggggtcc | tcacttttga | ttcagagctt | 780 |
| gcagttgaga | aagatgacaa | tgatgagtta | tcaaatagtt | tctatgatga | tgccctggtc | 840 |
| catttgcccc | ctaataaggt | ccctcgcttg | cactgtctta | tacataggaa | gcttgcagtg | 900 |
| caggactttc | tgccaggttc | cccaataata | gagccaaagc | cacatttggt | gaaagagaca | 960 |
| agggaagctc | tgttcaggca | tcttacggct | gttcttggaa | atgatgaggt | agctgctcat | 1020 |
| ttcgtgttgt | tgcatcttct | gtccaaggtt | catgctcgag | tagatgatgt | tgcagtgggg | 1080 |
| aagctgtcac | tcaatctaac | aggtttaaac | aaagaaagtg | tatctgtgtt | tggtactcga | 1140 |
| cttagtgata | cattcaaaaa | cctcctacca | ttcacgaatt | gcatgcctct | cacactggaa | 1200 |
| tatctgaaca | ttgcctcgct | tgccccgcaa | aaggattatc | aagccaacag | attggttcct | 1260 |
| ggcgttcttc | agctacccga | gggctcacac | ttgatggtag | acgagacccg | actagaatca | 1320 |
| ggaagcctca | attctactgg | aattgagaat | acaaagttgc | tgaaaatctc | atcgagtttt | 1380 |
| caaaaagtgg | agtatgactt | tcaatactat | aaagtggaaa | tggcaacgga | tgtccagtta | 1440 |
| cttatcttct | cggaggggaa | atctaatatt | gttcctgctg | atgttattgt | accttttcaa | 1500 |
| ccttcttgtc | ttgaatccac | tgaaatgcca | gttgctgagg | cactagaagc | ttggagatgg | 1560 |
| tacttggcta | ctgttagatc | attaccacat | tccattggat | cagaaataca | gaaggtggta | 1620 |
| gaagatgatt | tggttgcagc | aagacaaatg | gatcggagct | tgggaagtcg | agattttagc | 1680 |
| agatggttga | cgatggctcg | gctcatatcg | tcaagtttcg | gagaaaccag | tttgtcaaag | 1740 |
| gaacattggg | aaatggccaa | agaaatggag | aggctaagga | gggagagact | gaaatagaat | 1800 |
| ccaaaagtcc | acaagatttt | gaagctttgg | tatttggtaa | atgattgttg | ccccagagct | 1860 |
| c | | | | | | 1861 |

<210> SEQ ID NO 11
<211> LENGTH: 917
<212> TYPE: DNA
<213> ORGANISM: Gossypium hirsutum

<400> SEQUENCE: 11

| | | | | | |
|---|---|---|---|---|---|
| aaacaacatt | tgtgtttcaa | aaaaaactaa | tccatatact | gcaaaatcct | tgtgcatctt | 60 |
| cttcaaagca | aacagcaaca | actccaacaa | atgtccatga | aaaaagaagg | tgaaattcta | 120 |

```
tacaaaaagg gattatgggc aatggaggaa gacaagttac tcattgatta tgtcaatgtc      180
catggaaaag gacaatggaa caaaatagcc aacagaacag gtttgaagag aagkgggaaa      240
agttgtcggc taaggtggat gaattacctg agtcctaacg ttaaaaaggg tgattttct       300 gaagaagaag aagacctcgt cattagactt cataagctct tggaaacagg tggtctttga     360
ttgcgaaacg agttccaggt cgaactgaca atcaagtcaa gaattactgg aatagtcatt      420
tgaggaagaa actagggatc attgatcaaa acaagacaag gatcgatttt tgtcaaagtt     480
caaagcaagt caaagtgtgt catgttgatg aggcagccac ggatccaagt cctggacatg     540
gaacaaccac tgaaaccacg ggtataacag tggatcagag taaccagcas gaagtcattg     600
atcatcgggt cttaaacaat actactcaag aatcaatgac cactgagark tatatcaaca    660 cttttctggat tcctgaccat gattatgagc taagtacact tgccatgatt gaccacttcc   720
atgaatgktc tyyttttcay cttarctaga gactatgtta ttarattcgg gttttatttt    780
tagatataag tattcatcta acatggcaat gttaaatttt tcaaaagatt tttcatgtat    840
ttgagcagtt catgtgtttg aagattaaga tatatctgaa acaaatgcca caatcaaaat    900
aaccattatc gaattta                                                    917

<210> SEQ ID NO 12
<211> LENGTH: 2024
<212> TYPE: DNA
<213> ORGANISM: Gossypium hirsutum

<400> SEQUENCE: 12
cccgggcatc tgatctaatt gttggtggac acacacacac acacacacac acacacatac     60
atgtagcttt tagctttgaa atgtctactg gagttcaaca tcaagagaga gtaccaatga    120
acctgaagaa acaacttgct cttgctgtga ggaacattca atggagttat gcaattttct    180
ggtccatatc aactagacaa ccaggggtgt tagaatgggg agaaggttat tacaatggag    240
atataaagac aaggaaaaca gttcaatctg tagaactcaa cactgaccaa ttgagtttac    300
agagaagtga gcaactgaga cagctttatg agtctctttc agctggtgaa agcagtcctc    360
aagctaaacg accttcagca gcattatctc ctgaagatct tactgatact gaatggtatt    420
acttggtttg tatgtcattt gtattcaaca ttggccaagg attacctgga gaacattgt     480 ctactggtca acctgtttgg ctttgtaatg ctcattgtgc tgacagtaaa gtgtttggtc    540
gttcactact agctaagagt gcatcgattc agactgcagt atgctttccg ttttcaggag    600
gtgtggttga gctcggtgtg actgatttgg tatttgaaga tttgagcctc attcagcgcg    660
ttaaaacttt gctcttggat gatccacagc cgattgtttc taagagatcg attcaagtcg    720
atgggatgaa caacgatctt gcttgtccag ctcttgatcc tttgatcctt gccaccaaat    780
tgagtccaat attaggctgt gaacaactag aaacggtttc tcctgatgat agtccggacg    840
gcttggagcc taagcaatca agagaagatt cattattgat tgaagggata aatggtggag    900
cttctcaagt acaagttgg caattcatgg atgaagagt ttgcaattgt gttcaccatt      960
ccttgaattc aagtgactgc atatctcaaa ccattgcgga tcatcgaaag gtcgttcctc   1020
tttaccgggg agaaaatgat aatggtttgc aagatgttga agagtgcaat cagactaaac   1080
taacatcttt tgatcgccaa aacgatgatc ggcacttcca tgaagttctc tcggccttat   1140
tcaagagctc acacccgttg attttaggac cacagtttcg aaactctaac aaggaatcga   1200
gctttatcag atgcagaaa aatggcttgg tgaagcctca aaaagaaaga gatgaaaccc    1260
```

```
ctcaaaagtt actgaagaag atattgttct tggttcctca tatgcatgat agaggattga    1320
ttgaatctcc tgaaactaat gctgttcgag atgcagcttg gagacccgaa gctgatgaaa    1380
tttgcggaaa ccatgtgtta tcggagagga agcggaggga aaaataaaac gaacgactta    1440
tgatgttgaa atcacttgtc cctgcaaata caaggctgca caaggtttct atactagatg    1500
tcacgataga atacttacaa accctcgaaa gaagggttgc ggaattggaa tcttgcagaa    1560
agtcagaagc aagaacgaaa atcgagcgaa catcagataa ctacggcaat aataaaacca    1620
acaacggaaa gaaatcgtcc ctaagtaaaa ggaaagccta tgatgttgtt gatgaagctg    1680
atcaagagat cggctatgtt gcatctaaag acggttcaac agataaagtt actctcagta    1740
tgaacaacaa ggagcttcta atcgagttca agtgtccatg gcgagaagga attttgcttg    1800
aggtaatgga tgcattaagc attctcaatt tggattgcca ctcagttcag tcatctacca    1860
ctgaggggat tctctccctg accataaaat ccaagtacaa aggatcaagt gttgcaaaag    1920
caggaccaat cgagcaagca ttgcaaagaa ttgctagcaa gtgttgaagc tatttgttct    1980
agattttacc agtttctttt gtaagatccc atgtcataag gtgc                    2024

<210> SEQ ID NO 13
<211> LENGTH: 810
<212> TYPE: DNA
<213> ORGANISM: Gossypium hirsutum

<400> SEQUENCE: 13
cccggggcta gctcttactc aaatggcaac caaaacgatg atgttgcaaa tatttccact      60
tttcttcttt ttgttcagtg tctgcaactc cattttcctt ggtgctaatg gagatgacaa     120
tggtggttgg caaactgccc atgccaccct ctacggtggt gctgatgcta ccggcacaat     180
ggggggagct tgtggttatg gaaacctgta cagtcaaggg tatggaacga gcacagcagc     240
tttgagcact gcacttttca caatggcttg gagctgcgcgt gcctgctacg agctccggtg     300
caacaatgat cctcaatggt gcattagtcg aaccataacc gtgacagcca ccaacttttg     360
tccacctaac tatgctttat ctagtgacaa tggcgggtgg tgcaatcccc cacgagaaca     420
ctttgatttg gccgaaccgg cattcttgcg gatagcagaa tatcgagctg gaatcgtccc     480
tgttatgttc agaagggtgt catgtgtgaa gaaggaggc atcaggtaca ccatgaatgg     540
acattcgtac ttcaacatgg tgttgataac gaacgtggga gggggcagggg atataacgtc     600 agtgtccatc aagggttcca gaacaggatg gctacctatg tccagaaatt ggggccaaaa     660
ctggcagagc aatgcttacc ttaacggaca aagcctctct tttaaagtga ctgccagcga     720
tggcaggact atcacagcct acaatgtagt gcctgctggt tggcaattcg gacaaacttt     780
tgaaggaggc cagttttaag acaagatatc                                      810

<210> SEQ ID NO 14
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 14
acctcccatg acccagcatt g                                                21

<210> SEQ ID NO 15
<211> LENGTH: 22
<212> TYPE: DNA
<213> ORGANISM: Artificial sequence
```

```
<220> FEATURE:
<223> OTHER INFORMATION: Single strand DNA oligonucleotide

<400> SEQUENCE: 15
ccagcaacca ttgatatcgt ac                                              22

<210> SEQ ID NO 16
<211> LENGTH: 398
<212> TYPE: DNA
<213> ORGANISM: Gossypium hirsutum

<400> SEQUENCE: 16
cccgggtaca aacatggcta gttccggtgt ccttaagttg gtttccatga ttctcatggt      60
gtgcatgacg atgatgagtg cacccaaggc agccaaagcc gccatcacgt gcagcgacgt     120
ggtgaaccac ttgatcccgt gcttgtccta cgtacaaaac ggcggtacac ccgctgctgc     180
atgctgcagt ggggtaaaag cactctacgg cgaggttcag acctcccggg accgccaaaa     240
cgtgtgcaag tgcatcaaat cggcggtgaa cggaattccg tacaccagca ataacctcaa     300
tctcgcagcc ggcctacctg ctaaatgtgg tctccaactc ccttacagca tcagcccctc     360
cactgactgc aacaaggtgc agtgaggttg atgagctc                             398

<210> SEQ ID NO 17
<211> LENGTH: 1223
<212> TYPE: DNA
<213> ORGANISM: Gossypium hirsutum
<220> FEATURE:
<221> NAME/KEY: misc_feature
<222> LOCATION: (1015)..(1015)
<223> OTHER INFORMATION: n is a, c, g, or t
<220> FEATURE:
<221> NAME/KEY: misc_feature
<222> LOCATION: (1098)..(1098)
<223> OTHER INFORMATION: n is a, c, g, or t
<220> FEATURE:
<221> NAME/KEY: misc_feature
<222> LOCATION: (1158)..(1158)
<223> OTHER INFORMATION: n is a, c, g, or t

<400> SEQUENCE: 17
agctgaacac cccaaagatg gccaaccaca ccrytacctt tctccctaaa ctatccattg       60
aagctatkca gacagtgact ccgatgagga taactgaacc acgacagaca cgacaagtat     120
tggcagggga gcttgtagga cctgggattt ccaaaggtg tttgaacgtg gtccagtatt      180
acatgaagga gaaagaagaa gactctggtt ggttattggc tggtggatc aaggaaacac     240 ttgggagagc tttacatgag caaccaatga tttctggtcg tcttcggaaa ggggaacgaa     300
acgatggaga attggagatt gtttccaatg attgcggcat tagactcatt gaggcaagga     360
ttcagatgaa tttgtcggat tttcttgatt tgaaacaaag ggaagatgct gaagctcagc     420
ttgttttctg gaaagatatt gatgaacaaa cccacagtt ctcccccctc ttttatgttc      480
aggttactaa tttccagtgt ggtggatatt caattgggat tagctgcagt attcttctag     540
cagatctttt gttaatgaaa gagttcctta agacatgggc agatattcac aacaaggtta     600
ttatcaacaa aaacgatgaa caaaagcttc ctttattcta ccttcctggt ctgaaaaaca     660
ccaatggtgc ctcccttaac atcatcacct caaattcaag caaaaactca gccaaaacca     720
tgattttcca gatccatgct gaaactgaaa gtccaggag tgactggtgc aggaaaatgg     780
cattagcctg tctggaggaa gccgagagca acctargaag tgttgtgggt ggagaatttt     840
ccttgtttgt gaacgaatcg tttgagtcca tcaaagttga aagctgctca aagcaaggga     900
```

| | |
|---|---|
| tgtcvaaaga agcagagatg ggagtcttga atcgtgcaaa atgggatgat ttgggggcta | 960 |
| atgaagttag ttttggagat gggaataaac ctgcgcatgt ttcgtattgg cttanatcga | 1020 |
| cgttgggtgg gcytgkcatt kgtattsctt sgcctsagga ggaaaatgca ctgtgaatat | 1080 |
| cattggcaca gttcctgnca atgggagggg gcattgaact atcagctggg atggaaatgc | 1140 |
| tatagaaaga aagagganat gctgatgatg ggtgcctttg ttgggccttg aatctttgga | 1200 |
| cgttggcaag ctagaggtgc ttt | 1223 |

<210> SEQ ID NO 18
<211> LENGTH: 1768
<212> TYPE: DNA
<213> ORGANISM: Gossypium hirsutum

<400> SEQUENCE: 18

| | |
|---|---|
| ttatagtacc ggatactgcg cacgacacaa gccgaattca gcacgatcgt tgaaaaaata | 60 |
| tgggtttcca aagaaacata ttgggtttcc ttttattgat attggcttca ctaacaagcc | 120 |
| tctcttctag ccttcctagt gaatactcca tagtggaaca tgagattgac gcatttcttt | 180 |
| cggaggaaag ggtgttggag atcttccaac agtggaaaga aaagaatcag aaagtgtacc | 240 |
| ggcaagccga ggaggctgag aaaaggtttg aaaatttcaa ggggaatttg aagtatatcc | 300 |
| tagagaggaa tgcaaagaga aaagcaaaca atgggaaca ccatgtggga ttgaacaagt | 360 |
| ttgctgatat gagcaatgag gagttcagaa aagcttactt gtcaaaggtg aaaaagccca | 420 |
| tcaacaaagg gataaccctg tcaaggaaca tgaggagaaa ggtgcagtct tgtgatgcac | 480 |
| cctcctcctt gaattggagg aactatggag ttgtgactgc tgtcaaggac caaggttctt | 540 |
| gtggaagttg tgggcattc tcatcaaccg gagccatgga aggaatcaat gccttagtta | 600 |
| ctggagacct aattagcctt tcagaacaag aacttgtaga ttgtgatacc agcaactatg | 660 |
| ggtgtgaagg aggatacatg gactatgctt tcgagtgggt tataaacaat ggcgggatcg | 720 |
| atagcgaaac cgactacccc tacactggtg tggatggcac atgtaacacc accaaggagg | 780 |
| aaaccaaggt tgtatctatt gatggctatc aagatgtaga gcaatcagat agtgctcttt | 840 |
| tatgtgccgt tgctcagcaa cctgttagtg tgggaattga tggttccgcc attgattttc | 900 |
| aactttacac tggtggaatt tatgatggga gctgctcgga tgatccagat gacattgatc | 960 |
| atgctgtttt aatagttggt tatggttcag aaggcagtga agagtattgg atagtgaaga | 1020 |
| attcatgggg aacaagttgg gggatagatg gatatttcta tctaaaaaga gacactgatt | 1080 |
| taccatatgg tgtttgtgct gtcaatgcca tggcttctta tccaactaaa gaatcctctt | 1140 |
| caccatcccc ttatccatcg ccaagtgttc ctccaccgcc acctccttca actccaccac | 1200 |
| caccaccacc tccatctcct tcaccaagtg attgtggaga cttttcctat tgttcaagtg | 1260 |
| atgagacatg ctgttgcctt tttgaattct atgattattg cctaatatac ggctgctgtg | 1320 |
| aatatgaaaa tgctgtttgc tgtaccggaa ctgaatactg ctgccctagt gattacccca | 1380 |
| tttgtgatgt ccaagaagga ctctgcctca agaacgctgg agactatctg ggagtagcag | 1440 |
| ctaggaagcg aaaggtggct aaacacaaat taccatggac taaaatagag gaaacagaga | 1500 |
| taacatatca gcctctgcaa tggaaaagga accccttgc tgcaatgcgt tgaaaaaagt | 1560 |
| gaaaaattac atatcatctc ttaaaccttg aaggttgttt tcacctttt tcttttttctt | 1620 |
| tcatttttgc ttttttcattt ccagcaagca aatccatgca gataagacta agaaagggc | 1680 |
| atatttgttt agatgatgca tttgaatttg gaaactgtgt ttgtcattct tcaccagtgg | 1740 |
| ggtataaaaa ctactatgct tttgttta | 1768 |

<210> SEQ ID NO 19
<211> LENGTH: 1027
<212> TYPE: DNA
<213> ORGANISM: Gossypium hirsutum

<400> SEQUENCE: 19

```
tctagatgaa ggttctctcc ccaattcttg cttgcctagc gcttgctgtg gtggtaagcc      60
atgctgctct ctcacctgag caatattgga gctataagct gccaaatact ccaatgccaa     120
aggctgtcaa agaaattcta catccagaac tgatggagga aaaagcacc tctgtaaatg      180
taggaggtgg tggtgtaaac gtcaatacag gaaaagggaa gcctggggt gacacccatg      240
tgaacgttgg aggcaaagga gttggagtga acacggaaaa gccaggggt ggcactcatg      300
tgaatgttgg agacccttt aattacctat atgcagccag tgaaactcaa atccatgaag      360
acccgaatgt ggctcttttc tttctggaaa aggatatgca cccgggggca caatgagcc      420
tgcatttcac tgaaaataca gagaaatcag ctttcttacc ttatcaaact gcccaaaaaa      480
taccgtttc atctgacaag ttgccagaaa tttcaacaa gttttcagtg aaacctggat       540
cagtgaaggc agagatgatg aagaacacaa ttaaggagtg cgaacagcca gcgattgaag      600
gagaggaaaa atattgtgca acctcactgg agtcaatgat tgactatagc atttccaaac      660
tagggaaagt tgatcaggca gtctcaacag aagtggaaaa acaaacccca atgcaaaagt      720
atacaatagc agctggagtg cagaagatga cagatgacaa agctgtagtg tgccacaagc      780
agaattatgc atatgctgtc ttctattgcc ataaatcaga acaacaagg gcttacatgg      840
ttcctttaga gggtgctgac ggaacaaaag ccaaagcagt agcagtctgc cacacagata      900
catcagcatg gaaccctaag catttggctt ttcaagtcct aaaagttgaa ccaggaacca      960
ttcctgtctg ccatttcctt cctcgggatc acattgtttg ggtccctaag taaaatcct      1020
ggagctc                                                              1027
```

<210> SEQ ID NO 20
<211> LENGTH: 942
<212> TYPE: DNA
<213> ORGANISM: Gossypium hirsutum

<400> SEQUENCE: 20

```
cccgggcata cagagatgga gaggcaaaga agcaagcagg tttgtttgtt gatgtgggtt       60
ttggttgctg cctttttctc ccacaatagg gtcattgcag tgacctccac tggccttggt      120
gagcagaaaa actactatcc agctcctgac cctcatgctg gaactccccc ttcaggttca      180
catggcacac caccatcttc aggaggtgga tcacctccct ctcatggaac cccgtcacat      240
ggaggtggtt accacccttc accaacacca tcaacgcctt cgggtggaaa ttgtggaact      300
ccccacatg acccttcaac tccatcaaca ccatcacaca ctcctcctca tggtactcca      360
ccatcatctg gaggtggtag tccccatcg tatggaggag gcagtccccc atcgtatgga       420
ggaggcagtc cccatcgta tggaggaggc agtccccat catacggagg tggcagtccc       480
ccatcatatg gaggtggcag tccaccaact actcccattg atccaggaac tccaagcatt      540
ccctcacctc cattctttcc tgctccaact ccaccaattg gtggtacatg cgatttctgg      600
aggagtcacc ccacactgat atgggtctg cttggttggt ggggcactgt aggcaacgca      660
tttggcgtga ccaacgctcc tggacttgga acaagcatga gcttgcccca agcactttca      720
aacacacgta ctgatggact tggggcgctt taccgggaag gaacagcctc atttctcaac      780
```

| | |
|---|---|
| tccatggtga ataataggtt cccattctcg actaagcaag tcagggagac ttttgttgca | 840 |
| gcacttggtt caaacagcgc tgcagcagct caggctcgtc tcttcaagct tgccaatgaa | 900 |
| ggccacctca agccaaggac ctaagcaaac acctttgagc tc | 942 |

<210> SEQ ID NO 21
<211> LENGTH: 627
<212> TYPE: DNA
<213> ORGANISM: Gossypium hirsutum

<400> SEQUENCE: 21

| | |
|---|---|
| cccgggagaa agatgatgaa aaggggtttt attgttttgg ccttgacggt ggttttcgcc | 60 |
| gcgacggtgg ttacggcggc tgacgagagt gggttagcga atgagtgcag caaagatttc | 120 |
| cagagcgtga tgacttgctt aagctttgct caaggaaaag cagcgtcgcc gtcgaaggag | 180 |
| tgttgtaatt cagtggcggg gattaaagag aataaaccca aatgtttgtg ttatatttg | 240 |
| caacaaacac aaacttccgg tgctcaaaat ctcaaaagct taggtgttca agaagataag | 300 |
| ctgtttcagt taccgtcggc ttgtcaattg aagaacgcta gcgtcagtga ttgcccaaag | 360 |
| cttcttgggt tatctccgag ctcaccagac gccgccatct tcaccaactc ctcctctaaa | 420 |
| gcaacgacac ccagtacttc aacaaccacc gcaacgccgt cttccgcggc cgataaaacc | 480 |
| gatagcaaat ccagtggaat caagcttggt ccccacttcg tcggttccac ggcggcgcta | 540 |
| ctggttgcta cagcggccgt gttttcctt gtattcccag ctggatttgc ttcaatagtt | 600 |
| tagggttttt gcatgggatt tgatatc | 627 |

<210> SEQ ID NO 22
<211> LENGTH: 2012
<212> TYPE: DNA
<213> ORGANISM: Gossypium hirsutum

<400> SEQUENCE: 22

| | |
|---|---|
| cccgggcggc aacttaaaag aaaaccttt ctttcctcat tgttttacta ctaaaatccc | 60 |
| ataatgccgg tcgtggattt tgtctgtgtt ttttagttt cagttgtgat gtttaatttg | 120 |
| agagtaagca cagaaccagt tgaagacaag caagctctac ttgctttcat ttcgggaatt | 180 |
| agacatgccg accgggttaa atggaattca tcgacctcag cctgtgattg gttcggtgtt | 240 |
| caatgcgacg ccaaccggtc tttcgtctac actttacggc tccccggtgc ggcccttatc | 300 |
| ggttcgattc cgcccaatac aatcggtcgg ttgaaccgac ttcgagtttt aagtctacga | 360 |
| gcaaaccgtt tgtccggtga gatccctgcc gatttctaca atttgactca gctgcgtagc | 420 |
| ctttatttgc aaggtaacga gttcaccggt ccgttcccac ctagtgtgac tcgtttaact | 480 |
| cgtttgactc gccttgatct ttcttctaat aatttcaccg gtccaattcc tttgggtgtc | 540 |
| aacaatttga ctcagttgac cagactcttc ttgcaaaata caagttttc cggttctctc | 600 |
| ccgagcatcg actcggacgg tttaaacgat ttcaatgtgt ctaacaacaa ccttaaaggt | 660 |
| tcaatccccg actcgttatc taaattcccc gaatcttcat tcgccggaaa cattgggctt | 720 |
| tgcggcggtc cacttcggcc atgtaaccca tttcctccat ctccatctcc gactgagccc | 780 |
| attccgccca aaacttccgg tcaaagctcg aaaagccttc ccaccggcgc catcattgcc | 840 |
| attgccgtgg ggtcagcaat tgttgcgtta ctgttattac tattcctcat tatctgcttc | 900 |
| cgtaaatgga aacggaagtc accgaggcgg cagaaggcga taccatcgac gacacatgca | 960 |
| gttccggtgg aggaggcggg gacttcctcg tcgaaagatg atataaccgg aggctcaacg | 1020 |
| gaaatcgaaa ggatgatgaa taataagctc atgttcttca aaggtggcgt ttacagtttc | 1080 |

```
gatttggagg atttgatgag ggcgtcggct gaaatgttgg gaaaaggcag caccggaacg    1140
tcgtacaggg tggttttagc ggtggggacg acggtggcag ttaaacggtt gaaagacgtg    1200
gcggttagta aacgagagtt cgtaatgaag atgggaatgt tgggtaaaat catgcatgaa    1260
aacgtggttc cgttgagagc tttttattat tccgacgagg agaaattgct ggtttatgat    1320
tacatgcatg gtggaagctt gtttgcgctg cttcacggta gcagaagctc ggctcgtaca    1380
ccgttagaat gggaccccg  gatgaaaata gccctaggcg tggctagagg cctcgcgcac    1440
ctccacagtt cacaaaacat ggtccacggc aacattaaat cttccaacat ccttctccga    1500
ccagaccacg aagcctgcat ctcagagttc ggtcttaact ctcttttcaa caccaacact    1560
ccacctagtc gcatcgcggg ttaccaagca cctgaagtaa ttcaaaccca taaagttacg    1620
gtgaagtcag acgtttatag tttcggggtg ttattattgg aattattaac cggtagggca    1680
ccaatccaac catcaataac tgaagaagcg ttcgatcttc cgcgttgggt ccaatccgtg    1740
gttcgggagg aatgggcggc cgaggtgttt gacgcagagt taatggcata ccacgacatc    1800
gaggaagaaa tggtgcaagc gttacaaatt gcaatggttt gtgtctcgac agtgcccgat    1860
caaagacccg tcatgtcgga agtggtacgt atgatcggag atatgataga tagagggga    1920 acaaatgacg gtacggcagc cgccatatga tccgttaaac aatgaaacaa aattcaaagt    1980
gtgttgacct tgagaagcca acaaaggagc tc                                  2012
```

<210> SEQ ID NO 23
<211> LENGTH: 2013
<212> TYPE: DNA
<213> ORGANISM: Gossypium hirsutum

<400> SEQUENCE: 23

```
tactccaagc aagtattttc cttacacgtt tgttttctt  gtgattaatc gatatggcta     60
gctcaatgtc ccttaaactt gcatgtgtgg tggtgttgtg catggtagtg ggtgcacccc    120
tggctcaagg ggccgtaacc tgtggtcaag tcacctcgtg ccgaattcgg cacgagcttt    180
ataaaagagt wcccaaagct gacaagcagc cataatatca tctgctaaac atatggcaga    240
aatgtcaacc ctttgtacat ttcttttctc acttctactc tttgcctcac atcccttat     300 cctcccccact gctgccgacg gccggtggca gctgctacaa aaaagcattg gcatctcatc    360
catgcacatg caactcctta aaaatgaccg tgttgttatg tatgatagga ctgatttcgg    420 cccatcccact ctgccattgg caagtgggaa atgccacaat gacccaacca acaccgctgt    480
ccaagtagat tgtacggcgc attcagttga gtatgatgtt ttgagcaaca agttcagggc    540
tcttactgtc caaagcaacg tttggtgttc ttcaggcggc gtcatgcctg acggtaaatt    600
ggtccaaacc ggtggtttca gcgaaggaga acttcgggtc agggttttca gcccatgcga    660
aagctgcgac tggcacgaaa caccaaatgg attggcggcc aaaagatggt atgctaccaa    720
tcatgtcttg ccagatggaa gacaaattgt tgtcggcggc cgagaacaat ttaattacga    780
gtttgttcct aaaaacatag ccgccgacac gttcaagttg catttcctgt cggaaaccaa    840
tgaacgagga gtagagaaca atctctaccc ttttgttttt ctcaatgtcg atggaaacct    900
gttcattttc gccaacaatc gagctatttt gcttgattat gtgaacaaca aggtggtgaa    960
aacttacccc aaaataccag gtggggagcc aagaagctat ccaagcacag gttcggctgt    1020
attgctacca ttgaagaact tgacagccgc cactattcaa gctgaagttt tagtttgtgg    1080
gggtgctcca aaaggatcat tgtccaagc  attacaaggt aagttcgtta aagccttgaa    1140
```

-continued

```
cacttgcgcc aggatctcaa taaccgaccc gaaaccaaaa tgggtcttgg aaactatgcc   1200
tttagctaga gtcatgggtg acatggtatt gcttccaaac ggcaaagttt tggtcatcaa   1260
cggagcacgt tccgggtcag caggatggga cttaggaagg gacccggtct taaatccagt   1320
gttatacatg cctgataatg aaatcgagtc acgattcaag atactaaacc aacaaagat    1380
ccctcggatg taccattcca cagcagtatt acttcgtgat ggaagagttt tagtgggtgg   1440
aagcaatcct catgcgtatt acaactttac gggagtcctt taccctactg aactaagcct   1500
ggaggcattc tatccgggtt atttggacgc caaattcaac aatttacgac ccaccattgt   1560
tgctcccaag tcaatgtccg gaatcagata caataagaaa ttaaaaatta agtggtgat    1620
tacaggtgaa gtaactctaa acttgttgtc ggtgacaatg gtgtcaccag ctttaatac    1680
ccattccttc tctatgaatc aaaggttgct tgtacttgga aacgacaaag ttatggcatc   1740
cgggaaatca acgtatgaga ttgaagtgat gacgccaggt tcgggtaacc tcgcacctgc   1800
aggcttttat cttttgtttg tggttcatca agacatcccc agccaaggca tttgggtcca   1860
tttgaaatag ttttgattg atatgtttgt gaaattttga tcattattta gagaaagaaa    1920
tgtttatttc aacaatgtgg taaaattgtc ccctacatta agcaaatgta tttacaaatt   1980
tgtatcaata aagaggata attgtttccg tcg                                2013
```

<210> SEQ ID NO 24
<211> LENGTH: 1566
<212> TYPE: DNA
<213> ORGANISM: Gossypium hirsutum

<400> SEQUENCE: 24

```
cccgggactg taaaaaagca taggttccca atgcagatcc tcccgtttcg aggaggcgca     60
cttgtgtgct tcattgcttc cttgttattt gttgccagtt tttgcaatgc cgatgctaaa    120
acagtcgagg ttgtcggggc tggtgagtgt gcagattgtg cagagaataa cttggagatt    180
agccaggctt tttcagggct acgagtaagc atagactgca agcccgaaaa tgggaagaac    240
tttaaaacac gaggatcagg ggagcttgat aaacaaggca attttaaagt attcgttcca    300
gaggatttgg ttgaaaatgg ggaactgaag gaagaatgct atgcacagct tcacagtgta    360
tcggcagcac cttgtcccgc ccatgatggc ttggagtcgg ccaagttagt gttgaagtcc    420
aggagtgatg ggaaacacgg gtttgggtta aaaggaaagc tcagattctc acctctaacc    480
tgtgcttctg cctttctttg gcctcacttt aagtttcctc ccttgcctaa gtggaaccat    540
cccccttgc ccaagtttcc acttccccca ttcaaaggct ccaccacca ttatccaata     600
atccctccca tctacaagaa acctcttccg ccaccgtccc cggtgtacaa gcccctcca    660
gttcccgtaa acccacctgt tccaatctat aaacctccac cagttccagt ctataaacct    720
cctccagttc cagtaaaacc acttcctcca cctgttccaa tctacaaacc tccaccagtt    780
gaaaaaccac atcctccacc tgttccagtc tataaacctc caccagttcc agtatacaag    840
aagccatgtc ctccaccagt tccagtctat aaatctcctc cggttccagt atacaagaaa    900
ccgcatcctc ctccagttcc agtctataag aaaccacatc cacctccagt tccagtatac    960
aagaaaccat gtcctccccc agttccagtc tataaatctc tccagttcc ggaaccacat   1020
cctccgccag ttcagtcta taagaaacca catccacctc cagttccagt atacaagaaa   1080
ccatgtcctc ccccagttcc agtctataaa tctcctccag ttccggaacc acatcctccg   1140
ccagttccag tccataagcc tcctccagtt ccggtataca agaaaagagt ccctcctccg   1200
gttccaatct acaagccccc tccagttcct gtatacaaca aaccactacc tccccggtt    1260
```

```
ccagtgtata cgaagccact tccaccacct gttccaacct acaaaccaaa acccctccct    1320
cccattcctt acaagccact ccctccactt cccaagatcc ctccattccc taagaagcca    1380
tgccctcccc ttcctaagct acctcctctt cccaagattc ctcccaagta tttccaccac    1440
caccctcccc ttcctaagct acctcctctc cctaagattc ctcccaagta tttccaccac    1500
catcccaagt tcggaaaatg gccttctttg ccacccttg  ctccccatca tccttaagct    1560
gagctc                                                               1566

<210> SEQ ID NO 25
<211> LENGTH: 689
<212> TYPE: DNA
<213> ORGANISM: Gossypium hirsutum

<400> SEQUENCE: 25
cccggggatg gtgagaggca aaattcagat gaagcgaatt gaaaatgcaa cgagccggca      60
agtcaccttc tctaagcgac gaaacgggtt gttgaagaag gcttatgaac tatatgttct     120
atgcgatgct gaagtagctg tcatcatatt ttctcataaa ggaaaactct acgagttctc     180
aagttccgac aacatgcaaa acaccataga acgataccgt cagtacaaga agatgtcca     240 gagtaacatc cctgaatttg acagatacac acagcaacta aggcttgaag cagaaaatat     300
ggccaagaag attgagttcc ttgaggtttc taaaaggaga atgttgggtc aaaatcttgg     360
ttcttgttct atagatgaac ttcaagaggt tgaaaaccag cttgaacgca gcttaagaaa     420
cattagggca agaaagggct atttattcaa ggagcagata ctgcaactaa agctaagga     480 aagatatatg caagaggaga atgccaagtt atctgctaag aacaatggta caacatgcag     540
ccagcagaac gcggaggtgg agacagaact gttcctcggg ttgcccgaaa accgctgttc     600
ctagcaggta ggtctttgga tatggaatga aaatgatatt ccctattgga ataatgcttg     660
cttgtacgtt atcgccattg ctagagctc                                      689

<210> SEQ ID NO 26
<211> LENGTH: 258
<212> TYPE: PRT
<213> ORGANISM: Gossypium hirsutum

<400> SEQUENCE: 26

Met Ala Thr Lys Thr Met Met Leu Gln Ile Phe Pro Leu Phe Phe Phe
1               5                   10                  15

Leu Phe Ser Val Cys Asn Ser Ile Phe Leu Gly Ala Asn Gly Asp Asp
                20                  25                  30

Asn Gly Gly Trp Gln Thr Ala His Ala Thr Phe Tyr Gly Gly Ala Asp
        35                  40                  45

Ala Thr Gly Thr Met Gly Gly Ala Cys Gly Tyr Gly Asn Leu Tyr Ser
    50                  55                  60

Gln Gly Tyr Gly Thr Ser Thr Ala Ala Leu Ser Thr Ala Leu Phe Asn
65                  70                  75                  80

Asn Gly Leu Ser Cys Gly Ala Cys Tyr Glu Leu Arg Cys Asn Asn Asp
                85                  90                  95

Pro Gln Trp Cys Ile Ser Arg Thr Ile Thr Val Thr Ala Thr Asn Phe
                100                 105                 110

Cys Pro Pro Asn Tyr Ala Leu Ser Ser Asp Asn Gly Gly Trp Cys Asn
            115                 120                 125

Pro Pro Arg Glu His Phe Asp Leu Ala Glu Pro Ala Phe Leu Arg Ile
        130                 135                 140
```

```
Ala Glu Tyr Arg Ala Gly Ile Val Pro Val Met Phe Arg Arg Val Ser
145                 150                 155                 160

Cys Val Lys Lys Gly Gly Ile Arg Tyr Thr Met Asn Gly His Ser Tyr
            165                 170                 175

Phe Asn Met Val Leu Ile Thr Asn Val Gly Gly Ala Gly Asp Ile Thr
        180                 185                 190

Ser Val Ser Ile Lys Gly Ser Arg Thr Gly Trp Leu Pro Met Ser Arg
    195                 200                 205

Asn Trp Gly Gln Asn Trp Gln Ser Asn Ala Tyr Leu Asn Gly Gln Ser
    210                 215                 220

Leu Ser Phe Lys Val Thr Ala Ser Asp Gly Arg Thr Ile Thr Ala Tyr
225                 230                 235                 240

Asn Val Val Pro Ala Gly Trp Gln Phe Gly Gln Thr Phe Glu Gly Gly
                245                 250                 255

Gln Phe
```

<210> SEQ ID NO 27
<211> LENGTH: 1432
<212> TYPE: DNA
<213> ORGANISM: Gossypium hirsutum

<400> SEQUENCE: 27

```
cccgggttcc atgaaaaggg tctcgaacat ctatatagag gcaaagaaac atctctctga    60
tctgctaaca aacgaggatc aaaatgagga tcttttgagt acacaggttc caaaaacctt   120
aggtaggatt ctttctcttc ctgagtataa tacatcccct gtcagcagcc ctggtcagaa   180
cttggagcat agttttacaa ctgcgcatat gagatttgca ggctcggaca aattgcaaat   240
ggtgagtgaa atgatcggt tgtcagcct tctaagtatg agggcagaga agaccgatgg   300
ccagctttgc atttctgaaa acaaaagcga taatgaagtt gaaagtgata atgcaatttc   360
aaacaacctt gacactagtg tgaataatga caaagaggat ccaatttttt gttctataaa   420
agatgaattg agttccaaag agtctgtgag tattgttaaa gctactgaaa tgatggttca   480
tgaagaaagc aagtccctgg atatttcttc agagacgagc ggctcttcaa ttatcacaga   540
tgataaaaat gttgacatat atgaagtttg tgatgaaaaa caaaatcctt ggtacttgaa   600
acaggattca tcggaagtgg accaacagcc tttttctcca ttatcatctc catcagactc   660
atcagtcatg aaaaaggttg aatgtttgga gagtgttact gatataccag agcgatcaag   720
ccccgtatct gttcttgagc caatatttgc agatgatctt atcagccctg caagcatcag   780
atcttattcc ggtgaaacat ccattcaacc gctaagaatt cgattcgaag aacatgactc   840
tttggccaca aatcagagca atcgaattaa aacttgtatg aatgataagg aatcaatatt   900
tgagcacata aaggcagtgc tgcaagcctc gagtttcagc tgggacgaag tctacatccg   960
gtcactttct tcagacctgc ttatcgaccc attgttggtt gacgaggtcg aatacttgcc  1020
caaccagctt tgtcaagacc aaaaactgct ctttgattgc attaatgaag tagtcagaga  1080
ggtttgtgag tactattttg ttccccctag tgttccattt gttaaaccca atatccgtcc  1140
tatcccaaac atgcaaaata caattcaaga agtctgggag ggagtttatt ggcatttgct  1200
cccgactcca ttgccttgta ctctggacct ggtagtccga aaagacctgg ctaagactgg  1260
aacatggatg gaccttcaac ttgacactgg ttatattggt gttgagattg gtgaagccat  1320
cttcgaagat ttagtggaag acaccataac aagctacata aatggaagtt gggaatgtga  1380
atataatgtg cttccagctt agcttagctg aaggacaacg acgatagagc tc          1432
```

<210> SEQ ID NO 28
<211> LENGTH: 1079
<212> TYPE: DNA
<213> ORGANISM: Gossypium hirsutum

<400> SEQUENCE: 28

```
ggattccggt gacggtgttt ctcacaccgt gccaatctat gaaggatatg cccttccaca      60
tgccatcctc cgtcttgacc ttgcaggtcg tgatctaacc gatgccttga tgaagattct     120
taccgagaga ggttacatgt tcaccaccac tgctgaacgg gaaattgtcc gtgacatgaa     180
ggagaagctt gcttatgttg ccctggacta tgagcaggaa ctggagactg ccaagagcag     240
ctcatctgtt gagaagaact atgagttgcc tgacggacaa gtcattacta ttggagctga     300
gagattccgt tgcccggaag tcctcttcca gccatctttc atcgggatgg aagctgctgg     360
aatccatgaa actacctaca actctatcat gaagtgcgat gtggatatca ggaaggatct     420
ctacggtaac attgtgctca gtggggggttc aaccatgttc cctggtattg cagaccgcat     480
gagcaaggag atcactgctc ttgctccaag cagcatgaag attaaggtcg ttgcgccacc     540
agagagaaag tacagtgtct ggattggagg atctatcttg gcatcactca gcaccttcca     600
gcagatgtgg atttccaagg gtgagtatga tgaatccggt ccatccattg tccacaggaa     660
gtgcttctaa gttttgtaat tgcttttgat ggtgatctac attttgcatt tagttggctt     720
tttttgtgtg cgatgttaag tgaagtccaa agtctggttt atgtggggag agttagggat     780
cattgtagga tggtgtactt gatattgacg tattattatt ttagccttt ccgtatcac      840
caccattaag atgatgggtc ctatggagat ggcggtgggc ggacaattgg tgcttaattc     900
cttccttata atccatcttt gaaccatgtt gcttaaaagg atgtttggag ctggagactg     960
gattgtggtg ctttttatt ttattttatt atttaatatt caagggtttt gagaacatta    1020
atgttcatag ctattattgt acgagatttt ttttgaaaaa ttagagtcag tttgcggtc    1079
```

<210> SEQ ID NO 29
<211> LENGTH: 657
<212> TYPE: DNA
<213> ORGANISM: Gossypium hirsutum

<400> SEQUENCE: 29

```
cggccgcgtc gacttttta ataaaactga acaaccctt cttcacacaa aaatatgctc       60
cgtacaattc gtttattctc tcatagcatc tcttctaaat taaaattgct aaagcttgga    120
tacacaaagc acaatcactc actcacttaa gccttagaca tgtgtcggat caagtcgata    180
acacgggaac tgtaaccca ttcgttgtca taccaagtca caagcttaac aaagttgtca    240
ttcaaagcaa ttccagcctt ggcatcaaaa atgcttgacc tgttgtctcc gatgaagtca    300
gttgagacta atcttcgtc cacataacca agaattccct tcaagttgcc ttcagattcc    360
gccttgatag cagccttaat ttcatcatat gtagccttct tctcaagtct cacagtgagg    420
tcaaccacag agacatcaac agtgggaaca cggaaagcca ttccagtcag cttgccattc    480
agtgctggca aaactttgcc gacggccttg gcagctccag tgctgctagg aatgatattg    540
aaggaagcag ctctaccacc tctccagtcc ttcatggaat gaccatcaac agtcttttgt    600
gtagcagtaa tagaatgaac agtggtcata agaccctcaa cgatgccaaa tttatca       657
```

<210> SEQ ID NO 30
<211> LENGTH: 649
<212> TYPE: DNA

<213> ORGANISM: Gossypium hirsutum
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (492)..(492)
<223> OTHER INFORMATION: n is a, c, g, or t
<220> FEATURE:
<221> NAME/KEY: misc_feature
<222> LOCATION: (504)..(504)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (630)..(630)
<223> OTHER INFORMATION: n is a, c, g, or t

<400> SEQUENCE: 30

| | | | | | |
|---|---|---|---|---|---|
| gagaaaagga | agacaacgat | ggtgtctctg | aagttacaga | agcggctcgc | cgctagcgtc | 60 |
| ctgaagtgtg | gccgtggcaa | ggtttggctt | gatcctaatg | aaatcaatga | aatctccatg | 120 |
| gccaactcca | ggcagaatgt | taggaaactt | gttaaggatg | gttttatcat | ccggaagcct | 180 |
| accaagattc | actcccgatc | tcgtgcacgc | agaatgaaag | aggccaagag | aaagggtcgt | 240 |
| cattctggct | atggtaagag | gaagggtacc | agggaggcaa | gattgcctac | aaagatcctt | 300 |
| tggatgagga | gaatgcgagt | actaaggcgt | ttgcttcgta | agtacaggga | atccaagaag | 360 |
| attgacaagc | acatgtacca | tgacatgtac | atgaaggtga | agggtaatgt | atttaaaaac | 420 |
| aancgtgtct | tgatggaaag | catccacaag | tccaaggctg | agaaggcaaa | aaaaaaaaca | 480 |
| ctctcaaatc | antttgaggc | caancgaact | aaaaacaagg | cgagcaggga | gagaaagatg | 540 |
| gccagaaagg | aaaaacgcct | tgcacaggga | cctggtgtga | agcagcacc | tgcagctgca | 600 |
| ccgcaacagg | ccgaaggagt | taaaaantcn | aagaaatgaa | tgaggtact | | 649 |

<210> SEQ ID NO 31
<211> LENGTH: 877
<212> TYPE: DNA
<213> ORGANISM: Cauliflower mosaic virus

<400> SEQUENCE: 31

| | | | | | |
|---|---|---|---|---|---|
| aagcttgcat | gcctgcaggt | ccccagatta | gccttttcaa | tttcagaaag | aatgctaacc | 60 |
| cacagatggt | tagagaggct | tacgcagcag | gtctcatcaa | gacgatctac | ccgagcaata | 120 |
| atctccagga | aatcaaatac | cttcccaaga | aggttaaaga | tgcagtcaaa | agattcagga | 180 |
| ctaactgcat | caagaacaca | gagaaagata | tatttctcaa | gatcagaagt | actattccag | 240 |
| tatggacgat | tcaaggcttg | cttcacaaac | caaggcaagt | aatagagatt | ggagtctcta | 300 |
| aaaaggtagt | tcccactgaa | tcaaaggcca | tggagtcaaa | gattcaaata | gaggacctaa | 360 |
| cagaactcgc | cgtaaagact | ggcgaacagt | tcatacagag | tctcttacga | ctcaatgaca | 420 |
| agaagaaaat | cttcgtcaac | atggtggagc | acgacacact | tgtctactcc | aaaaatatca | 480 |
| aagatacagt | ctcagaagac | caaagggcaa | ttgagacttt | tcaacaaagg | gtaatatccg | 540 |
| gaaacctcct | cggattccat | tgcccagcta | tctgtcactt | tattgtgaag | atagtggaaa | 600 |
| aggaaggtgg | ctcctacaaa | tgccatcatt | gcgataaagg | aaaggccatc | gttgaagatg | 660 |
| cctctgccga | cagtggtccc | aaagatggac | ccccacccac | gaggagcatc | gtggaaaaag | 720 |
| aagacgttcc | aaccacgtct | tcaaagcaag | tggattgatg | tgatatctcc | actgacgtaa | 780 | gggatgacgc acaatcccac tatccttcgc aagacccttc ctctatataa ggaagttcat    840 ttcatttgga gagaacacgg gggactctag aggatcc                              877

<210> SEQ ID NO 32
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 32
acccgggatg gatggttatt gtagcagaag g                                   31

<210> SEQ ID NO 33
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 33
gccgagctcg aatcaaatga gggcaatgcc                                     30

<210> SEQ ID NO 34
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 34
aatctagaca agtacagaag ctcaattccc                                     30

<210> SEQ ID NO 35
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 35
tgataatcat gtggaagcaa cc                                             22

<210> SEQ ID NO 36
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 36
cagcccgggt gatggaactg agcattcag                                      29

<210> SEQ ID NO 37
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 37
cgtgagctct gattagagtt tcaagtgcat g                                   31

<210> SEQ ID NO 38

```
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 38
tttcccgggt tgttgtcatg gcttctctgc                                      30

<210> SEQ ID NO 39
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 39
atggagctca tattcatggc caaaacac                                        28

<210> SEQ ID NO 40
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 40
gcacccggga aggaaatgg caggcgtc                                         28

<210> SEQ ID NO 41
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 41
tttcgatatc cacagtaccc tacttccatg c                                    31

<210> SEQ ID NO 42
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 42
tacccgggta ccattactct actacagctg c                                    31

<210> SEQ ID NO 43
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 43
gagagctcaa cagacaaaga ccagactgg                                       29

<210> SEQ ID NO 44
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 44
```

| | |
|---|---|
| acccccgggc aagtgatcaa agagaatgg | 29 |

<210> SEQ ID NO 45
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 45

| | |
|---|---|
| catgagctct ttctccaact cctctaccc | 29 |

<210> SEQ ID NO 46
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 46

| | |
|---|---|
| cccccgggtc cctattgcat gcctttc | 27 |

<210> SEQ ID NO 47
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 47

| | |
|---|---|
| ttgagctcac tcgatcttac tcatcc | 26 |

<210> SEQ ID NO 48
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 48

| | |
|---|---|
| agcccgggag atagagagat gggaggtcc | 29 |

<210> SEQ ID NO 49
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 49

| | |
|---|---|
| tcgagctctg gggcaacaat catttacc | 28 |

<210> SEQ ID NO 50
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 50

| | |
|---|---|
| tccccgggca tctgatctaa ttgttggtgg | 30 |

<210> SEQ ID NO 51
<211> LENGTH: 29
<212> TYPE: DNA

```
<213> ORGANISM: Artificial sequence
<220> FEATURE:
<223> OTHER INFORMATION: Single strand DNA oligonucleotide

<400> SEQUENCE: 51
ttggatatcg caccttatga catgggatc                                    29

<210> SEQ ID NO 52
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 52
ttcccgggta caaacatggc tagttccg                                     28

<210> SEQ ID NO 53
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 53
tcgagctcat caacctcact gcaccttg                                     28

<210> SEQ ID NO 54
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 54
tagtcactcc tgttctagat gaag                                         24

<210> SEQ ID NO 55
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 55
ctgagctcca ggatttttac ttagggaccc                                   30

<210> SEQ ID NO 56
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 56
tacccgggca tacagagatg gagaggc                                      27

<210> SEQ ID NO 57
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 57
acgagctcaa aggtgtttgc ttaggtcc                                     28
```

```
<210> SEQ ID NO 58
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 58
agcccgggag aaagatgatg aaaagggg                                           28

<210> SEQ ID NO 59
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 59
aagatatcaa atcccatgca aaacccc                                            27

<210> SEQ ID NO 60
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 60
aacccgggcg gcaacttaaa agaaaacc                                           28

<210> SEQ ID NO 61
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 61
aagagctcct ttgttggctt ctcaag                                             26

<210> SEQ ID NO 62
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 62
gacccgggac tgtaaaaaag catagg                                             26

<210> SEQ ID NO 63
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 63
gcgagctcag cttaaggatg atggggag                                           28

<210> SEQ ID NO 64
<211> LENGTH: 28
<212> TYPE: DNA
<213> ORGANISM: Artificial sequence
<220> FEATURE:
```

<223> OTHER INFORMATION: Single strand DNA oligonucleotide

<400> SEQUENCE: 64
atcccgggga tggtgagagg caaaattc                                28

<210> SEQ ID NO 65
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 65
acgagctcta gcaatggcga taacgtac                                28

<210> SEQ ID NO 66
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 66
atcccgggtt ccatgaaaag ggtctcg                                 27

<210> SEQ ID NO 67
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 67
gtgagctcta tcgtcgttgt ccttcagc                                28

<210> SEQ ID NO 68
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 68
tcgtgatcta accgatgcct t                                       21

<210> SEQ ID NO 69
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 69
acaatttccc gttcagcagt g                                       21

<210> SEQ ID NO 70
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 70
ggtggctcct acaaatgcca tc                                      22

<210> SEQ ID NO 71
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 71
aagttgggta acgccagggt                                               20

<210> SEQ ID NO 72
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 72
ctattcggct atgactgggc                                               20

<210> SEQ ID NO 73
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 73
atgtcctgat agcggtccgc                                               20

<210> SEQ ID NO 74
<211> LENGTH: 1344
<212> TYPE: DNA
<213> ORGANISM: Gossypium hirsutum

<400> SEQUENCE: 74
tgctcccttg ctacaccacc ctcggaggag gagcagcaga cccttaaagg gtttcgcagt     60
gatatttggg tccgtcgttt tcctactctc actggtcata ttaatcgtta accaaagccc    120
ggagccatta gcaagtaacc ccagtagtgt aacggaggca gggtcgtatt caatggcggc    180
gcagccaaga gggatagctg aaggagtttc agccaagtca aacccatcac tttttgacaa    240
agttgggttt aattggacaa acgctatgtt ttactggcaa agaactgcct accactttca    300
gcctcaaaag aattggatga atggtaggtt acctaattat aatttaagtt acttcttttg    360
attttcgtca ctaaaccttt cattttagtt tactattttt aaacttaaat atgatttcct    420
tttaataatc gaatttaatt tgttgtcttt ttcttactat gcttgcacgt tggttcggca    480
caacttacgt atcttgcttc agatcctgac ggtgagttct catcacatct aaattcttgt    540
tgggacaata ctgttagtca accatttcat caatcaatgc gtaaaacaca aaaatatcga    600
atcagaaatt tgtgaccaac ccaatctgct agttcttcca aatttgagca tttcaacctt    660
gatttgcaat taagttagc ttctacattg aattgaatca tatcttaccc tttttcttct    720
actagatcca cttataattt tattttttcaa tactcattta attaaagtaa ataatttaaa    780
taatttgttt catataaaat atatatattc tacatcaata agatactaat atcgaatcca    840
ccatttgtgg tataataaat gcaattatat tacaaaaaag ttaataaaat attagtagca    900
tagaattaat taatttaaaa aaatatgatt ttttagcag aattaaaaaa aacaaatatc      960
ttataaaaaa aataaatatt aaagaaaaa agacatatga taacccttag tttacaatct    1020
ataagttaca aaaaaatagt tacttgaccg tttggtttgt ttacctgtcg ttctaacgtt    1080

-continued

```
taagtcctaa ctaactagtt ttgcaaaacc ttgcttctgt acatcaccat gtaatagcat    1140 gtggttttt tagtaattat attaaactct aatagtttaa ttaaagtagt atgtgacata    1200
atggaacaaa aatacgatgg tcgcaggtcc gttatatcac aagggatggt accatctttt    1260
ctatcaatac aaccctgatt cagccatatg gggcaacatc acttggggcc acgctgtatc    1320
aaaggacctc attcacggtt ctat                                          1344
```

```
<210> SEQ ID NO 75
<211> LENGTH: 556
<212> TYPE: DNA
<213> ORGANISM: Gossypium hirsutum

<400> SEQUENCE: 75
tccacaacat tgacgtcagc cggcgccgcc gccgccacca tcaaactctc cctctctccc     60
ttccctcacc cttcttcctc ccatccttac caaattctca acaacttagt cacttcttct    120
gttgcaagag cccaccacct caaacaycccc aaagccaagg ccgataatac tacctcttct    180
cttctcaggg ctycccctatt tyctcacagt tatgggggct acactatctc cctcaaattt    240
ggaactccgc ctcaaaccct tcctttcrty atggacacyg ggagcagcct ctcctggttc    300
ccttgcacct ctcgttacct ttgttcccaa tgcgcwttcc ccaatgttga ccctgcaaaa    360
atccccactt tgcccctaa ackttcatct tccarkaagc tcgtaggttg yagaaacccc    420
aagtgtagtt ggcttttgg ccccgacgtt gagtctcgtt gccaagactg tgaacccact    480
tccgaaaact gcactcaaac ytgccctcct tacataattc aatacggttt aggttccact    540
gctgggcttc tattag                                                   556
```

```
<210> SEQ ID NO 76
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 76
tttttttttt tgtttgttgt ggggtgt                                        28
```

```
<210> SEQ ID NO 77
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 77
tttttgtttg ttgtggg                                                   17
```

```
<210> SEQ ID NO 78
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 78
tttttttttt tgtttgttgt ggggtgt                                        28
```

```
<210> SEQ ID NO 79
<211> LENGTH: 20
<212> TYPE: DNA
<213> ORGANISM: Artificial sequence
```

```
<220> FEATURE:
<223> OTHER INFORMATION: Single strand DNA oligonucleotide

<400> SEQUENCE: 79
ctggggttac ttgctaatgg                                               20

<210> SEQ ID NO 80
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 80
tttttgtttg ttgtggg                                                  17

<210> SEQ ID NO 81
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 81
gctccgggct ttggttaacg                                               20

<210> SEQ ID NO 82
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 82
ggctttggga tgtttgaggt gg                                            22

<210> SEQ ID NO 83
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 83
tttttgtttg ttgtggg                                                  17

<210> SEQ ID NO 84
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 84
ggtggtgggc tcttgcaaca g                                             21

<210> SEQ ID NO 85
<211> LENGTH: 969
<212> TYPE: DNA
<213> ORGANISM: Gossypium hirsutum

<400> SEQUENCE: 85
ggtggtgggc tcttgcaaca gaggcaattt tctaccggaa atgaaggaag gaatgaagga    60
ggcggtagag agaagagcac agaaaatgtc ttacagaaat tgaaagggta agacattttc   120
```

```
cttaaaatgt aacacatttt ctcttgtttt ggagttcatt ttccaaatgg aaaatgtttt      180
ccgccaatca aaagctgaaa aagttaaaaa tgattttctg gaaaatcaat ccgtcaatc       240 aaacagaccc ttagtctatt ctctccaatt aaatcattct tagtccttat acttttttaa     300
atttctatct cgatacaaaa gacaaccatt gaatctatta aattacccttt gtgtaaatga    360 tatatgaaaa taataaattg atatgacata acgcatgcga taatatatgt aaaaatcacc    420
aattacaggt acaaaaaaat ggttatggac taaatccgta acttgcgcat gataaacgaa     480
gtggcataat ggataattca gtgttttaca atgtcaaaat agcagcaccg taatcgaaca    540
tgataccttg gtccagttgt gctgtttacc gttggtatag tatttctact ctctctctat    600
aaagagagaa cgggacaaac atcatcccca ccgctatgcc tattccccca ctcaaattca    660
tttcactttt aaataccaat taatattact tacacttact tccccttac aaatagataa      720 tccaaaagca gagcaaaaac agagataacc attctttttc ttttgttgtt gttgttgtcg    780
tcgtcatggc ttctcttcct ttcatcttct tcttatcttt ctttataatc tccacaacat    840
tgacgtcagc cggcgccgcc gccgccacca tcaaactctc cctctctccc ttccctcacc    900
cttcttcctc ccatccttac caaattctca acaacttagt cacttcttct gttgcaagag    960
cccaccacc                                                             969

<210> SEQ ID NO 86
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 86
attcaagctt tttttgtttg ttgtgggggg                                      29

<210> SEQ ID NO 87
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 87
ttggatcctt gggcattgag cttctgtac                                       29

<210> SEQ ID NO 88
<211> LENGTH: 1040
<212> TYPE: DNA
<213> ORGANISM: Gossypium hirsutum

<400> SEQUENCE: 88
aagctttttt tgtttgttgt gggggtgtta tttgaagtag catagcattt aaatcgaatt      60
aattgaagca gctcctttaa tttagttttg ttggttgtca atgccaataa aaaggagaca    120
gggtttgaat aatgcaatgc aattcaagac ccaatgatcc taacaaacat tcaaggagca    180
cactcaaatc ccaacaacca ttccatcctg atggatgtgg aaaagcaaat ttaattaagg    240
agcctctcaa acttagagct cttgccacag cacatgatgc attttcaac agatcagaac     300 aagtacaagg acaattaatc ctagattatc tcaacagcat gccacatgac ccatgttcca    360
tttcgtatac atatgtctgc catttaattt aaaggtaaac atttgtgatg ccaatgccaa    420
tgccttattc acctcacaaa tcagtatcca taaactagct gttttcaggc caggaggacc    480
aacatgctca agacttggca ttccctaatg ctgtgtgtcc attggtcatt gcacgtaaat    540
```

-continued

```
tggctctgtc ttcatgcttc caaattatta ttattaatga agaaaaataa tttactctct      600
gaaatcttgc aacgcaagcc acaacccaga agctagagaa gacaaataat acgatgataa      660
tttataacta tatgtatagt agtgtaaatg gcaatatata ttaatataaa atcctacccc      720
aaaagcaagc aaatgagttt gactaccagg tgcagctgca tgcatgcatg catgggatgc      780
cctacctttt caactgtccc tcttgtttca ctgtatagca ttcaccagat ctgatctaat      840
gggaccacct ctctctccca gctaaattgg acaacaacca atccaagctc aagacatata      900
aatctcttct ctttctctct atgttgttct ctctttaatt ttacctacca ttacccttt       960 ctacttaatc tctcattgct tacttatatt gtaagtgtga ccaagtaaac caagtacaga      1020
agctcaatgc ccaaggatcc                                                  1040
```

```
<210> SEQ ID NO 89
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 89
ttaaagcttt gggctcttgc aacagaggc                                        29
```

```
<210> SEQ ID NO 90
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 90
aaggatccga cgacgacaac aacaacaac                                        29
```

```
<210> SEQ ID NO 91
<211> LENGTH: 792
<212> TYPE: DNA
<213> ORGANISM: Gossypium hirsutum

<400> SEQUENCE: 91
aagctttggg ctcttgcaac agaggcaatt ttctaccgga aatgaaggaa ggaatgaagg       60
aggcggtaga gagaagagca cagaaaatgt cttacagaaa ttgaaagggt aagacatttt      120
ccttaaaatg taacacattt tctcttgttt tggagttcat tttccaaatg gaaaatgttt      180
tccgccaatc aaaagctgaa aaagttaaaa atgattttct ggaaaatcaa ttccgtcaat      240
caaacagacc cttagtctat tctctccaat taaatcattc ttagtcctta tactttttta      300
aatttctatc tcgatacaaa agacaaccat tgaatctatt aaattacctt tgtgtaaatg      360
atatatgaaa ataataaatt gatatgacat aacgcatgcg ataatatatg taaaaatcac      420
caattacagg tacaaaaaaa tggttatgga ctaaatccgt aacttgcgca tgataaacga      480
agtggcataa tggataattc agtgttttac aatgtcaaaa tagcagcacc gtaatcgaac      540
atgataccct tggtccagtt gtgctgtttac cgttggtata gtatttctac tctctctcta      600
taaagagaga acgggacaaa catcatcccc accgctatgc ctattccccc actcaaattc      660
atttcacttt taaataccaa ttaatattac ttacacttac ttcccccttta caaatagata      720 atccaaaagc agagcaaaaa cagagataac cattcttttt cttttgttgt tgttgttgtc      780
gtcgtcggat cc                                                          792
```

<210> SEQ ID NO 92
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 92
aaatctagat aagttgataa agctaatttc tc                                    32

<210> SEQ ID NO 93
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 93
tttcccggga cctggaggca atc                                              23

<210> SEQ ID NO 94
<211> LENGTH: 1969
<212> TYPE: DNA
<213> ORGANISM: Nicotiana tabacum

<400> SEQUENCE: 94
tctagataag ttgataaagc taatttctca ttttagctac catcgctagt aatcgtggca        60
ataactaccc taactatagc atttattgct accaaataaa atttggcagc taatcataat       120
tttttgtcat gaatcaatag ttattgtagc aatagttatc tcttagccac aataaattat       180
ttaaaataaa atattatagc taaataaata ttttgctttt aagttctaaa agcttgtggc       240
aatagttaaa tgatatagtc acagatttat tggtataatt gaattatgtt gctaatttct       300 tagtttttg ccacgagtta aaaattacca atagctatag taacttttta atcacaataa        360
aatatttgaa agaaaatatt gtagctaaat gaatattttt tccttcaagt tattaaaagt       420
tgtggcaata taggttaaat tagccacatg tttcttgctt taatagaatt ttgtagctaa       480
tcattaactt ttaccacgag ttgaacttaa tataacaaca ataaccttt aaccataata         540 aagcgattta aatcaaatat tactaaataa ataactttgc tttcaagttt ctataaaatc       600
atggcaatag tcattacgat aaaatgatat aaccacgaat atattgcaac gataaattct       660
gtaactaatc attagttttt gcgacgaggt aaatttttccg tcacagtagc aatcttctag      720
gcacattaaa aatttgaaac aaaatttttgt agtcaaataa atatttatct tcttatttta      780
agaaaataaa aatagttaga taatagttac tactatttgt catgaaaata tcaatagata       840
caaatttaaa gtgactataa atttacgagt ttactatact ttagtcgtac agtttgcaat       900
aatagtattt taaccacaat tagttatatg tacaaaataa cataagtgaa taacttttt        960 tcaatgagaa aataagagtt gctcaaacaa tatcaagtta caaaaattta attttaactg      1020
taaaagttat atttttccaa aataacataa actatagtaa ttatatatag tttgaagtat      1080
taataaaatt taaatatgca aaagttaatt ttaataaacc atttgtatgc ctaacttgta     1140
gcctctaaac tatttatttt gctttattta tcaaactcat attttatttt attgcacctt     1200
gttagttttg gacgttaatt atatatattt ggtgtaaaat ttaaaatata ttaacatttg     1260
tggagaattt atgtatgcct ggttcttaac tatttttttt tatataactg gttagagtaa     1320
tttcttatat ttcagtattt atttttaaat aagtcctcat aaatttgaaga ctttaaaagt    1380 ttttgtgtca ttcctctttt tatttaagaa attgaagaat tccgctaaat ttcatatttc     1440

```
cgctgttatt taactgttta tttcccttgt taatataatt ggtaagaagt tttaaaataa    1500
aggagttaat gattttctag gttcatggct tgcctagctt ctacgagtaa gcgccatcac    1560
gactcccgag gataaggaaa tccgggtcgt agcattcact cacaaaaatt actaaaaaca    1620
aagtttaccc ttctcccaaa agtaaatttc atatttggct ccacataatg tgttcaatga    1680
gtcaagtgaa gtacttttca tgacaaaaaa aagttgctga aaaatgcata tctcatattt    1740 ttttttaga gaaatcccat ttcttgccta aacgaaagcc tataaaagag catatattgc    1800
aacaacagtt tgcagaaact atcaagtcaa ataatccccc ctttaattcc ctcccaaaat    1860
gcagttcttc aacttctttt ccctttcct ttttgtgtca tttctctttt tatttaagaa    1920
atggaagaat tccaatagcc aaaccaaaag attgcctcca ggtcccggg              1969
```

<210> SEQ ID NO 95
<211> LENGTH: 198
<212> TYPE: PRT
<213> ORGANISM: Gossypium hirsutum

<400> SEQUENCE: 95

```
Met Val Arg Gly Lys Ile Gln Met Lys Arg Ile Glu Asn Ala Thr Ser
1               5                   10                  15

Arg Gln Val Thr Phe Ser Lys Arg Arg Asn Gly Leu Leu Lys Lys Ala
            20                  25                  30

Tyr Glu Leu Tyr Val Leu Cys Asp Ala Glu Val Ala Val Ile Ile Phe
        35                  40                  45

Ser His Lys Gly Lys Leu Tyr Glu Phe Ser Ser Ser Asp Asn Met Gln
    50                  55                  60

Asn Thr Ile Glu Arg Tyr Arg Gln Tyr Lys Lys Asp Val Gln Ser Asn
65                  70                  75                  80

Ile Pro Glu Phe Asp Arg Tyr Thr Gln Gln Leu Arg Leu Glu Ala Glu
                85                  90                  95

Asn Met Ala Lys Lys Ile Glu Phe Leu Glu Val Ser Lys Arg Arg Met
            100                 105                 110

Leu Gly Gln Asn Leu Gly Ser Cys Ser Ile Asp Glu Leu Gln Glu Val
        115                 120                 125

Glu Asn Gln Leu Glu Arg Ser Leu Arg Asn Ile Arg Ala Arg Lys Gly
    130                 135                 140

Tyr Leu Phe Lys Glu Gln Ile Leu Gln Leu Lys Ala Lys Glu Arg Tyr
145                 150                 155                 160

Met Gln Glu Glu Asn Ala Lys Leu Ser Ala Lys Asn Asn Gly Thr Thr
                165                 170                 175

Cys Ser Gln Gln Asn Ala Glu Val Glu Thr Glu Leu Phe Leu Gly Leu
            180                 185                 190

Pro Glu Asn Arg Cys Ser
        195
```

<210> SEQ ID NO 96
<211> LENGTH: 463
<212> TYPE: PRT
<213> ORGANISM: Gossypium hirsutum

<400> SEQUENCE: 96

```
Met Lys Arg Val Ser Asn Ile Tyr Ile Glu Ala Lys Lys His Leu Ser
1               5                   10                  15

Asp Leu Leu Thr Asn Glu Asp Gln Asn Glu Asp Leu Leu Ser Thr Gln
            20                  25                  30
```

```
Val Pro Lys Thr Leu Gly Arg Ile Leu Ser Leu Pro Glu Tyr Asn Thr
         35                  40                  45

Ser Pro Val Ser Ser Pro Gly Gln Asn Leu Glu His Ser Phe Thr Thr
 50                  55                  60

Ala His Met Arg Phe Ala Gly Ser Asp Lys Leu Gln Met Val Ser Glu
 65                  70                  75                  80

Asn Asp Arg Phe Val Ser Leu Leu Ser Met Arg Ala Glu Lys Thr Asp
                 85                  90                  95

Gly Gln Leu Cys Ile Ser Glu Asn Lys Ser Asp Asn Glu Val Glu Ser
             100                 105                 110

Asp Asn Ala Ile Ser Asn Asn Leu Asp Thr Ser Val Asn Asn Asp Lys
         115                 120                 125

Glu Asp Pro Ile Phe Cys Ser Ile Lys Asp Glu Leu Ser Ser Lys Glu
     130                 135                 140

Ser Val Ser Ile Val Lys Ala Thr Glu Met Met Val His Glu Glu Ser
145                 150                 155                 160

Lys Ser Leu Asp Ile Ser Ser Glu Thr Ser Gly Ser Ser Ile Ile Thr
                 165                 170                 175

Asp Asp Lys Asn Val Asp Ile Tyr Glu Val Cys Asp Glu Lys Gln Asn
             180                 185                 190

Pro Trp Tyr Leu Lys Gln Asp Ser Ser Glu Val Asp Gln Gln Pro Phe
         195                 200                 205

Ser Pro Leu Ser Ser Pro Ser Asp Ser Ser Val Met Lys Lys Val Glu
     210                 215                 220

Cys Leu Glu Ser Val Thr Asp Ile Pro Glu Arg Ser Ser Pro Val Ser
225                 230                 235                 240

Val Leu Glu Pro Ile Phe Ala Asp Asp Leu Ile Ser Pro Ala Ser Ile
                 245                 250                 255

Arg Ser Tyr Ser Gly Glu Thr Ser Ile Gln Pro Leu Arg Ile Arg Phe
             260                 265                 270

Glu Glu His Asp Ser Leu Ala Thr Asn Gln Ser Asn Arg Ile Lys Thr
         275                 280                 285

Cys Met Asn Asp Lys Glu Ser Ile Phe Glu His Ile Lys Ala Val Leu
     290                 295                 300

Gln Ala Ser Ser Phe Ser Trp Asp Glu Val Tyr Ile Arg Ser Leu Ser
305                 310                 315                 320

Ser Asp Leu Leu Ile Asp Pro Leu Leu Val Asp Glu Val Glu Tyr Leu
                 325                 330                 335

Pro Asn Gln Leu Cys Gln Asp Gln Lys Leu Leu Phe Asp Cys Ile Asn
             340                 345                 350

Glu Val Val Arg Glu Val Cys Glu Tyr Tyr Phe Gly Ser Pro Ser Val
         355                 360                 365

Ser Phe Val Lys Pro Asn Ile Arg Pro Ile Pro Asn Met Gln Asn Thr
     370                 375                 380

Ile Gln Glu Val Trp Glu Gly Val Tyr Trp His Leu Leu Pro Thr Pro
385                 390                 395                 400

Leu Pro Cys Thr Leu Asp Leu Val Arg Lys Asp Leu Ala Lys Thr
                 405                 410                 415

Gly Thr Trp Met Asp Leu Gln Leu Asp Thr Gly Tyr Ile Gly Val Glu
             420                 425                 430

Ile Gly Glu Ala Ile Phe Glu Asp Leu Val Glu Asp Thr Ile Thr Ser
         435                 440                 445
```

```
Tyr Ile Asn Gly Ser Trp Glu Cys Glu Tyr Asn Val Leu Pro Ala
    450                 455                 460
```

<210> SEQ ID NO 97
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 97
tcagattccg ccttgatagc a                                             21

<210> SEQ ID NO 98
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 98
ctctgtggtt gacctcactg tga                                           23

<210> SEQ ID NO 99
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 99
cctaccaaga ttcactcccg atc                                           23

<210> SEQ ID NO 100
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 100
cctcttacca tagccagaat gacg                                          24

<210> SEQ ID NO 101
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 101
tccacaacat tgacgtcagc c                                             21

<210> SEQ ID NO 102
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 102
ctaatagaag cccagcagtg g                                             21

<210> SEQ ID NO 103
<211> LENGTH: 32
<212> TYPE: DNA

```
<213> ORGANISM: Artificial sequence
<220> FEATURE:
<223> OTHER INFORMATION: Single strand DNA oligonucleotide

<400> SEQUENCE: 103
aaatctagat aagttgataa agctaatttc tc                              32

<210> SEQ ID NO 104
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 104
tttcccggga cctggaggca atc                                        23

<210> SEQ ID NO 105
<211> LENGTH: 1969
<212> TYPE: DNA
<213> ORGANISM: Gossypium hirsutum

<400> SEQUENCE: 105
tctagataag ttgataaagc taatttctca ttttagctac catcgctagt aatcgtggca    60
ataactaccc taactatagc atttattgct accaaataaa atttggcagc taatcataat   120
tttttgtcat gaatcaatag ttattgtagc aatagttatc tcttagccac aataaattat   180
ttaaaataaa atattatagc taaataaata ttttgctttt aagttctaaa agcttgtggc   240
aatagttaaa tgatatagtc acagatttat tggtataatt gaattatgtt gctaatttct   300
tagttttttg ccacgagtta aaattacca atagctatag taacttttta atcacaataa   360
aatatttgaa agaaaatatt gtagctaaat gaatattttt tccttcaagt tattaaaagt   420
tgtggcaata taggttaaat tagccacatg tttcttgctt taatagaatt ttgtagctaa   480
tcattaactt ttaccacgag ttgaacttaa tataacaaca ataaccttt aaccataata    540
aagcgattta aatcaaatat tactaaataa ataactttgc tttcaagttt ctataaaatc   600
atggcaatag tcattacgat aaaatgatat aaccacgaat atattgcaac gataaattct   660
gtaactaatc attagttttt gcgacgaggt aaattttccg tcacagtagc aatcttctag   720
gcacattaaa aatttgaaac aaaattttgt agtcaaataa atatttatct tcttatttta   780
agaaaataaa aatagttaga taatagttac tactatttgt catgaaaata tcaatagata   840
caaatttaaa gtgactataa atttacgagt ttactatact ttagtcgtac agtttgcaat   900
aatagtattt taaccacaat tagttatatg tacaaaataa cataagtgaa taacttttt    960
tcaatgagaa aataagagtt gctcaaacaa tatcaagtta caaaaattta attttaactg   1020
taaaagttat attttccaa aataacataa actatagtaa ttatatatag tttgaagtat    1080
taataaaatt taaatatgca aaagttaatt ttaataaacc atttgtatgc ctaacttgta   1140
gcctctaaac tattttattt gctttatta tcaaactcat attttatttt attgcacctt    1200
gttagttttg gacgttaatt atatatattt ggtgtaaaat ttaaatata ttaacatttg    1260
tggagaattt atgtatgcct ggttcttaac tatttttttt tatataactg gttagagtaa   1320
tttcttatat ttcagtattt atttttaaat aagtcctcat aaattgaaga ctttaaaagt   1380
ttttgtgtca ttcctctttt tatttaagaa attgaagaat tccgctaaat ttcatatttc   1440
cgctgttatt taactgttta tttcccttgt taatataatt ggtaagaagt tttaaaataa   1500
aggagttaat gattttctag gttcatggct tgcctagctt ctacgagtaa gcgccatcac   1560
```

```
gactcccgag gataaggaaa tccgggtcgt agcattcact cacaaaaatt actaaaaaca    1620
aagtttaccc ttctcccaaa agtaaatttc atatttggct ccacataatg tgttcaatga    1680
gtcaagtgaa gtactttca tgacaaaaaa aagttgctga aaaatgcata tctcatattt     1740 ttttttaga gaaatcccat ttcttgccta aacgaaagcc tataaagag catatattgc      1800 aacaacagtt tgcagaaact atcaagtcaa ataatccccc ctttaattcc ctcccaaat     1860 gcagttcttc aacttctttt cccttttcct ttttgtgtca tttctctttt tatttaagaa    1920
atggaagaat ccaatagcc aaaccaaaag attgcctcca ggtcccggg                 1969
```

<210> SEQ ID NO 106
<211> LENGTH: 356
<212> TYPE: PRT
<213> ORGANISM: Gossypium hirsutum

<400> SEQUENCE: 106

```
Met Asp Gly Tyr Cys Ser Arg Arg Val Ile Met Phe Leu Val Phe Ala
1               5                   10                  15

Phe Ala Ala Ile Ser Arg Gly Tyr Gly Gln Glu Ser Thr Thr Leu Val
            20                  25                  30

Pro Ala Ile Ile Thr Phe Gly Asp Ser Val Val Asp Val Gly Asn Asn
        35                  40                  45

Asp Tyr Leu Pro Thr Ile Phe Lys Ala Asn Tyr Pro Pro Tyr Gly Arg
    50                  55                  60

Asp Phe Ala Asn Lys Lys Pro Thr Gly Arg Phe Cys Asn Gly Lys Leu
65                  70                  75                  80

Ala Thr Asp Ile Thr Ala Glu Thr Leu Gly Phe Thr Thr Tyr Pro Pro
                85                  90                  95

Ala Tyr Leu Ser Pro Glu Ala Ser Gly Lys Asn Leu Leu Gly Ala
            100                 105                 110

Asn Phe Ala Ser Ala Gly Ser Gly Tyr Asp Asp Lys Ala Ala Met Val
        115                 120                 125

Asn His Ala Ile Thr Leu Thr Gln Gln Leu Glu Tyr Phe Lys Glu Tyr
    130                 135                 140

Gln Ala Lys Leu Ala Lys Val Ala Gly Ser Thr Lys Ser Ala Ser Ile
145                 150                 155                 160

Thr Lys Asp Ala Leu Tyr Val Leu Ser Ala Gly Ser Gly Asp Phe Leu
                165                 170                 175

Gln Asn Tyr Tyr Val Asn Pro Leu Leu Asn His Ala Tyr Thr Pro Asp
            180                 185                 190

Gln Tyr Gly Ser Phe Leu Ile Asp Thr Phe Thr Asn Phe Val Lys Asn
        195                 200                 205

Leu Tyr Gly Leu Gly Ala Arg Lys Ile Gly Val Thr Ser Leu Pro Pro
    210                 215                 220

Leu Gly Cys Val Pro Leu Ala Arg Thr Leu Phe Gly Tyr His Glu Lys
225                 230                 235                 240

Gly Cys Ile Ser Arg Phe Asn Thr Asp Ala Gln Gln Phe Asn Lys Lys
                245                 250                 255

Leu Asn Ala Ala Ala Ala Asn Leu Gln Lys Gln His Pro Gly Leu Lys
            260                 265                 270

Ile Val Val Phe Asp Ile Phe Lys Ala Leu Tyr Asp Ile Val Lys Ser
        275                 280                 285

Pro Ser Asn Tyr Gly Phe Val Glu Ala Thr Lys Gly Cys Cys Gly Thr
    290                 295                 300
```

```
Gly Thr Val Glu Thr Thr Ala Phe Leu Cys Asn Pro Lys Ala Pro Gly
305                 310                 315                 320

Thr Cys Ser Asn Ala Ser Gln Tyr Val Phe Trp Asp Ser Val His Pro
            325                 330                 335

Ser Gln Ala Ala Asn Gln Val Leu Ala Asp Ala Leu Ile Val Gln Gly
        340                 345                 350

Ile Ala Leu Ile
        355

<210> SEQ ID NO 107
<211> LENGTH: 645
<212> TYPE: PRT
<213> ORGANISM: Gossypium hirsutum

<400> SEQUENCE: 107

Met Glu Ala Ser Ser Thr Ser His Asp Pro Ala Leu Phe His Ala
1               5                   10                  15

Pro Leu Leu Tyr His Pro Arg Arg Ser Ser Arg Pro Leu Lys Gly
            20                  25                  30

Phe Ala Val Ile Ile Gly Ser Val Val Phe Leu Leu Ser Leu Val Thr
            35                  40                  45

Leu Ile Val Asn Gln Ser Pro Glu Pro Leu Ala Ser Asn Pro Ser Ser
50                  55                  60

Val Thr Glu Ala Gly Ser Tyr Ser Met Ala Ala Gln Pro Arg Gly Ile
65                  70                  75                  80

Ala Glu Gly Val Ser Ala Lys Ser Asn Pro Ser Leu Phe Asp Lys Val
                85                  90                  95

Gly Phe Asn Trp Thr Asn Ala Met Phe Tyr Trp Gln Arg Thr Ala Tyr
            100                 105                 110

His Phe Gln Pro Gln Lys Asn Trp Met Asn Asp Pro Asp Gly Pro Leu
        115                 120                 125

Tyr His Lys Gly Trp Tyr His Leu Phe Tyr Gln Tyr Asn Pro Asp Ser
    130                 135                 140

Ala Ile Trp Gly Asn Ile Thr Trp Gly His Ala Val Ser Thr Asp Leu
145                 150                 155                 160

Ile His Trp Phe Tyr Leu Pro Leu Ala Met Val Pro Asp Gln Trp Tyr
                165                 170                 175

Asp Ile Asn Gly Cys Trp Thr Gly Ser Ala Thr Leu Leu Pro Asp Gly
            180                 185                 190

Arg Ile Val Met Leu Tyr Thr Gly Ser Thr Asn Asp Ser Val Gln Val
        195                 200                 205

Gln Asn Leu Ala Tyr Pro Ala Asn Leu Ser Asp Pro Leu Leu Leu Gln
    210                 215                 220

Trp Leu Lys Tyr Pro Gly Asn Pro Val Val Pro Pro Thr Gly Ile
225                 230                 235                 240

Glu Asp Glu Glu Phe Arg Asp Pro Thr Thr Ala Trp Leu Gly Pro Asp
                245                 250                 255

Gly Ser Trp Arg Ile Val Val Gly Thr Arg Phe Asn Thr Thr Ile Gly
            260                 265                 270

Thr Ala Leu Val Phe Gln Thr Thr Asn Phe Ser Asp Tyr Glu Leu Leu
        275                 280                 285

Asp Gly Val Leu His Ala Val Pro Gly Thr Gly Met Trp Glu Cys Val
    290                 295                 300

Asp Phe Tyr Pro Val Ala Ile Asn Gly Ser Val Gly Leu Asp Thr Thr
```

```
                305                 310                 315                 320
Ala Leu Gly Pro Gly Ile Lys His Val Leu Lys Ala Ser Leu Asp Asp
                325                 330                 335

Thr Lys Val Asp His Tyr Ala Ile Gly Thr Tyr Asp Met Ile Thr Asp
                340                 345                 350

Lys Trp Thr Pro Asp Asn Pro Glu Glu Asp Val Gly Ile Gly Leu Lys
                355                 360                 365

Val Asp Tyr Gly Arg Tyr Tyr Ala Ser Lys Thr Phe Phe Asp Gln Ser
                370                 375             380

Lys Gln Arg Arg Ile Leu Tyr Gly Trp Val Asn Glu Thr Asp Ser Glu
385                 390                 395                 400

Ala Asp Asp Leu Glu Lys Gly Trp Ala Ser Ile Gln Thr Ile Pro Arg
                405                 410                 415

Ser Val Leu Tyr Asp Asn Lys Thr Gly Thr His Leu Leu Gln Trp Pro
                420                 425                 430

Val Glu Glu Val Glu Ser Leu Arg Leu Asn Ala Thr Val Phe Lys Asp
                435                 440                 445

Val Val Glu Ala Gly Ser Val Pro Leu Asp Ile Gly Thr Ala
                450                 455                 460

Thr Gln Leu Asp Ile Leu Ala Glu Phe Glu Ile Glu Thr Leu Val Leu
465                 470                 475                 480

Asn Ser Thr Glu Asp Glu Val Ser Asp Cys Gly Asp Gly Ala Val Asp
                485                 490                 495

Arg Ser Thr Tyr Gly Pro Phe Gly Val Leu Val Ile Ala Asp Asp Ser
                500                 505                 510

Leu Ser Glu Leu Thr Pro Ile Tyr Phe Arg Pro Leu Asn Thr Ser Asp
                515                 520                 525

Gly Ser Leu Glu Thr Tyr Phe Cys Ala Asp Glu Thr Arg Ser Ser Lys
                530                 535                 540

Ala Pro Asp Val Thr Lys Arg Val Tyr Gly Gly Lys Ile Pro Val Leu
545                 550                 555                 560

Asp Asp Glu Asn Tyr Asn Met Arg Val Leu Val Asp His Ser Val Val
                565                 570                 575

Glu Ser Phe Gly Gly Gly Gly Arg Thr Val Ile Thr Ser Arg Val Tyr
                580                 585                 590

Pro Thr Glu Ala Ile Tyr Gly Ala Ala Arg Leu Phe Leu Phe Asn Asn
                595                 600                 605

Ala Ser Gly Val Asn Val Lys Ala Thr Leu Lys Ile Trp Glu Met Asn
                610                 615                 620

Ser Ala Phe Ile Arg Pro Phe Pro Phe Glu Glu Thr Leu Phe Gln Glu
625                 630                 635                 640

Met Val Ala Ser Thr
                645

<210> SEQ ID NO 108
<211> LENGTH: 180
<212> TYPE: PRT
<213> ORGANISM: Gossypium hirsutum

<400> SEQUENCE: 108

Met Glu Leu Ser Ile Gln Lys Ile Glu Ala Leu Ile Arg Leu Ser Thr
1               5                   10                  15

Ile Val Met Leu Val Leu Thr Ala Cys Leu Ile Gly Leu Asp Ser Gln
                20                  25                  30
```

```
Thr Lys Val Ile Phe Tyr Val Gln Lys Lys Ala Ser Phe Lys Asp Leu
        35                  40                  45

Arg Ala Leu Val Gly Leu Leu Tyr Ile Thr Ser Leu Ala Ala Ala Tyr
    50                  55                  60

Asn Leu Leu Gln Leu Cys Cys Ser Ser Phe Ser Ala Ser Tyr Lys Gly
65                  70                  75                  80

Thr Ser Leu Gln Ser Tyr Ala Tyr Leu Ala Trp Leu Arg Tyr Ile Leu
                85                  90                  95

Asp Gln Ala Val Val Tyr Ala Val Phe Ala Gly Asn Leu Ala Ala Leu
                100                 105                 110

Glu His Ser Phe Leu Val Leu Thr Gly Glu Glu Asn Phe Gln Trp Leu
            115                 120                 125

Lys Trp Cys Asn Lys Tyr Thr Arg Phe Cys Thr Gln Ile Gly Gly Ser
    130                 135                 140

Leu Leu Cys Gly Phe Val Ala Ser Leu Leu Met Phe Ser Ile Ala Ser
145                 150                 155                 160

Ile Ser Ala Phe Asn Leu Phe Arg Leu Tyr Ser Pro Thr Lys Phe Met
                165                 170                 175

His Leu Lys Leu
        180

<210> SEQ ID NO 109
<211> LENGTH: 189
<212> TYPE: PRT
<213> ORGANISM: Gossypium hirsutum

<400> SEQUENCE: 109

Met Ala Glu Ile Leu Arg Lys Pro Ser Val Leu Lys Lys Leu Leu Leu
1               5                   10                  15

Glu Leu Asp Gln Val Val Gly Lys Asp Arg Phe Val Val Glu Ser Asp
                20                  25                  30

Ile Pro Lys Leu Thr Tyr Leu Gln Ala Val Val Lys Glu Val Phe Arg
                35                  40                  45

Leu His Pro Gly Val Pro Leu Ile Ile Pro Arg Arg Thr Asn Glu Ala
        50                  55                  60

Cys Glu Val Ala Gly Tyr His Ile Pro Lys His Cys Ile Val Tyr Val
65                  70                  75                  80

Asn Val Trp Gly Met Ala Arg Asp Pro Asn Val Trp Glu Asp Pro Leu
                85                  90                  95

Glu Phe Lys Pro Glu Arg Phe Ile Gly Ser Ser Val Asp Val Lys Gly
                100                 105                 110

Gln Asp Phe Asn Leu Leu Pro Phe Gly Thr Gly Arg Arg Ser Cys Val
            115                 120                 125

Gly Trp Pro Leu Ala His Arg Met Val His Tyr Tyr Leu Ala Ala Leu
    130                 135                 140

Leu His Ala Phe Gln Trp Glu Ser Pro Pro Asp Val Leu Asn Asp Leu
145                 150                 155                 160

Gly Glu Arg Val Gly Leu Thr Ile Gln Lys Gly Lys Ser Leu Leu Ser
                165                 170                 175

Thr Pro Lys Pro Arg Leu Pro Ala Ser Val Tyr Glu Arg
            180                 185

<210> SEQ ID NO 110
<211> LENGTH: 468
<212> TYPE: PRT
<213> ORGANISM: Gossypium hirsutum
```

<400> SEQUENCE: 110

```
Met Ala Ser Leu Pro Phe Ile Phe Phe Leu Ser Phe Phe Ile Ile Ser
1               5                   10                  15

Thr Thr Leu Thr Ser Ala Gly Ala Ala Ala Thr Ile Lys Leu Ser
            20                  25                  30

Leu Ser Pro Phe Pro His Pro Ser Ser His Pro Tyr Gln Ile Leu
            35                  40                  45

Asn Asn Leu Val Thr Ser Ser Val Ala Arg Ala His His Leu Lys His
        50                  55                  60

Pro Lys Ala Lys Ala Asp Asn Thr Thr Ser Ser Leu Leu Arg Ala Pro
65                  70                  75                  80

Leu Phe Ser His Ser Tyr Gly Gly Tyr Thr Ile Ser Leu Lys Phe Gly
                85                  90                  95

Thr Pro Pro Gln Thr Leu Pro Phe Val Met Asp Thr Gly Ser Ser Leu
            100                 105                 110

Ser Trp Phe Pro Cys Thr Ser Arg Tyr Leu Cys Ser Gln Cys Ala Phe
            115                 120                 125

Pro Asn Val Asp Pro Ala Lys Ile Pro Thr Phe Ala Pro Lys Leu Ser
            130                 135                 140

Ser Ser Ser Lys Leu Val Gly Cys Arg Asn Pro Lys Cys Ser Trp Leu
145                 150                 155                 160

Phe Gly Pro Asp Val Glu Ser Arg Cys Gln Asp Cys Glu Pro Thr Ser
                165                 170                 175

Glu Asn Cys Thr Gln Thr Cys Pro Pro Tyr Ile Ile Gln Tyr Gly Leu
            180                 185                 190

Gly Ser Thr Ala Gly Leu Leu Val Glu Asn Leu Ala Phe Pro Gln
            195                 200                 205

Lys Thr Phe Gln Asp Phe Leu Val Gly Cys Ser Ile Leu Ser Asn Arg
    210                 215                 220

Gln Pro Ala Gly Ile Ala Gly Phe Gly Arg Ser Ala Glu Ser Ile Pro
225                 230                 235                 240

Ser Gln Leu Gly Leu Lys Lys Phe Ser Tyr Cys Leu Val Ser Arg Arg
                245                 250                 255

Phe Asp Asp Thr Gly Val Ser Ser Asn Met Leu Leu Glu Thr Gly Ser
                260                 265                 270

Gly Ser Gly Asp Ala Lys Thr Pro Gly Leu Ser Tyr Thr Pro Phe Tyr
                275                 280                 285

Arg Asn Gln Val Ala Ser Asn Pro Val Phe Lys Glu Phe Tyr Val
290                 295                 300

Thr Leu Arg Lys Ile Leu Val Gly Asp Lys His Val Lys Val Pro Tyr
305                 310                 315                 320

Ser Tyr Leu Val Pro Gly Ser Asp Gly Asn Gly Gly Thr Ile Val Asp
                325                 330                 335

Ser Gly Ser Thr Phe Thr Phe Met Glu Arg Pro Val Phe Glu Val Val
                340                 345                 350

Ser Lys Glu Phe Glu Lys Gln Met Gly Asn Tyr Arg Arg Val Arg Glu
            355                 360                 365

Ile Glu Asn Arg Ser Gly Leu Ala Pro Cys Phe Asn Thr Ser Gly Tyr
    370                 375                 380

Thr Ser Ile Glu Ile Pro Glu Leu Ser Phe Gln Phe Lys Gly Gly Ala
385                 390                 395                 400

Lys Met Ala Leu Pro Leu Val Asn Tyr Phe Ser Phe Asp Gly Asp Asp
```

```
                            405                 410                 415
Lys Val Val Cys Leu Met Ile Val Ser Asn Asn Val Gly Gln Gly
            420                 425                 430

Ser His Ser Gly Pro Ala Ile Ile Leu Gly Ser Phe Gln Gln Gln Asn
            435                 440                 445

Tyr Tyr Ile Glu Phe Asp Ile Ala Asn Asn Arg Phe Gly Trp Ala Glu
            450                 455                 460

Arg Ser Cys Ala
465

<210> SEQ ID NO 111
<211> LENGTH: 451
<212> TYPE: PRT
<213> ORGANISM: Gossypium hirsutum

<400> SEQUENCE: 111

Met Ala Gly Val Glu Ala Gly Lys Glu Glu Ala Thr Ala Val Arg
1               5                   10                  15

Ile Thr Gly Lys Ser His Val Lys Pro Gly Lys Leu Ile Gly Arg Lys
            20                  25                  30

Glu Cys Gln Leu Val Thr Phe Asp Leu Pro Tyr Leu Ala Phe Tyr Tyr
            35                  40                  45

Asn Gln Lys Leu Leu Phe Tyr Lys Asn Asp Gly Gly Glu Phe Glu
50                  55                  60

Asp Lys Val Glu Lys Leu Lys Gly Gly Leu Arg Val Val Leu Glu Glu
65                  70                  75                  80

Phe Tyr Gln Leu Gly Gly Lys Leu Gly Lys Asp Asp Gly Val Leu
                    85                  90                  95

Arg Val Asp Tyr Asp Asp Asp Met Asp Gly Val Glu Val Val Glu Ala
                100                 105                 110

Val Ala Glu Gly Ile Thr Val Asp Glu Leu Thr Gly Asp Asp Gly Thr
            115                 120                 125

Ser Ser Phe Lys Glu Leu Ile Pro Phe Asn Gly Val Leu Asn Leu Glu
            130                 135                 140

Gly Leu His Arg Pro Leu Leu Ser Ile Gln Leu Thr Lys Leu Lys Asp
145                 150                 155                 160

Gly Val Ala Met Gly Cys Ala Phe Asn His Ala Ile Leu Asp Gly Thr
                165                 170                 175

Ser Thr Trp His Phe Met Ser Ser Trp Ala Gln Ile Cys Asn Gly Thr
            180                 185                 190

Ser Ser Ser Val Val Pro Pro Phe Leu Asp Arg Thr Thr Ala Arg
            195                 200                 205

Asn Thr Arg Val Lys Leu Asp Leu Ser Pro Val Val Ser Cys Asn Gly
210                 215                 220

Asp Asp Ala Thr Lys Gln Gly Gln Pro Ala Pro Gln Met Arg Glu Lys
225                 230                 235                 240

Leu Phe Arg Phe Ser Glu Ala Ala Val Asp Lys Ile Lys Ser Arg Val
                245                 250                 255

Asn Ser Thr Pro Pro Ser Asp Gly Ser Lys Pro Phe Ser Thr Phe
            260                 265                 270

Gln Ser Leu Ala Val His Ile Trp Arg His Val Ser Gln Ala Arg Asn
            275                 280                 285

Leu Lys Pro Glu Asp Tyr Thr Val Phe Thr Val Phe Ala Asp Cys Arg
    290                 295                 300
```

```
Lys Arg Val Asp Pro Pro Met Pro Asp Ser Tyr Phe Gly Asn Leu Ile
305                 310                 315                 320

Gln Ala Ile Phe Thr Ala Thr Ala Ala Gly Leu Leu Leu Glu Asn Pro
                325                 330                 335

Pro Ser Phe Gly Ala Ser Val Ile Gln Lys Ala Ile Glu Ser His Asp
            340                 345                 350

Ala Lys Ala Ile Asp Glu Arg Asn Lys Ala Trp Glu Ala Ala Pro Lys
        355                 360                 365

Ile Phe Gln Phe Lys Asp Ala Gly Val Asn Cys Val Ala Val Gly Ser
    370                 375                 380

Ser Pro Arg Phe Lys Val Tyr Glu Val Asp Phe Gly Trp Gly Lys Pro
385                 390                 395                 400

Val Gly Val Arg Ser Gly Ser Asn Asn Arg Phe Asp Gly Met Val Tyr
                405                 410                 415

Leu Tyr Gln Gly Lys Ser Gly Gly Arg Ser Ile Asp Val Glu Ile Thr
            420                 425                 430

Met Glu Ala Gln Ala Met Glu Lys Leu Glu Lys Asp Lys Glu Phe Leu
        435                 440                 445

Met Glu Val
    450

<210> SEQ ID NO 112
<211> LENGTH: 467
<212> TYPE: PRT
<213> ORGANISM: Gossypium hirsutum

<400> SEQUENCE: 112

Met Ser Thr Gln Ser Arg Ala Val Gly Gly Thr Glu His Asn Trp Cys
1               5                   10                  15

Arg Ala Val Val Gly Gly Thr Gly Ile Ala Val Leu Ala Ile Ile Ser
            20                  25                  30

Ser Lys Asn Pro Asp Val Ser His Leu Lys Asn Ala Leu His Lys Leu
        35                  40                  45

Gln Ile Ser His Pro Ile Leu Arg Ser Arg Leu His Tyr Ser Pro Thr
    50                  55                  60

Ala Asn Ser Tyr Ser Phe Val Thr Ser Pro Ser Pro Phe Ile Gln Ile
65                  70                  75                  80

Lys Tyr Phe Asn His Ser Thr Thr Cys Gln Ile Leu Glu Asn Asn Gln
                85                  90                  95

Asn Ile Ser Pro Leu His Leu Ile Leu Glu His Glu Leu Asn Gln Asn
            100                 105                 110

Ala Trp Val Ser Ser Ser Cys Thr Thr Lys His Asp Val Phe Phe Ala
        115                 120                 125

Ser Val Tyr Ala Leu Pro Gly Ala Thr Arg Trp Val Leu Val Leu Arg
    130                 135                 140

Leu His Ala Ala Ala Cys Asp Arg Thr Thr Ala Val Ser Leu Leu Arg
145                 150                 155                 160

Glu Leu Leu Thr Leu Met Ala Ile Glu Glu Glu Thr Gly Phe Gln
                165                 170                 175

Gln Gly Gln Lys Glu Ile Thr Met Asn Lys Gly Glu Ile Ser Leu Ala
            180                 185                 190

Met Glu Asp Ile Leu Pro Lys Gly Ile Val Lys Lys Thr Leu Trp Ala
        195                 200                 205

Arg Gly Val Asp Met Leu Ser Tyr Ser Val Asn Ser Leu Arg Phe Thr
    210                 215                 220
```

Asn Leu Arg Phe Lys Asp Ala Lys Ser Pro Arg Ser Thr Gln Val Val
225                 230                 235                 240

Arg Leu Leu Ile Asn Pro Asp Thr Gln Lys Ile Leu Thr Gly Cys
            245                 250                 255

Lys Ala Arg Gly Ile Lys Leu Cys Gly Ala Leu Gly Ala Ala Gly Leu
            260                 265                 270

Ile Ser Ala His Ser Ser Lys Ser Arg Ser Asp His Gln Lys Lys Lys
            275                 280                 285

Tyr Gly Val Val Thr Leu Thr Asp Cys Arg Ser Ile Leu Glu Pro Pro
            290                 295                 300

Leu Ser Asn His His Phe Gly Phe Tyr His Ser Ala Ile Leu Asn Thr
305                 310                 315                 320

His Ala Ile Lys Gly Gly Glu Lys Leu Trp Glu Leu Ala Glu Lys Val
            325                 330                 335

Tyr Thr Val Phe Thr His Tyr Lys Ser Cys Asn Lys His Leu Ser Asp
            340                 345                 350

Met Ala Asp Leu Asn Phe Leu Met Cys Arg Ala Met Glu Asn Pro Gly
            355                 360                 365

Leu Thr Pro Ser Ala Ser Leu Arg Thr Cys Leu Ile Ser Val Phe Glu
370                 375                 380

Asp Thr Val Ile Asp Glu Ser Ser Asn Gln Gln Asn Gln Val Gly Val
385                 390                 395                 400

Glu Asp Tyr Met Gly Cys Ala Ser Ala His Gly Ile Ala Pro Ser Ile
            405                 410                 415

Ala Ile Phe Asp Thr Ile Arg Asp Gly Arg Leu Asp Cys Ile Cys Val
            420                 425                 430

Tyr Pro Ser Pro Leu His Ser Arg Glu Gln Met Gln Glu Leu Val Asp
            435                 440                 445

Asn Met Lys Cys Ile Leu Val Asp Ala Gly Lys Asn Val Ala Asp Glu
            450                 455                 460

Thr Glu Ser
465

<210> SEQ ID NO 113
<211> LENGTH: 223
<212> TYPE: PRT
<213> ORGANISM: Gossypium hirsutum

<400> SEQUENCE: 113

Met Gly Arg Gly Lys Ile Glu Ile Lys Arg Ile Glu Asn Thr Thr Asn
1               5                   10                  15

Arg Gln Val Thr Phe Cys Lys Arg Arg Asn Gly Leu Leu Lys Lys Ala
            20                  25                  30

Tyr Glu Leu Ser Val Leu Cys Asp Ala Glu Val Ala Leu Ile Val Phe
            35                  40                  45

Ser Ser Arg Gly Arg Leu Tyr Glu Tyr Ser Asn Asn Asn Ile Arg Ser
    50                  55                  60

Thr Ile Asp Arg Tyr Lys Lys Ala Cys Ser Asp Thr Ser Asn Thr Asn
65                  70                  75                  80

Thr Val Thr Glu Ile Asn Ala Gln Tyr Tyr Gln Gln Glu Ser Ala Lys
                85                  90                  95

Leu Arg Gln Gln Ile Gln Met Leu Gln Asn Ser Asn Arg His Leu Met
            100                 105                 110

Gly Asp Ser Leu Ser Ser Leu Thr Val Lys Glu Leu Lys Gln Val Glu

```
                 115                 120                 125
Asn Arg Leu Glu Arg Gly Ile Thr Arg Ile Arg Ser Lys Lys His Glu
    130                 135                 140

Met Leu Leu Ala Glu Ile Glu Phe Leu Gln Lys Arg Glu Ile Glu Leu
145                 150                 155                 160

Glu Asn Glu Ser Val Cys Leu Arg Thr Lys Ile Ala Glu Ile Glu Arg
                165                 170                 175

Leu Gln Gln Ala Asn Met Val Thr Gly Pro Glu Leu Asn Ala Ile Gln
            180                 185                 190

Ala Leu Ala Ser Arg Asn Phe Phe Ser Pro Asn Val Ile Glu His Pro
        195                 200                 205

Ser Ala Tyr Ser His Leu Ser Asp Lys Lys Ile Leu His Leu Gly
    210                 215                 220

<210> SEQ ID NO 114
<211> LENGTH: 310
<212> TYPE: PRT
<213> ORGANISM: Gossypium hirsutum

<400> SEQUENCE: 114

Met Asp Val Thr Ser Thr Pro Asn Arg Lys Glu Met Asp Arg Ile Lys
1               5                   10                  15

Gly Pro Trp Ser Pro Glu Glu Asp Asp Leu Leu Gln Gln Leu Val Gln
                20                  25                  30

Lys His Gly Pro Arg Asn Trp Ser Leu Ile Ser Lys Ser Ile Pro Gly
            35                  40                  45

Arg Ser Gly Lys Ser Cys Arg Leu Arg Trp Cys Asn Gln Leu Ser Pro
        50                  55                  60

Gln Val Glu His Arg Ala Phe Thr Pro Glu Glu Asp Glu Thr Ile Ile
65                  70                  75                  80

Arg Ala His Ala Arg Phe Gly Asn Lys Trp Ala Thr Ile Ala Arg Leu
                85                  90                  95

Leu Asn Gly Arg Thr Asp Asn Ala Ile Lys Asn His Trp Asn Ser Thr
            100                 105                 110

Leu Lys Arg Lys Cys Leu Pro Val Gly Glu Glu Cys Asn Phe Val Ala
        115                 120                 125

Asn Gly Gly Tyr Asp Gly Asn Leu Gly Gly Glu Arg Gln Pro Leu
    130                 135                 140

Lys Arg Ser Val Ser Ala Gly Leu Tyr Met Ser Pro Gly Ser Pro Ser
145                 150                 155                 160

Gly Ser Asp Val Ser Asp Ser Ser Val Pro Val Leu Ser Ser Ser Tyr
                165                 170                 175

Val Tyr Lys Pro Ile Pro Arg Thr Gly Gly Val Asn Val Asp Val Asn
            180                 185                 190

Val Thr Pro Ala Gly Val Glu Ala Ala Ser Ser Ser Asn Asp Pro Pro
        195                 200                 205

Thr Ser Leu Ser Leu Ser Leu Pro Gly Val Glu Ser Cys Glu Val Val
    210                 215                 220

Ser Thr Gln Pro Ile Thr Glu Ser Thr Gln Asn Arg Ser Glu Glu Arg
225                 230                 235                 240

Gly Gly Gly Val Met Gly Phe Ser Ala Glu Phe Met Ala Val Met Gln
                245                 250                 255

Glu Met Ile Arg Val Glu Val Arg Asn Tyr Met Thr Gln Met Gln Gln
            260                 265                 270
```

```
Gln Gln Gln Gln Gln Asn Gly Ala Val Pro Gly Gly Ala Gly Met Gly
            275                 280                 285

Met Cys Leu Asp Gly Gly Phe Arg Asn Leu Met Ala Val Asn Pro Val
            290                 295                 300

Gly Met Ser Lys Ile Glu
305                 310

<210> SEQ ID NO 115
<211> LENGTH: 593
<212> TYPE: PRT
<213> ORGANISM: Gossypium hirsutum

<400> SEQUENCE: 115

Met Gly Gly Pro Pro Tyr Asp Cys Leu Ala Asn Pro Leu Gly Ala Val
1               5                   10                  15

Arg Leu Thr Phe Glu Lys Ala Ile Trp Ser Glu Ser Glu Thr Pro Pro
            20                  25                  30

Ile His Pro Ser Ala Phe Asn Gly Lys Asp Trp Gly Ala Leu Glu Leu
            35                  40                  45

Phe Arg His Phe Leu Phe Gln Gly Ser Gly Leu Ser Gln Val Pro Ile
    50                  55                  60

Leu Asn Pro Lys Thr Leu Arg Trp Val Gln Pro Asn Ser Leu Val Arg
65                  70                  75                  80

Tyr Arg Gly Met Ile Gln Asp Met Leu Gly Asn Glu Phe Tyr Ala Gly
                85                  90                  95

Ala Tyr Lys Asp Gly Asn Leu Trp Arg Thr Asn Lys Phe Met Asp Val
            100                 105                 110

Ser Gln Tyr Pro Met Gly Ser Ser Pro Asp Met Cys Ile Trp Glu Arg
            115                 120                 125

Arg Leu Leu Tyr Cys Val Pro Val Pro Gly Gln Asn Ser Trp Thr Glu
    130                 135                 140

Pro Ser Ser Glu Met Glu Pro Asn Trp Ser Ser Gln Thr Arg Glu Lys
145                 150                 155                 160

Arg Arg Arg Met Asp Asp Glu Asp Asn Asp Pro Met Asp Leu Val Pro
                165                 170                 175

Asp Asp Glu Ile Lys Ser Ser Pro Ile Thr Lys Lys Met Arg Glu Asp
            180                 185                 190

Gly Leu Pro Ser Pro Ser Gln Ser Arg Asp Thr Lys Thr Thr Ser Ser
            195                 200                 205

Ser Ser Ile Thr Ser Thr Phe Gln Ser Val Asp Glu Asp Asn Leu Pro
    210                 215                 220

Cys Leu Val Lys Ile Tyr Asp Ser Pro Glu Ser Glu Leu Lys Leu Asn
225                 230                 235                 240

Asp Val Phe Glu Phe Ile Gly Val Leu Thr Phe Asp Ser Glu Leu Ala
                245                 250                 255

Val Glu Lys Asp Asp Asn Asp Glu Leu Ser Asn Ser Phe Tyr Asp Asp
            260                 265                 270

Ala Leu Val His Leu Pro Pro Asn Lys Val Pro Arg Leu His Cys Leu
            275                 280                 285

Ile His Arg Lys Leu Ala Val Gln Asp Phe Leu Pro Gly Ser Pro Ile
    290                 295                 300

Ile Glu Pro Lys Pro His Leu Val Lys Glu Thr Arg Glu Ala Leu Phe
305                 310                 315                 320

Arg His Leu Thr Ala Val Leu Gly Asn Asp Glu Val Ala Ala His Phe
                325                 330                 335
```

```
Val Leu Leu His Leu Leu Ser Lys Val His Ala Arg Val Asp Asp Val
            340                 345                 350
Ala Val Gly Lys Leu Ser Leu Asn Leu Thr Gly Leu Asn Lys Glu Ser
            355                 360                 365
Val Ser Val Phe Gly Thr Arg Leu Ser Asp Thr Phe Lys Asn Leu Leu
            370                 375                 380
Pro Phe Thr Asn Cys Met Pro Leu Thr Leu Glu Tyr Leu Asn Ile Ala
385                 390                 395                 400
Ser Leu Ala Pro Gln Lys Asp Tyr Gln Ala Asn Arg Leu Val Pro Gly
            405                 410                 415
Val Leu Gln Leu Pro Glu Gly Ser His Leu Met Val Asp Glu Thr Arg
            420                 425                 430
Leu Glu Ser Gly Ser Leu Asn Ser Thr Gly Ile Glu Asn Thr Lys Leu
            435                 440                 445
Leu Lys Asn Leu Ile Glu Phe Gln Lys Val Glu Tyr Asp Phe Gln Tyr
            450                 455                 460
Tyr Lys Val Glu Met Ala Thr Asp Val Gln Leu Leu Ile Phe Ser Glu
465                 470                 475                 480
Gly Lys Ser Asn Ile Val Pro Ala Asp Val Ile Val Pro Phe Gln Pro
            485                 490                 495
Ser Cys Leu Glu Ser Thr Glu Met Pro Val Ala Glu Ala Leu Glu Ala
            500                 505                 510
Trp Arg Trp Tyr Leu Ala Thr Val Arg Ser Leu Pro His Ser Ile Gly
            515                 520                 525
Ser Glu Ile Gln Lys Val Val Glu Asp Asp Leu Val Ala Ala Arg Gln
            530                 535                 540
Met Asp Arg Ser Leu Gly Ser Arg Asp Phe Ser Arg Trp Leu Thr Met
545                 550                 555                 560
Ala Arg Leu Ile Ser Ser Ser Phe Gly Glu Thr Ser Leu Ser Lys Glu
            565                 570                 575
His Trp Glu Met Ala Lys Glu Met Glu Arg Leu Arg Arg Glu Arg Leu
            580                 585                 590
Lys

<210> SEQ ID NO 116
<211> LENGTH: 89
<212> TYPE: PRT
<213> ORGANISM: Gossypium hirsutum
<220> FEATURE:
<221> NAME/KEY: misc_feature
<222> LOCATION: (48)..(48)
<223> OTHER INFORMATION: Xaa can be any naturally occurring amino acid

<400> SEQUENCE: 116

Met Ser Met Lys Lys Glu Gly Glu Ile Leu Tyr Lys Lys Gly Leu Trp
1               5                   10                  15
Ala Met Glu Glu Asp Lys Leu Leu Ile Asp Tyr Val Asn Val His Gly
            20                  25                  30
Lys Gly Gln Trp Asn Lys Ile Ala Asn Arg Thr Gly Leu Lys Arg Xaa
            35                  40                  45
Gly Lys Ser Cys Arg Leu Arg Trp Met Asn Tyr Leu Ser Pro Asn Val
            50                  55                  60
Lys Lys Gly Asp Phe Ser Glu Glu Glu Asp Leu Val Ile Arg Leu
65                  70                  75                  80
His Lys Leu Leu Glu Thr Gly Gly Leu
```

<210> SEQ ID NO 117
<211> LENGTH: 628
<212> TYPE: PRT
<213> ORGANISM: Gossypium hirsutum

<400> SEQUENCE: 117

```
Met Ser Thr Gly Val Gln His Gln Glu Arg Val Pro Met Asn Leu Lys
1               5                   10                  15

Lys Gln Leu Ala Leu Ala Val Arg Asn Ile Gln Trp Ser Tyr Ala Ile
            20                  25                  30

Phe Trp Ser Ile Ser Thr Arg Gln Pro Gly Val Leu Glu Trp Gly Glu
        35                  40                  45

Gly Tyr Tyr Asn Gly Asp Ile Lys Thr Arg Lys Thr Val Gln Ser Val
    50                  55                  60

Glu Leu Asn Thr Asp Gln Leu Ser Leu Gln Arg Ser Glu Gln Leu Arg
65                  70                  75                  80

Gln Leu Tyr Glu Ser Leu Ser Ala Gly Glu Ser Ser Pro Gln Ala Lys
                85                  90                  95

Arg Pro Ser Ala Ala Leu Ser Pro Glu Asp Leu Thr Asp Thr Glu Trp
            100                 105                 110

Tyr Tyr Leu Val Cys Met Ser Phe Val Phe Asn Ile Gly Gln Gly Leu
        115                 120                 125

Pro Gly Arg Thr Leu Ser Thr Gly Gln Pro Val Trp Leu Cys Asn Ala
    130                 135                 140

His Cys Ala Asp Ser Lys Val Phe Gly Arg Ser Leu Leu Ala Lys Ser
145                 150                 155                 160

Ala Ser Ile Gln Thr Ala Val Cys Phe Pro Phe Ser Gly Gly Val Val
                165                 170                 175

Glu Leu Gly Val Thr Asp Leu Val Phe Glu Asp Leu Ser Leu Ile Gln
            180                 185                 190

Arg Val Lys Thr Leu Leu Leu Asp Asp Pro Gln Pro Ile Val Ser Lys
        195                 200                 205

Arg Ser Ile Gln Val Asp Gly Met Asn Asn Asp Leu Ala Cys Pro Ala
    210                 215                 220

Leu Asp Pro Leu Ile Leu Ala Thr Lys Leu Ser Pro Ile Leu Gly Cys
225                 230                 235                 240

Glu Gln Leu Glu Thr Val Ser Pro Asp Ser Pro Asp Gly Leu Glu
                245                 250                 255

Pro Lys Gln Ser Arg Glu Asp Ser Leu Leu Ile Glu Gly Ile Asn Gly
            260                 265                 270

Gly Ala Ser Gln Val Gln Ser Trp Gln Phe Met Asp Glu Glu Phe Cys
        275                 280                 285

Asn Cys Val His His Ser Leu Asn Ser Ser Asp Cys Ile Ser Gln Thr
    290                 295                 300

Ile Ala Asp His Arg Lys Val Val Pro Leu Tyr Arg Gly Glu Asn Asp
305                 310                 315                 320

Asn Gly Leu Gln Asp Val Glu Glu Cys Asn Gln Thr Lys Leu Thr Ser
                325                 330                 335

Phe Asp Arg Gln Asn Asp Asp Arg His Phe His Glu Val Leu Ser Ala
            340                 345                 350

Leu Phe Lys Ser Ser His Pro Leu Ile Leu Gly Pro Gln Phe Arg Asn
        355                 360                 365
```

```
Ser Asn Lys Glu Ser Ser Phe Ile Arg Trp Gln Lys Asn Gly Leu Val
    370                 375                 380

Lys Pro Gln Lys Glu Arg Asp Glu Thr Pro Gln Lys Leu Leu Lys Lys
385                 390                 395                 400

Ile Leu Phe Leu Val Pro His Met His Asp Arg Gly Leu Ile Glu Ser
                405                 410                 415

Pro Glu Thr Asn Ala Val Arg Asp Ala Ala Trp Arg Pro Glu Ala Asp
            420                 425                 430

Glu Ile Cys Gly Asn His Val Leu Ser Glu Arg Lys Arg Glu Lys
        435                 440                 445

Ile Asn Glu Arg Leu Met Met Leu Lys Ser Leu Val Pro Ala Asn Asn
    450                 455                 460

Lys Ala Asp Lys Val Ser Ile Leu Asp Val Thr Ile Glu Tyr Leu Gln
465                 470                 475                 480

Thr Leu Glu Arg Val Ala Glu Leu Glu Ser Cys Arg Lys Ser Glu
                485                 490                 495

Ala Arg Thr Lys Ile Glu Arg Thr Ser Asp Asn Tyr Gly Asn Asn Lys
            500                 505                 510

Thr Asn Asn Gly Lys Lys Ser Ser Leu Ser Lys Arg Lys Ala Tyr Asp
        515                 520                 525

Val Val Asp Glu Ala Asp Gln Glu Ile Gly Tyr Val Ala Ser Lys Asp
    530                 535                 540

Gly Ser Thr Asp Lys Val Thr Leu Ser Met Asn Asn Lys Glu Leu Leu
545                 550                 555                 560

Ile Glu Phe Lys Cys Pro Trp Arg Glu Gly Ile Leu Leu Glu Val Met
                565                 570                 575

Asp Ala Leu Ser Ile Leu Asn Leu Asp Cys His Ser Val Gln Ser Ser
            580                 585                 590

Thr Thr Glu Gly Ile Leu Ser Leu Thr Ile Lys Ser Lys Tyr Lys Gly
        595                 600                 605

Ser Ser Val Ala Lys Ala Gly Pro Ile Glu Gln Ala Leu Gln Arg Ile
    610                 615                 620

Ala Ser Lys Cys
625

<210> SEQ ID NO 118
<211> LENGTH: 123
<212> TYPE: PRT
<213> ORGANISM: Gossypium hirsutum

<400> SEQUENCE: 118

Met Ala Ser Ser Gly Val Leu Lys Leu Val Ser Met Ile Leu Met Val
1               5                   10                  15

Cys Met Thr Met Met Ser Ala Pro Lys Ala Lys Ala Ala Ile Thr
                20                  25                  30

Cys Ser Asp Val Val Asn His Leu Ile Pro Cys Leu Ser Tyr Val Gln
            35                  40                  45

Asn Gly Gly Thr Pro Ala Ala Ala Cys Cys Ser Gly Val Lys Ala Leu
        50                  55                  60

Tyr Gly Glu Val Gln Thr Ser Pro Asp Arg Gln Asn Val Cys Lys Cys
65                  70                  75                  80

Ile Lys Ser Ala Val Asn Gly Ile Pro Tyr Thr Ser Asn Asn Leu Asn
                85                  90                  95

Leu Ala Ala Gly Leu Pro Ala Lys Cys Gly Leu Gln Leu Pro Tyr Ser
            100                 105                 110
```

```
Ile Ser Pro Ser Thr Asp Cys Asn Lys Val Gln
        115                 120
```

<210> SEQ ID NO 119
<211> LENGTH: 362
<212> TYPE: PRT
<213> ORGANISM: Gossypium hirsutum

<400> SEQUENCE: 119

```
Met Ala Asn His Thr Val Thr Phe Leu Pro Lys Leu Ser Ile Glu Ala
1               5                   10                  15

Ile Gln Thr Val Thr Pro Met Arg Ile Thr Glu Pro Arg Gln Thr Arg
            20                  25                  30

Gln Val Leu Ala Gly Glu Leu Val Gly Pro Gly Ile Phe Gln Arg Cys
        35                  40                  45

Leu Asn Val Val Gln Tyr Tyr Met Lys Glu Lys Glu Asp Ser Gly
    50                  55                  60

Trp Leu Leu Ala Gly Trp Ile Lys Glu Thr Leu Gly Arg Ala Leu His
65                  70                  75                  80

Glu Gln Pro Met Ile Ser Gly Arg Leu Arg Lys Gly Glu Arg Asn Asp
                85                  90                  95

Gly Glu Leu Glu Ile Val Ser Asn Asp Cys Gly Ile Arg Leu Ile Glu
            100                 105                 110

Ala Arg Ile Gln Met Asn Leu Ser Asp Phe Leu Asp Leu Lys Gln Arg
        115                 120                 125

Glu Asp Ala Glu Ala Gln Leu Val Phe Trp Lys Asp Ile Asp Glu Gln
130                 135                 140

Asn Pro Gln Phe Ser Pro Leu Phe Tyr Val Gln Val Thr Asn Phe Gln
145                 150                 155                 160

Cys Gly Gly Tyr Ser Ile Gly Ile Ser Cys Ser Ile Leu Leu Ala Asp
                165                 170                 175

Leu Leu Leu Met Lys Glu Phe Leu Lys Thr Trp Ala Asp Ile His Asn
            180                 185                 190

Lys Val Ile Ile Asn Lys Asn Asp Glu Gln Lys Leu Pro Leu Phe Tyr
        195                 200                 205

Leu Pro Gly Leu Lys Asn Thr Asn Gly Ala Ser Pro Asn Ile Ile Thr
    210                 215                 220

Ser Asn Ser Ser Lys Asn Ser Ala Lys Thr Met Ile Phe Gln Ile Gln
225                 230                 235                 240

Ala Glu Thr Glu Ser Pro Gly Ser Asp Trp Cys Arg Lys Met Ala Leu
                245                 250                 255

Ala Cys Leu Glu Glu Ala Glu Ser Asn Leu Gly Ser Val Val Gly Gly
            260                 265                 270

Glu Phe Ser Leu Phe Val Asn Glu Ser Phe Glu Ser Ile Lys Val Glu
        275                 280                 285

Ser Cys Ser Lys Gln Gly Met Ser Lys Glu Ala Glu Met Gly Val Leu
    290                 295                 300

Asn Arg Ala Lys Trp Asp Leu Gly Ala Asn Glu Val Ser Phe Gly
305                 310                 315                 320

Asp Gly Asn Lys Pro Ala His Val Ser Tyr Trp Leu Arg Ser Thr Leu
                325                 330                 335

Gly Gly Leu Ile Ile Val Ile Pro Ser Leu Gln Glu Asp Lys Tyr Thr
            340                 345                 350

Val Asn Ile Ile Val Thr Ile Pro Ser Lys
```

<210> SEQ ID NO 120
<211> LENGTH: 497
<212> TYPE: PRT
<213> ORGANISM: Gossypium hirsutum

<400> SEQUENCE: 120

```
Met Gly Phe Gln Arg Asn Ile Leu Gly Phe Leu Leu Ile Leu Ala
1               5                   10                  15

Ser Leu Thr Ser Leu Ser Ser Leu Pro Ser Glu Tyr Ser Ile Val
            20                  25                  30

Glu His Glu Ile Asp Ala Phe Leu Ser Glu Arg Val Leu Glu Ile
            35                  40                  45

Phe Gln Gln Trp Lys Glu Lys Asn Gln Lys Val Tyr Arg Gln Ala Glu
    50                  55                  60

Glu Ala Glu Lys Arg Phe Glu Asn Phe Lys Gly Asn Leu Lys Tyr Ile
65                  70                  75                  80

Leu Glu Arg Asn Ala Lys Arg Lys Ala Asn Lys Trp Glu His His Val
                85                  90                  95

Gly Leu Asn Lys Phe Ala Asp Met Ser Asn Glu Glu Phe Arg Lys Ala
            100                 105                 110

Tyr Leu Ser Lys Val Lys Lys Pro Ile Asn Lys Gly Ile Thr Leu Ser
            115                 120                 125

Arg Asn Met Arg Arg Lys Val Gln Ser Cys Asp Ala Pro Ser Ser Leu
        130                 135                 140

Asn Trp Arg Asn Tyr Gly Val Thr Ala Val Lys Asp Gln Gly Ser
145                 150                 155                 160

Cys Gly Ser Cys Trp Ala Phe Ser Ser Thr Gly Ala Met Glu Gly Ile
                165                 170                 175

Asn Ala Leu Val Thr Gly Asp Leu Ile Ser Leu Ser Glu Gln Glu Leu
            180                 185                 190

Val Asp Cys Asp Thr Ser Asn Tyr Gly Cys Glu Gly Gly Tyr Met Asp
        195                 200                 205

Tyr Ala Phe Glu Trp Val Ile Asn Asn Gly Gly Ile Asp Ser Glu Thr
    210                 215                 220

Asp Tyr Pro Tyr Thr Gly Val Asp Gly Thr Cys Asn Thr Thr Lys Glu
225                 230                 235                 240

Glu Thr Lys Val Val Ser Ile Asp Gly Tyr Gln Asp Val Glu Gln Ser
                245                 250                 255

Asp Ser Ala Leu Leu Cys Ala Val Ala Gln Gln Pro Val Ser Val Gly
            260                 265                 270

Ile Asp Gly Ser Ala Ile Asp Phe Gln Leu Tyr Thr Gly Gly Ile Tyr
        275                 280                 285

Asp Gly Ser Cys Ser Asp Asp Pro Asp Ile Asp His Ala Val Leu
    290                 295                 300

Ile Val Gly Tyr Gly Ser Glu Gly Ser Glu Glu Tyr Trp Ile Val Lys
305                 310                 315                 320

Asn Ser Trp Gly Thr Ser Trp Gly Ile Asp Gly Tyr Phe Tyr Leu Lys
                325                 330                 335

Arg Asp Thr Asp Leu Pro Tyr Gly Val Cys Ala Val Asn Ala Met Ala
            340                 345                 350
```

```
Ser Tyr Pro Thr Lys Glu Ser Ser Pro Ser Pro Tyr Pro Ser Pro
        355                 360                 365

Ser Val Pro Pro Pro Pro Ser Thr Pro Pro Pro Pro Pro
    370             375             380

Pro Ser Pro Ser Pro Ser Asp Cys Gly Asp Phe Ser Tyr Cys Ser Ser
385                 390                 395                 400

Asp Glu Thr Cys Cys Cys Leu Phe Glu Phe Tyr Asp Tyr Cys Leu Ile
                405                 410                 415

Tyr Gly Cys Cys Glu Tyr Glu Asn Ala Val Cys Cys Thr Gly Thr Glu
            420                 425                 430

Tyr Cys Cys Pro Ser Asp Tyr Pro Ile Cys Asp Val Gln Glu Gly Leu
            435                 440                 445

Cys Leu Lys Asn Ala Gly Asp Tyr Leu Gly Val Ala Ala Arg Lys Arg
        450                 455                 460

Lys Val Ala Lys His Lys Leu Pro Trp Thr Lys Ile Glu Glu Thr Glu
465                 470                 475                 480

Ile Thr Tyr Gln Pro Leu Gln Trp Lys Arg Asn Pro Phe Ala Ala Met
                485                 490                 495

Arg

<210> SEQ ID NO 121
<211> LENGTH: 335
<212> TYPE: PRT
<213> ORGANISM: Gossypium hirsutum

<400> SEQUENCE: 121

Met Lys Val Leu Ser Pro Ile Leu Ala Cys Leu Ala Leu Ala Val Val
1               5                   10                  15

Val Ser His Ala Ala Leu Ser Pro Glu Gln Tyr Trp Ser Tyr Lys Leu
            20                  25                  30

Pro Asn Thr Pro Met Pro Lys Ala Val Lys Glu Ile Leu His Pro Glu
        35                  40                  45

Leu Met Glu Glu Lys Ser Thr Ser Val Asn Val Gly Gly Gly Gly Val
    50                  55                  60

Asn Val Asn Thr Gly Lys Gly Lys Pro Gly Gly Asp Thr His Val Asn
65                  70                  75                  80

Val Gly Gly Lys Gly Val Gly Val Asn Thr Gly Lys Pro Gly Gly Gly
                85                  90                  95

Thr His Val Asn Val Gly Asp Pro Phe Asn Tyr Leu Tyr Ala Ala Ser
            100                 105                 110

Glu Thr Gln Ile His Glu Asp Pro Asn Val Ala Leu Phe Phe Leu Glu
        115                 120                 125

Lys Asp Met His Pro Gly Ala Thr Met Ser Leu His Phe Thr Glu Asn
    130                 135                 140

Thr Glu Lys Ser Ala Phe Leu Pro Tyr Gln Thr Ala Gln Lys Ile Pro
145                 150                 155                 160

Phe Ser Ser Asp Lys Leu Pro Glu Ile Phe Asn Lys Phe Ser Val Lys
                165                 170                 175

Pro Gly Ser Val Lys Ala Glu Met Met Lys Asn Thr Ile Lys Glu Cys
            180                 185                 190

Glu Gln Pro Ala Ile Glu Gly Glu Glu Lys Tyr Cys Ala Thr Ser Leu
        195                 200                 205
```

```
Glu Ser Met Ile Asp Tyr Ser Ile Ser Lys Leu Gly Lys Val Asp Gln
210                 215                 220
Ala Val Ser Thr Glu Val Glu Lys Gln Thr Pro Met Gln Lys Tyr Thr
225                 230                 235                 240
Ile Ala Ala Gly Val Gln Lys Met Thr Asp Asp Lys Ala Val Val Cys
                245                 250                 255
His Lys Gln Asn Tyr Ala Tyr Ala Val Phe Tyr Cys His Lys Ser Glu
            260                 265                 270
Thr Thr Arg Ala Tyr Met Val Pro Leu Glu Gly Ala Asp Gly Thr Lys
        275                 280                 285
Ala Lys Ala Val Ala Val Cys His Thr Asp Thr Ser Ala Trp Asn Pro
290                 295                 300
Lys His Leu Ala Phe Gln Val Leu Lys Val Glu Pro Gly Thr Ile Pro
305                 310                 315                 320
Val Cys His Phe Leu Pro Arg Asp His Ile Val Trp Val Pro Lys
                325                 330                 335

<210> SEQ ID NO 122
<211> LENGTH: 302
<212> TYPE: PRT
<213> ORGANISM: Gossypium hirsutum

<400> SEQUENCE: 122

Met Glu Arg Gln Arg Ser Lys Gln Val Cys Leu Leu Met Trp Val Leu
1               5                   10                  15
Val Ala Ala Phe Phe Ser His Asn Arg Val Ile Ala Val Thr Ser Thr
                20                  25                  30
Gly Leu Gly Glu Gln Lys Asn Tyr Tyr Pro Ala Pro Asp Pro His Ala
            35                  40                  45
Gly Thr Pro Pro Ser Gly Ser His Gly Thr Pro Pro Ser Ser Gly Gly
        50                  55                  60
Gly Ser Pro Pro Ser His Gly Thr Pro Ser His Gly Gly Gly Tyr His
65                  70                  75                  80
Pro Ser Pro Thr Pro Ser Thr Pro Ser Gly Gly Asn Cys Gly Thr Pro
                85                  90                  95
Pro His Asp Pro Ser Thr Pro Ser Thr Pro Ser His Thr Pro Pro His
            100                 105                 110
Gly Thr Pro Pro Ser Ser Gly Gly Gly Ser Pro Pro Ser Tyr Gly Gly
        115                 120                 125
Gly Ser Pro Pro Ser Tyr Gly Gly Gly Ser Pro Pro Ser Tyr Gly Gly
    130                 135                 140
Gly Ser Pro Pro Ser Tyr Gly Gly Gly Ser Pro Pro Ser Tyr Gly Gly
145                 150                 155                 160
Gly Ser Pro Pro Thr Thr Pro Ile Asp Pro Gly Thr Pro Ser Ile Pro
                165                 170                 175
Ser Pro Pro Phe Phe Pro Ala Pro Thr Pro Pro Ile Gly Gly Thr Cys
            180                 185                 190
Asp Phe Trp Arg Ser His Pro Thr Leu Ile Trp Gly Leu Leu Gly Trp
        195                 200                 205
Trp Gly Thr Val Gly Asn Ala Phe Gly Val Thr Asn Ala Pro Gly Leu
210                 215                 220
Gly Thr Ser Met Ser Leu Pro Gln Ala Leu Ser Asn Thr Arg Thr Asp
225                 230                 235                 240
Gly Leu Gly Ala Leu Tyr Arg Glu Gly Thr Ala Ser Phe Leu Asn Ser
                245                 250                 255
```

Met Val Asn Asn Arg Phe Pro Phe Ser Thr Lys Gln Val Arg Glu Thr
            260                 265                 270

Phe Val Ala Ala Leu Gly Ser Asn Ser Ala Ala Ala Gln Ala Arg
            275                 280                 285

Leu Phe Lys Leu Ala Asn Glu Gly His Leu Lys Pro Arg Thr
            290                 295                 300

<210> SEQ ID NO 123
<211> LENGTH: 196
<212> TYPE: PRT
<213> ORGANISM: Gossypium hirsutum

<400> SEQUENCE: 123

Met Met Lys Arg Gly Phe Ile Val Leu Ala Leu Thr Val Val Phe Ala
1               5                   10                  15

Ala Thr Val Val Thr Ala Ala Asp Glu Ser Gly Leu Ala Asn Glu Cys
            20                  25                  30

Ser Lys Asp Phe Gln Ser Val Met Thr Cys Leu Ser Phe Ala Gln Gly
        35                  40                  45

Lys Ala Ala Ser Pro Ser Lys Glu Cys Cys Asn Ser Val Ala Gly Ile
    50                  55                  60

Lys Glu Asn Lys Pro Lys Cys Leu Cys Tyr Ile Leu Gln Gln Thr Gln
65                  70                  75                  80

Thr Ser Gly Ala Gln Asn Leu Lys Ser Leu Gly Val Gln Glu Asp Lys
                85                  90                  95

Leu Phe Gln Leu Pro Ser Ala Cys Gln Leu Lys Asn Ala Ser Val Ser
            100                 105                 110

Asp Cys Pro Lys Leu Leu Gly Leu Ser Pro Ser Ser Pro Asp Ala Ala
        115                 120                 125

Ile Phe Thr Asn Ser Ser Ser Lys Ala Thr Thr Pro Ser Thr Ser Thr
    130                 135                 140

Thr Thr Ala Thr Pro Ser Ser Ala Ala Asp Lys Thr Asp Ser Lys Ser
145                 150                 155                 160

Ser Gly Ile Lys Leu Gly Pro His Phe Val Gly Ser Thr Ala Ala Leu
                165                 170                 175

Leu Val Ala Thr Ala Ala Val Phe Phe Leu Val Phe Pro Ala Gly Phe
            180                 185                 190

Ala Ser Ile Val
        195

<210> SEQ ID NO 124
<211> LENGTH: 629
<212> TYPE: PRT
<213> ORGANISM: Gossypium hirsutum

<400> SEQUENCE: 124

Met Pro Val Val Asp Phe Ala Cys Val Phe Leu Val Ser Val Val Met
1               5                   10                  15

Phe Asn Leu Arg Val Ser Thr Glu Pro Val Glu Asp Lys Gln Ala Leu
            20                  25                  30

Leu Ala Phe Ile Ser Gly Ile Arg His Ala Asp Arg Val Lys Trp Asn
        35                  40                  45

Ser Ser Thr Ser Ala Cys Asp Trp Phe Gly Val Gln Cys Asp Ala Asn
    50                  55                  60

Arg Ser Phe Val Tyr Thr Leu Arg Val Pro Gly Trp Gly Pro Tyr Gly
65                  70                  75                  80

```
Val Arg Phe Arg Pro Lys Gln Ile Gly Arg Leu Asn Arg Leu Arg Val
                85                  90                  95

Leu Ser Leu Arg Ala Asn Arg Leu Ser Gly Glu Ile Pro Ala Asp Phe
            100                 105                 110

Tyr Asn Leu Thr Gln Leu Arg Ser Leu Tyr Leu Gln Gly Asn Glu Phe
            115                 120                 125

Thr Gly Pro Phe Pro Ser Val Thr Arg Leu Thr Arg Leu Thr Arg
            130                 135                 140

Leu Asp Leu Ser Ser Asn Asn Phe Thr Gly Pro Ile Pro Leu Gly Val
145                 150                 155                 160

Asn Asn Leu Thr Gln Leu Thr Lys Leu Phe Leu Gln Asn Asn Lys Phe
                165                 170                 175

Ser Gly Ser Leu Pro Ser Ile Asp Ser Asp Gly Leu Asn Asp Phe Asn
            180                 185                 190

Val Ser Asn Asn Leu Lys Gly Ser Ile Pro Asp Ser Leu Ser Lys
                195                 200                 205

Phe Pro Glu Ser Ser Phe Ala Gly Asn Ile Gly Leu Cys Gly Gly Pro
    210                 215                 220

Leu Arg Pro Cys Asn Pro Phe Pro Pro Ser Pro Ser Pro Thr Glu Pro
225                 230                 235                 240

Ile Pro Pro Lys Thr Ser Gly Gln Ser Ser Lys Ser Leu Pro Thr Gly
                245                 250                 255

Ala Ile Ile Ala Ile Ala Val Gly Ser Ala Ile Val Ala Leu Leu Leu
            260                 265                 270

Leu Leu Phe Leu Ile Ile Cys Phe Arg Lys Trp Lys Arg Lys Ser Pro
            275                 280                 285

Arg Arg Gln Lys Ala Ile Pro Ser Thr Thr His Ala Leu Pro Val Glu
    290                 295                 300

Glu Ala Gly Thr Ser Ser Ser Lys Asp Asp Ile Thr Gly Gly Ser Thr
305                 310                 315                 320

Glu Ile Glu Arg Met Met Asn Asn Lys Leu Met Phe Phe Lys Gly Gly
                325                 330                 335

Val Tyr Ser Phe Asp Leu Glu Asp Leu Met Arg Ala Ser Ala Glu Met
            340                 345                 350

Leu Gly Lys Gly Ser Thr Gly Thr Ser Tyr Arg Val Val Leu Ala Val
            355                 360                 365

Gly Thr Thr Val Ala Val Lys Arg Leu Lys Asp Val Ala Val Ser Lys
    370                 375                 380

Arg Glu Phe Val Met Lys Met Gly Met Leu Gly Lys Ile Met His Glu
385                 390                 395                 400

Asn Val Val Pro Leu Arg Ala Phe Tyr Tyr Ser Asp Glu Glu Lys Leu
                405                 410                 415

Leu Val Tyr Asp Tyr Met His Gly Gly Ser Leu Phe Ala Leu Leu His
            420                 425                 430

Gly Ser Arg Ser Ser Ala Arg Thr Pro Leu Glu Trp Asp Pro Arg Met
            435                 440                 445

Lys Ile Ala Leu Gly Val Ala Arg Gly Leu Ala His Leu His Ser Ser
    450                 455                 460

Gln Asn Met Val His Gly Asn Ile Lys Ser Ser Asn Ile Leu Leu Arg
465                 470                 475                 480

Pro Asp His Glu Ala Cys Ile Ser Glu Phe Gly Leu Asn Ser Leu Phe
                485                 490                 495
```

```
Asn Thr Asn Thr Pro Pro Ser Arg Ile Ala Gly Tyr Gln Ala Pro Glu
            500                 505                 510

Val Ile Gln Thr His Lys Val Thr Val Lys Ser Asp Val Tyr Ser Phe
        515                 520                 525

Gly Val Leu Leu Glu Leu Leu Thr Gly Arg Ala Pro Ile Gln Pro
    530                 535                 540

Ser Ile Thr Glu Glu Gly Phe Asp Leu Pro Arg Trp Val Gln Ser Val
545                 550                 555                 560

Val Arg Glu Glu Trp Ala Ala Glu Val Phe Asp Ala Glu Leu Met Ala
                565                 570                 575

Tyr His Asp Ile Glu Glu Met Val Gln Ala Leu Gln Met Ala Met
            580                 585                 590

Val Cys Val Ser Thr Val Pro Asp Gln Arg Pro Val Met Ser Glu Val
        595                 600                 605

Val Arg Met Ile Gly Asp Met Ile Asp Arg Gly Gly Thr Asn Asp Gly
    610                 615                 620

Thr Ala Ala Ala Ile
625

<210> SEQ ID NO 125
<211> LENGTH: 545
<212> TYPE: PRT
<213> ORGANISM: Gossypium hirsutum

<400> SEQUENCE: 125

Met Ala Glu Met Ser Thr Leu Cys Thr Phe Leu Phe Ser Leu Leu Leu
1               5                   10                  15

Phe Ala Ser His Pro Leu Ile Leu Pro Thr Ala Ala Asp Gly Arg Trp
                20                  25                  30

Gln Leu Leu Gln Lys Ser Ile Gly Ile Ser Ser Met His Met Gln Leu
            35                  40                  45

Leu Lys Asn Asp Arg Val Val Met Tyr Asp Arg Thr Asp Phe Gly Pro
        50                  55                  60

Ser Thr Leu Pro Leu Ala Ser Gly Lys Cys His Asn Asp Pro Thr Asn
65                  70                  75                  80

Thr Ala Val Gln Val Asp Cys Thr Ala His Ser Val Glu Tyr Asp Val
                85                  90                  95

Leu Ser Asn Lys Phe Arg Ala Leu Thr Val Gln Ser Asn Val Trp Cys
                100                 105                 110

Ser Ser Gly Gly Val Met Pro Asp Gly Lys Leu Val Gln Thr Gly Gly
            115                 120                 125

Phe Ser Glu Gly Glu Leu Arg Val Arg Val Phe Ser Pro Cys Glu Ser
        130                 135                 140

Cys Asp Trp His Glu Thr Pro Asn Gly Leu Ala Ala Lys Arg Trp Tyr
145                 150                 155                 160

Ala Thr Asn His Val Leu Pro Asp Gly Arg Gln Ile Val Val Gly Gly
                165                 170                 175

Arg Glu Gln Phe Asn Tyr Glu Phe Val Pro Lys Asn Ile Ala Ala Asp
            180                 185                 190

Thr Phe Lys Leu His Phe Leu Ser Glu Thr Asn Glu Arg Gly Val Glu
        195                 200                 205

Asn Asn Leu Tyr Pro Phe Val Phe Leu Asn Val Asp Gly Asn Leu Phe
    210                 215                 220

Ile Phe Ala Asn Asn Arg Ala Ile Leu Leu Asp Tyr Val Asn Asn Lys
225                 230                 235                 240
```

Val Val Lys Thr Tyr Pro Lys Ile Pro Gly Gly Glu Pro Arg Ser Tyr
            245                 250                 255

Pro Ser Thr Gly Ser Ala Val Leu Leu Pro Leu Lys Asn Leu Thr Ala
            260                 265                 270

Ala Thr Ile Gln Ala Glu Val Leu Val Cys Gly Gly Ala Pro Lys Gly
            275                 280                 285

Ser Phe Val Gln Ala Leu Gln Gly Lys Phe Val Lys Ala Leu Asn Thr
            290                 295                 300

Cys Ala Arg Ile Ser Ile Thr Asp Pro Lys Pro Lys Trp Val Leu Glu
305                 310                 315                 320

Thr Met Pro Leu Ala Arg Val Met Gly Asp Met Val Leu Leu Pro Asn
                    325                 330                 335

Gly Lys Val Leu Val Ile Asn Gly Ala Arg Ser Gly Ser Ala Gly Trp
                    340                 345                 350

Asp Leu Gly Arg Asp Pro Val Leu Asn Pro Val Leu Tyr Met Pro Asp
                355                 360                 365

Asn Glu Ile Glu Ser Arg Phe Lys Ile Leu Asn Pro Thr Lys Ile Pro
    370                 375                 380

Arg Met Tyr His Ser Thr Ala Val Leu Leu Arg Asp Gly Arg Val Leu
385                 390                 395                 400

Val Gly Gly Ser Asn Pro His Ala Tyr Tyr Asn Phe Thr Gly Val Leu
                    405                 410                 415

Tyr Pro Thr Glu Leu Ser Leu Glu Ala Phe Tyr Pro Gly Tyr Leu Asp
                420                 425                 430

Ala Lys Phe Asn Asn Leu Arg Pro Thr Ile Val Ala Pro Lys Ser Met
            435                 440                 445

Ser Gly Ile Arg Tyr Asn Lys Lys Leu Lys Ile Lys Val Val Ile Thr
            450                 455                 460

Gly Glu Val Thr Leu Asn Leu Leu Ser Val Thr Met Val Ser Pro Ala
465                 470                 475                 480

Phe Asn Thr His Ser Phe Ser Met Asn Gln Arg Leu Leu Val Leu Gly
                    485                 490                 495

Asn Asp Lys Val Met Ala Ser Gly Lys Ser Thr Tyr Glu Ile Glu Val
                500                 505                 510

Met Thr Pro Gly Ser Gly Asn Leu Ala Pro Ala Gly Phe Tyr Leu Leu
            515                 520                 525

Phe Val Val His Gln Asp Ile Pro Ser Gln Gly Ile Trp Val His Leu
            530                 535                 540

Lys
545

<210> SEQ ID NO 126
<211> LENGTH: 508
<212> TYPE: PRT
<213> ORGANISM: Gossypium hirsutum

<400> SEQUENCE: 126

Met Gln Ile Leu Pro Phe Arg Gly Gly Ala Leu Val Cys Phe Ile Ala
1               5                   10                  15

Ser Leu Leu Phe Val Ala Ser Phe Cys Asn Ala Asp Ala Lys Thr Val
            20                  25                  30

Glu Val Val Gly Ala Gly Glu Cys Ala Asp Cys Ala Glu Asn Asn Leu
        35                  40                  45

Glu Ile Ser Gln Ala Phe Ser Gly Leu Arg Val Ser Ile Asp Cys Lys

-continued

```
             50                  55                  60
Pro Glu Asn Gly Lys Asn Phe Lys Thr Arg Gly Ser Gly Glu Leu Asp
 65                  70                  75                  80

Lys Gln Gly Asn Phe Lys Val Phe Val Pro Glu Asp Leu Val Glu Asn
                 85                  90                  95

Gly Glu Leu Lys Glu Glu Cys Tyr Ala Gln Leu His Ser Val Ser Ala
                100                 105                 110

Ala Pro Cys Pro Ala His Asp Gly Leu Glu Ser Ala Lys Leu Val Leu
                115                 120                 125

Lys Ser Arg Ser Asp Gly Lys His Gly Phe Gly Leu Lys Gly Lys Leu
130                 135                 140

Arg Phe Ser Pro Leu Thr Cys Ala Ser Ala Phe Phe Trp Pro His Phe
145                 150                 155                 160

Lys Phe Pro Pro Leu Pro Lys Trp Asn His Pro Leu Pro Lys Phe
                165                 170                 175

Pro Leu Pro Pro Phe Lys Gly Phe His His Tyr Pro Ile Ile Pro
                180                 185                 190

Pro Ile Tyr Lys Lys Pro Leu Pro Pro Ser Pro Val Tyr Lys Pro
                195                 200                 205

Pro Pro Val Pro Val Asn Pro Pro Val Pro Ile Tyr Lys Pro Pro Pro
    210                 215                 220

Val Pro Val Tyr Lys Pro Pro Val Pro Val Lys Pro Leu Pro Pro
225                 230                 235                 240

Pro Val Pro Ile Tyr Lys Pro Pro Val Glu Lys Pro His Pro Pro
                245                 250                 255

Pro Val Pro Val Tyr Lys Pro Pro Val Pro Val Tyr Lys Lys Pro
                260                 265                 270

Cys Pro Pro Val Pro Val Tyr Lys Ser Pro Pro Val Pro Val Tyr
                275                 280                 285

Lys Lys Pro His Pro Pro Val Pro Val Tyr Lys Lys Pro His Pro
                290                 295                 300

Pro Pro Val Pro Val Tyr Lys Lys Pro Cys Pro Pro Val Pro Val
305                 310                 315                 320

Tyr Lys Ser Pro Pro Val Pro Glu Pro His Pro Pro Val Pro Val
                325                 330                 335

Tyr Lys Lys Pro His Pro Pro Val Pro Val Tyr Lys Lys Pro Cys
                340                 345                 350

Pro Pro Pro Val Pro Val Tyr Lys Ser Pro Pro Val Pro Glu Pro His
                355                 360                 365

Pro Pro Pro Val Pro Val His Lys Pro Pro Val Pro Val Tyr Lys
                370                 375                 380

Lys Arg Val Pro Pro Val Pro Ile Tyr Lys Pro Pro Val Pro
385                 390                 395                 400

Val Tyr Asn Lys Pro Leu Pro Pro Val Pro Val Tyr Thr Lys Pro
                405                 410                 415

Leu Pro Pro Pro Val Thr Tyr Lys Pro Lys Pro Leu Pro Pro Ile
                420                 425                 430

Pro Tyr Lys Pro Leu Pro Pro Leu Pro Lys Ile Pro Pro Phe Pro Lys
                435                 440                 445

Lys Pro Cys Pro Pro Leu Pro Lys Leu Pro Pro Leu Pro Lys Ile Pro
                450                 455                 460

Pro Lys Tyr Phe His His His Pro Pro Leu Pro Lys Leu Pro Pro Leu
465                 470                 475                 480
```

```
-continued

Pro Lys Ile Pro Pro Lys Tyr Phe His His His Pro Lys Phe Gly Lys
                485                 490                 495

Trp Pro Ser Leu Pro Pro Phe Ala Pro His His Pro
            500             505
```